(12) United States Patent
Hanks et al.

(10) Patent No.: US 10,617,749 B1
(45) Date of Patent: Apr. 14, 2020

(54) COMPOSITION OF MATTER AND METHODS FOR ALTERATION OF DENDRITIC CELL METABOLISM TO AUGMENT CANCER VACCINE EFFICACY

(71) Applicant: Duke University, Durham, NC (US)

(72) Inventors: Brent Hanks, Durham, NC (US); Fei Zhao, Durham, NC (US)

(73) Assignee: Duke University, Durham, NC (US)

( * ) Notice: Subject to any disclaimer, the term of this patent is extended or adjusted under 35 U.S.C. 154(b) by 268 days.

(21) Appl. No.: 15/441,816

(22) Filed: Feb. 24, 2017

Related U.S. Application Data

(60) Provisional application No. 62/299,224, filed on Feb. 24, 2016.

(51) Int. Cl.
| | |
|---|---|
| *A61K 45/06* | (2006.01) |
| *A61K 39/00* | (2006.01) |
| *C12N 5/0784* | (2010.01) |

(52) U.S. Cl.
CPC .......... *A61K 39/0011* (2013.01); *A61K 45/06* (2013.01); *C12N 5/0639* (2013.01); *A61K 2039/5154* (2013.01); *C12N 2501/415* (2013.01); *C12N 2501/72* (2013.01)

(58) Field of Classification Search
CPC ... A61K 39/0011; A61K 45/06; C12N 5/0639
USPC ...................................................... 424/277.1
See application file for complete search history.

(56) References Cited

PUBLICATIONS

Gura (Science. 1997; 278: 1041-1042).*
Dennis (Nature. Aug. 7, 2006; 442: 739-741).*
Reagan-Shaw et al. (FASEB J, 2007, 22: 659-61).*
Seruga et al. (2015, Clin Cancer Res, 21:4554-60).*
Sim et al. (Mediators Inflamm. 2016, 2016:2636701, doi: 10.1155/2016/2636701, Epub Feb. 11, 2016, pp. 1-10).*
Banchereau J, et al. "Dendritic cells and the control of immunity." Nature 1998;392(6673):245-52.
Banchereau et al., "Dendritic cells as vectors for therapy," Cell, vol. 106, pp. 271-274 (Aug. 10, 2001).
Belkaid et al., "Tuning microenvironments: induction of regulatory T cells by dendritic cells." Immunity. 2008;29(3):362-71.
Biswas SK. "Metabolic Reprogramming of Immune Cells in Cancer Progression. Immunity." 2015;43(3):435-49.
Collier, et al., "Effect of fatty acid oxidation inhibition on glucose metabolism in diabetic rats," Hormone and metabolic research = Hormon-undStoffwechselforschung = Hormones et metabolisme 25, 9-12. (1993).
Damsky, et al. "βeta-catenin signaling controls metastasis in Braf-activated Pten-deficient melanomas." Cancer Cell. 2011;20(6):741-54.
Dankort, et al. "Braf(V600E) cooperates with Pten loss to induce metastatic melanoma," Nat Genet. 2009;41(5):544-52.
Dannull, et al., "Melanoma immunotherapy using mature DCs expressing the constitutive proteasome," J Clin Invest. 2013;123(7):3135-3145.
Darrasse-Jeze, et al., "How Numbers, Nature, and Immune Status of Foxp3 Regulatory T-Cells Shape the Early Immunological Events in Tumor Development," Frontiers in immunology. 2013;4:292.
Enk, et al. "Dendritic cells as mediators of tumor-induced tolerance in metastatic melanoma," Int J Cancer. 1997;73:309-16.
Everts, et al., "TLR-driven early glycolytic reprogramming via the kinases TBK1-IKK varepsilon supports the anabolic demands of dendritic cell activation," Nat Immunol. 2014;15(4):323-32.
Fallarino, et al.,. "The combined effects of tryptophan starvation and tryptophan catabolites down-regulate T cell receptor {zeta)-chain and induce a regulatory phenotype in naive T cells," J Immunol. 2006;176:6752-61.
Feuerstein, et al., "A method for the production of cryopreserved aliquots of antigen-preloaded, mature dendritic cells ready for clinical use," J Immunol Methods 245 (2000) pp. 15-29.
Gabrilovich D. "Mechanisms and functional significance of tumor-induced dendritic cell defects," Nature Rev Immunol. 2004;4:941-52.
Ghiringhelli et al., "Tumor cells convert immature myeloid dendritic cells into TGF-beta-secreting cells inducing CD4+CD25+ regulatory T cell proliferation,". J Exp Med. 2005;202(7):919-29.
Gilboa E. "DC-based cancer vaccines," J Clin Invest. 2007;117(5):1195-203.
Hanks, et al., "Type III TGF-β Receptor Downregulation Generates an Immunotolerant Tumor Microenvironment," J Clin Invest. 2013;123(9):3925-40.
He et al., "Immunization with Lentiviral Vector-Transduced Dendritic Cells Induces Strong and Long-Lasting T Cell Responses and Therapeutic Immunity," J Immunol 2005; 174:3808-3817.
Holtzhausen, et al., "Early carcinogenesis involves the establishment of immune privilege via intrinsic and extrinsic regulation of indoleamine 2,3-dioxygenase-1: translational implications in cancer immunotherapy," Frontiers Immunology. 2014;5:1-9.
Holtzhausen, et al., Melanoma-derived Wnt5a Promotes Local Dendritic-Cell Expression of IDO and Immunotolerance: Opportunities for Pharmacologic Enhancement of Immunotherapy. Cancer Immunol Res. 2015;3(9):1082-95.
Inaba, et al., "Generation of large numbers of dendritic cells from mouse bone marrow cultures supplemented with granulocyte/macrophage colony-stimulating factor," The Journal of experimental medicine 176, 1693-1702. (1992).
Katz, et al., "Indoleamine 2,3-dioxygenase in T-cell tolerance and tumoral immune escape," Immunol Rev. 2008;222:206-21.
Krawczyk, et al., "Toll-like receptor-induced changes in glycolytic metabolism regulate dendritic cell activation," Blood. 2010;115(23):4742-9.
Ma, et al., "Dendritic cells in the cancer microenvironment," Journal of Cancer. 2013;4(1):36-44.
Malinarich, et al., "High mitochondrial respiration and glycolytic capacity represent a metabolic phenotype of human tolerogenic dendritic cells," J Immunol. 2015;194(11):5174-86.

(Continued)

*Primary Examiner* — Yan Xiao
(74) *Attorney, Agent, or Firm* — Quarles & Brady LLP

(57) ABSTRACT

This disclosure provides compositions of matter and methods for alteration of dendritic cell metabolism to augment cancer vaccine efficacy. The compositions and methods can involve regulation of fatty acid oxidation.

13 Claims, 35 Drawing Sheets
(27 of 35 Drawing Sheet(s) Filed in Color)
Specification includes a Sequence Listing.

(56) References Cited

PUBLICATIONS

Melief. "Cancer immunotherapy by dendritic cells," Immunity. 2008;29:372-83.

Mellor, et al., "Cutting edge: induced indoleamine 2,3 dioxygenase expression in dendritic cell subsets suppresses T cell clonal expansion," J Immunol. 2003;171:1652-5.

Munn, et al., "Prevention of allogeneic fetal rejection by tryptophan catabolism," Science, 1998; 281:1191-3.

Munn, et al., "Potential regulatory function of human dendritic cells expressing indoleamine 2,3-dioxygenase," Science. 2002;297(5588):1867-70.

Munn, et al., "Expression of indoleamine 2,3-dioxygenase by plasmacytoid dendritic cells in tumor-draining lymph nodes," J Clin Invest. 2004;114(2):280-90.

Nair, et al., "Isolation and generation of human dendritic cells," Current Protocols in Immunology, pp. 32.31-32.23, (2012).

Postow, et al. "Nivolumab and ipilimumab versus ipilimumab in untreated melanoma," N Engl J Med. 2015;372(21):2006-17.

Scarlett, et al. "Ovarian cancer progression is controlled by phenotypic changes in dendritic cells," J Exp Med. 2012;209(3):495-506.

Sharma, et al., "Plasmacytoid dendritic cells from mouse tumor-draining lymph nodes directly activate mature Tregs via indoleamine-2,3-dioxygenase," J Clin Invest. 2007;117(9):2570-82.

Sharma, et al., "The PTEN pathway in Tregs is a critical driver of the suppressive tumor microenvironment," Science advances. 2015;1(10):e1500845.

Sharma, et al., "An inherently bifunctional subset of Foxp3+ T helper cells is controlled by the transcription factor eos," Immunity. 2013;38(5):998-1012.

Shen, et al. "Cloned dendritic cells can present exogenous antigens on both MHC class I and class II molecules," J Immunol. 158, 2723-2730 (1997). Need this.

Sherwood, et al., "WNT5A-mediated beta-catenin-independent signalling is a novel regulator of cancer cell metabolism," Carcinogenesis, 2014;35(4):784-94.

Tacken et al., "Dendritic-cell immunotherapy: from ex vivo loading to in vivo targeting," Nature Reviews: Immunology Oct. 2007; vol. 7, pp. 790-802.

Zhao, et al. "Arsenite-induced pseudo-hypoxia results in loss of anchorage-dependent growth in BEAS-2B pulmonary epithelial cells," PloS one 9, e114549 (2014).

Zhao, et al. "Paracrine Wnt5a-β-Catenin Signaling Triggers a Metabolic Program that Drives Dendritic Cell Tolerization," Immunity, 48, 147-160, Jan. 16, 2018.

\* cited by examiner

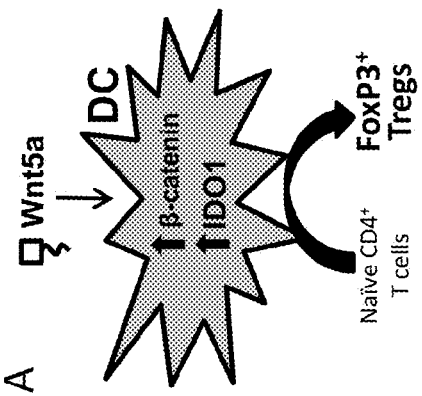
Figure 1A
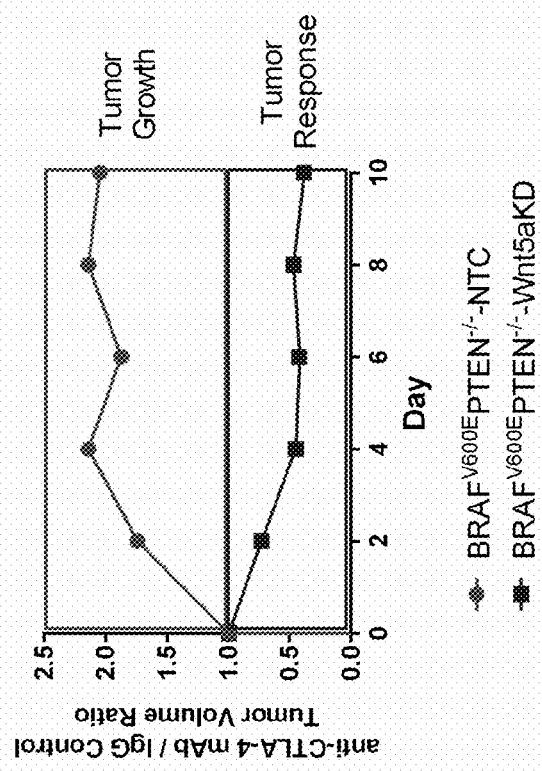
Figure 1B
Figure 1C
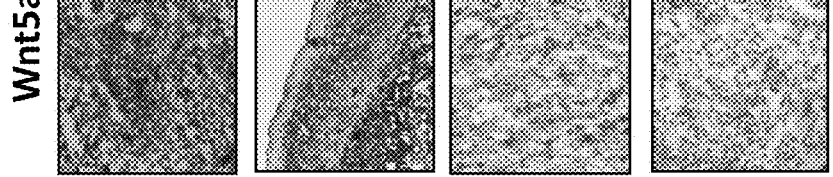
| | Stage | Wnt5a Staining | Clinical Response to anti-CTLA-4 ab |
|---|---|---|---|
| Wnt5a | IV | 3+ | PD |
| | IIIC | 3+ | PD |
| | IIIC | 1+ | CR |
| | IIIC | 1+ | CR |

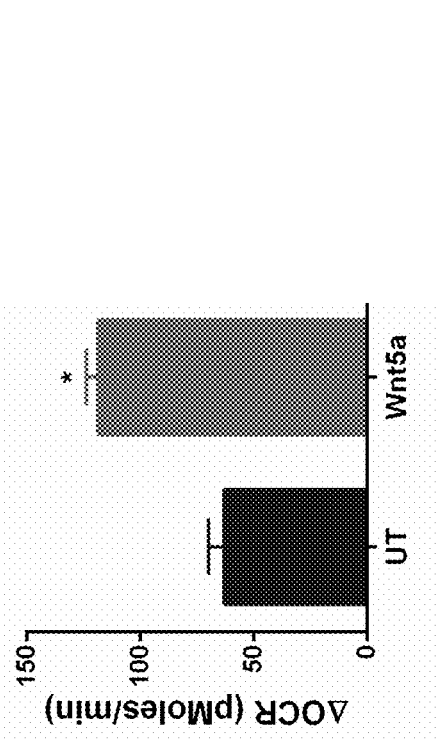
Figure 2A
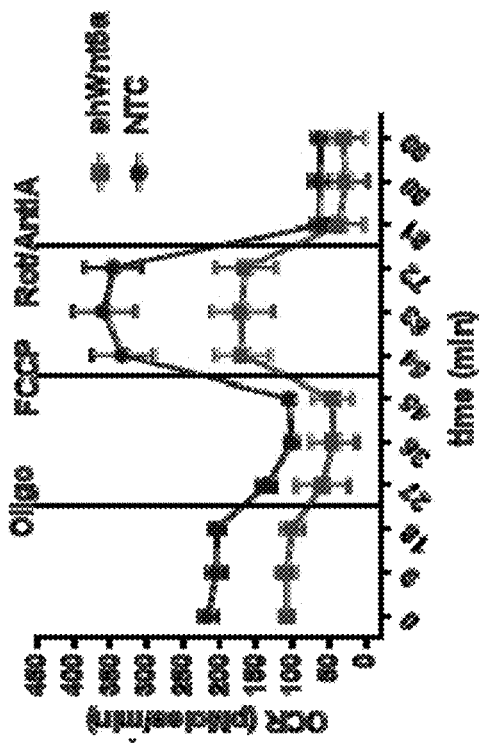
Figure 2B
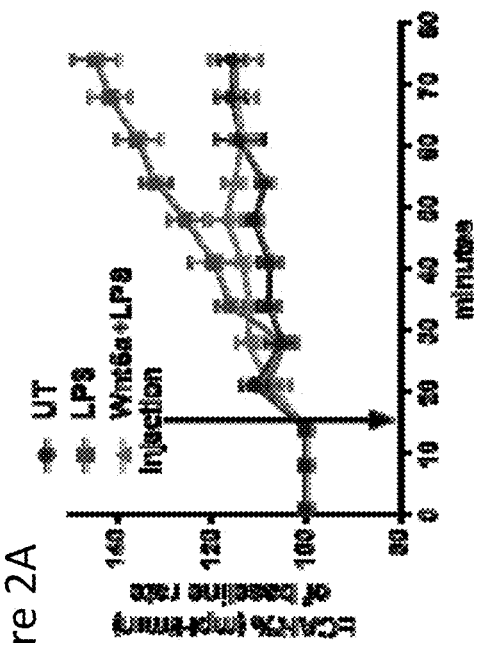
Figure 2C
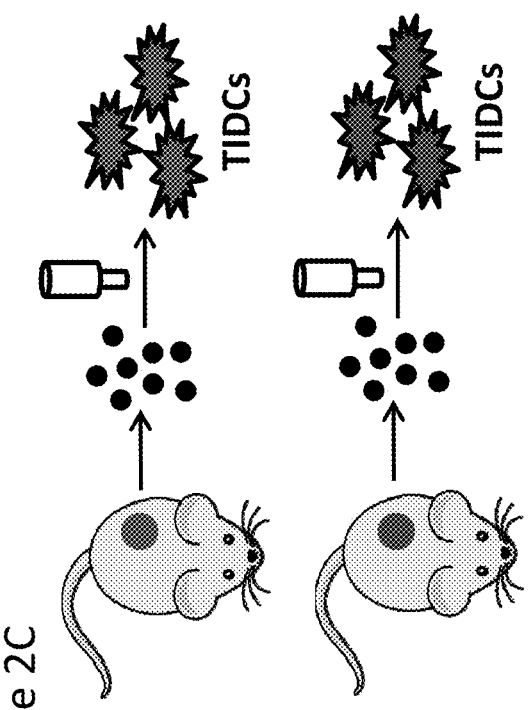

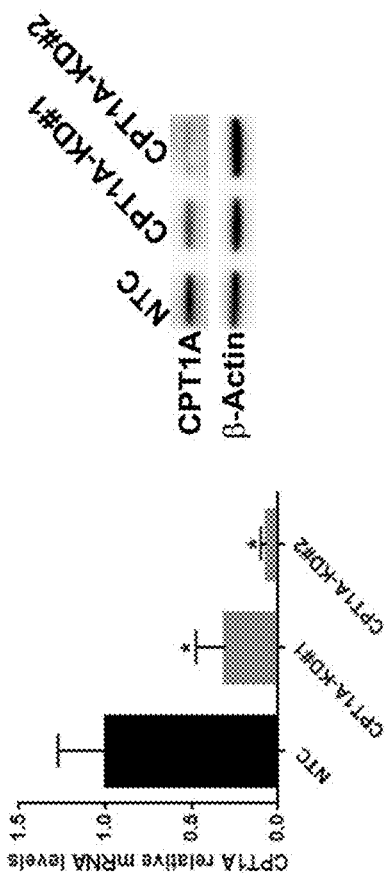
Figure 6A
Figure 6B
Figure 6C
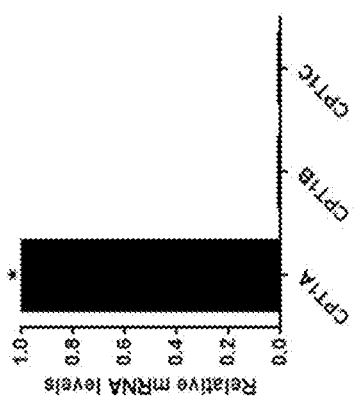
Figure 6D
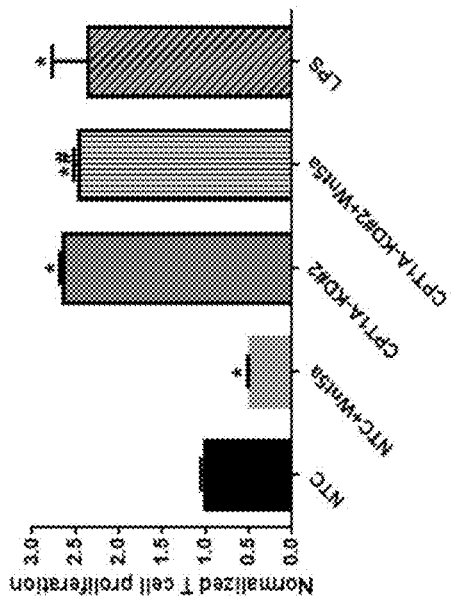
Figure 6E

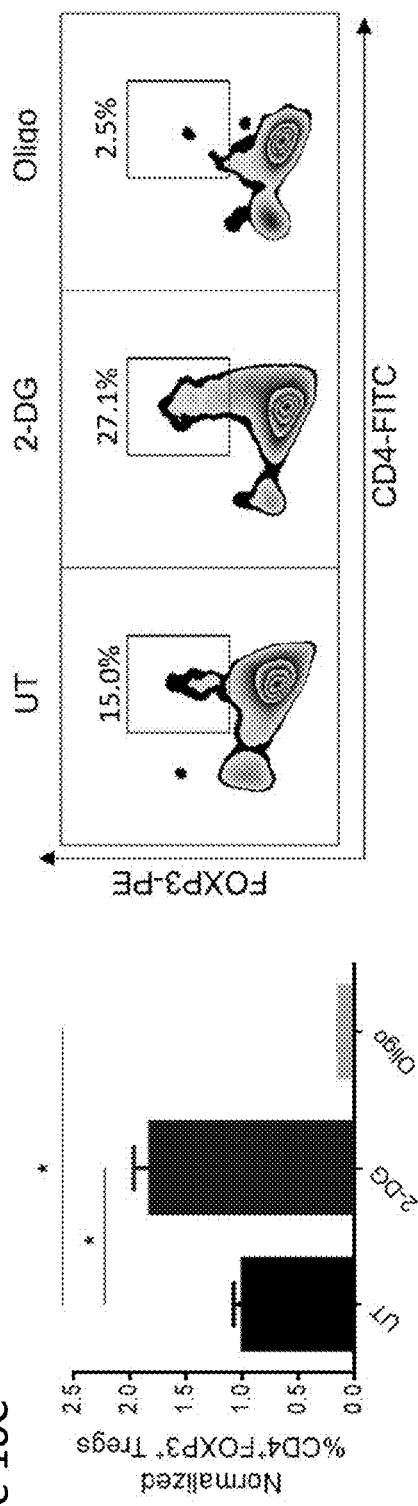
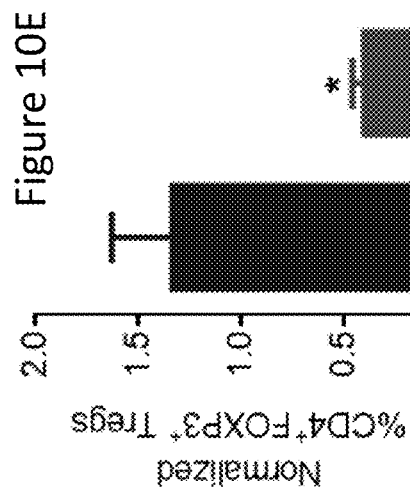
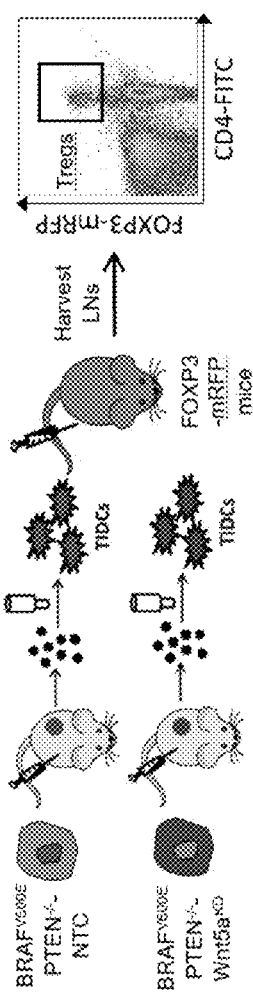
Figure 10C
Figure 10D
Figure 10E
Figure 10F

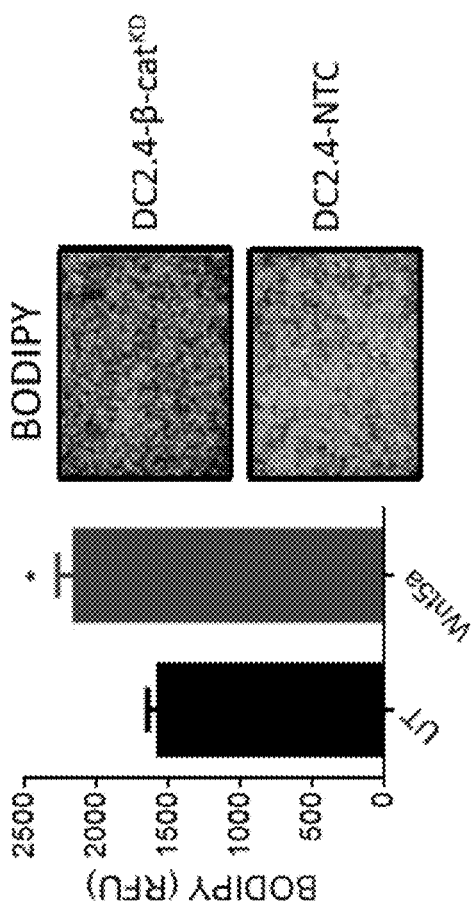
Figure 11A
Figure 11B
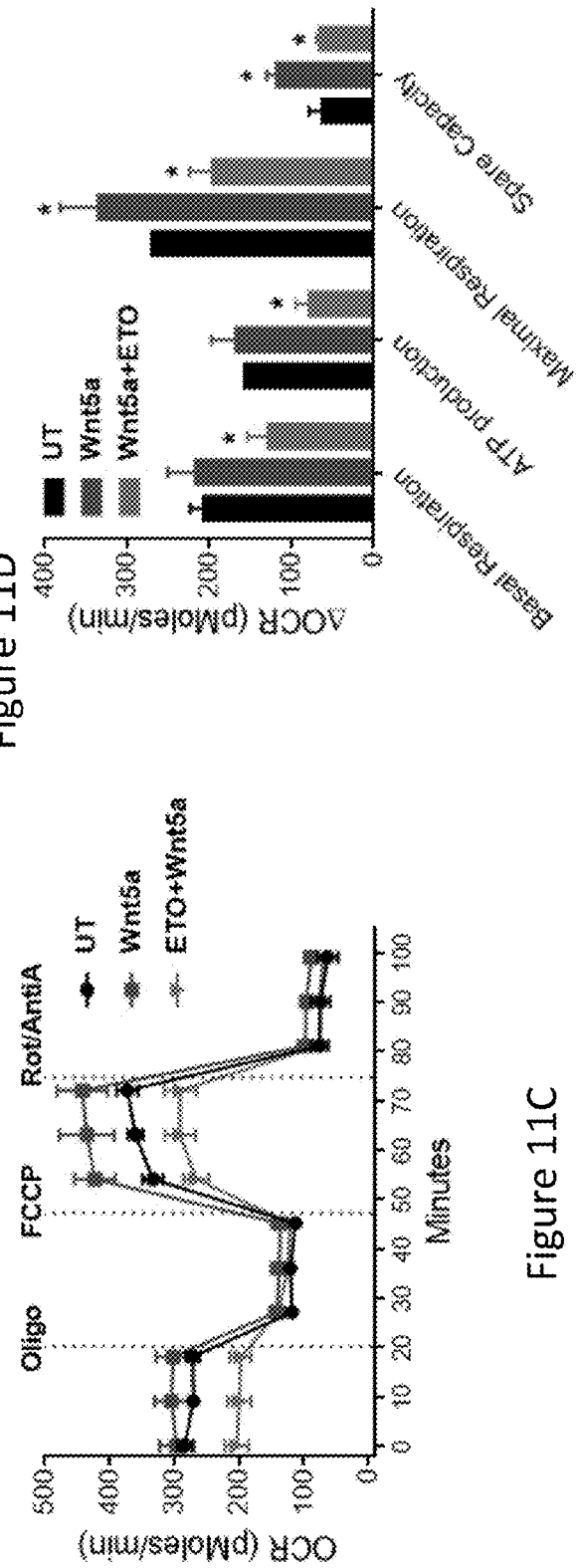
Figure 11C
Figure 11D

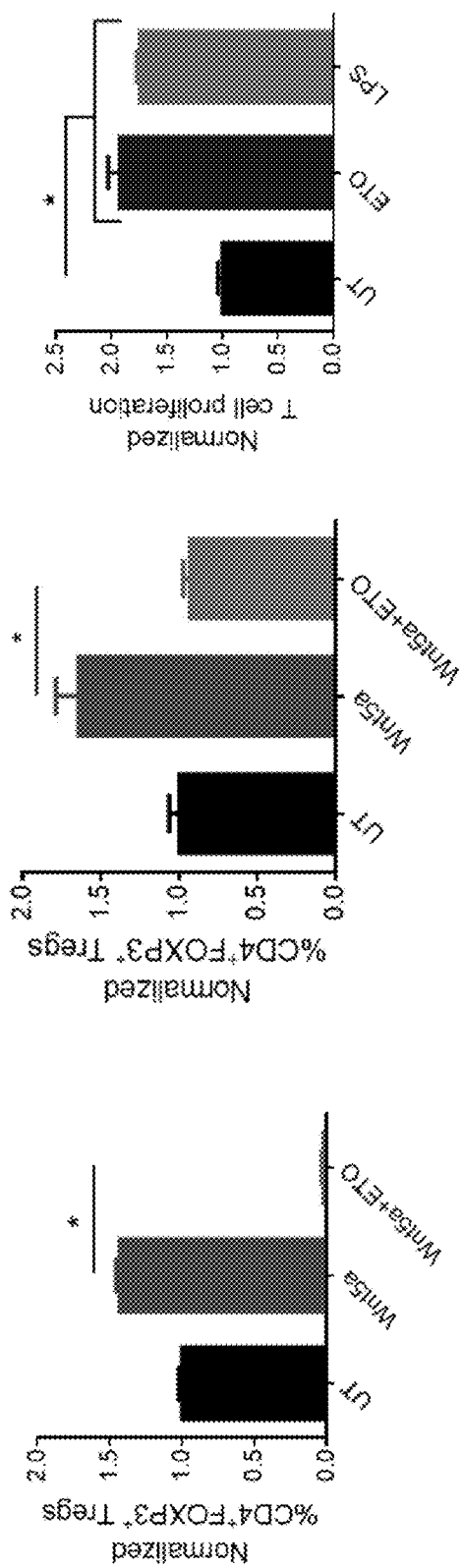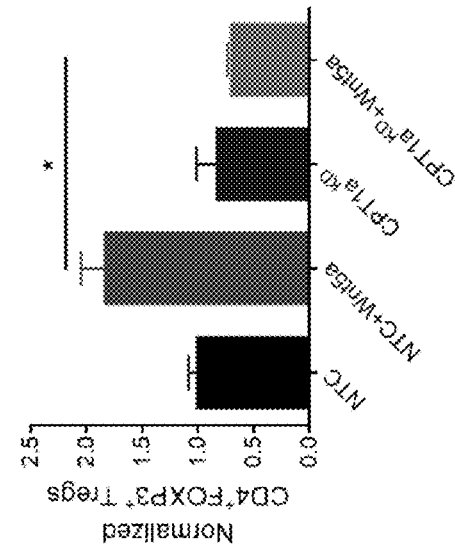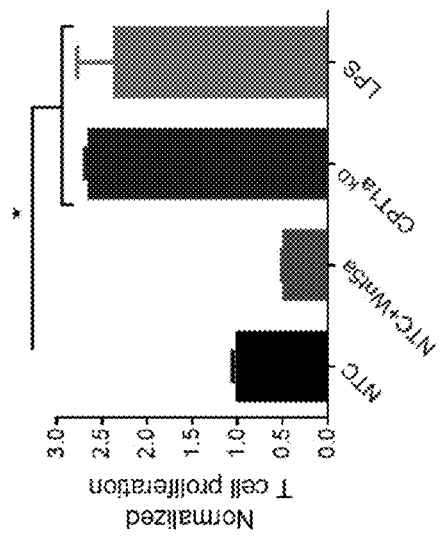

Figure 12A
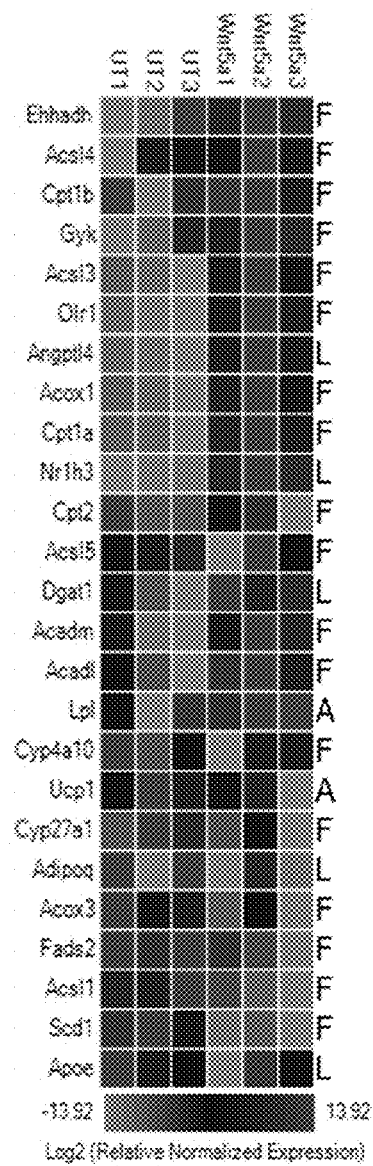
Figure 12B
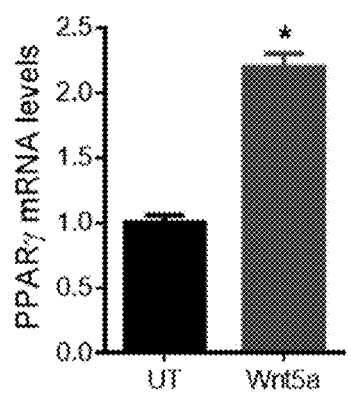
Figure 12C
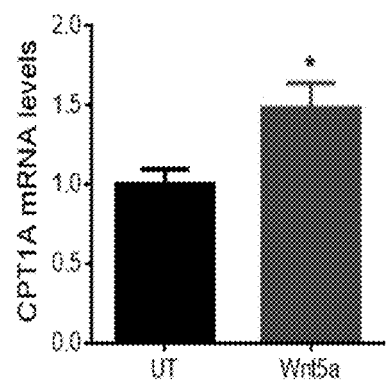
Figure 12D
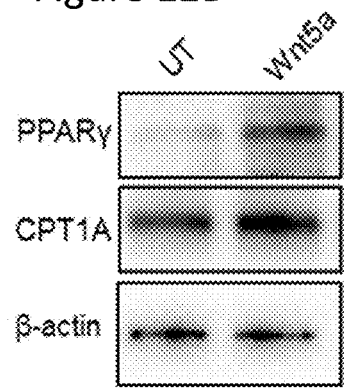
Figure 12E
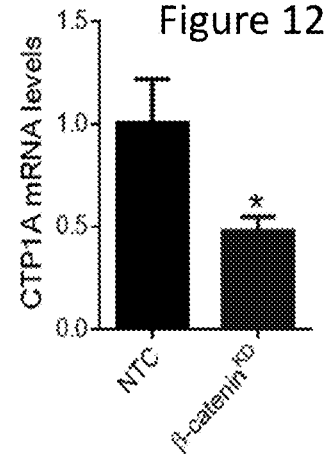
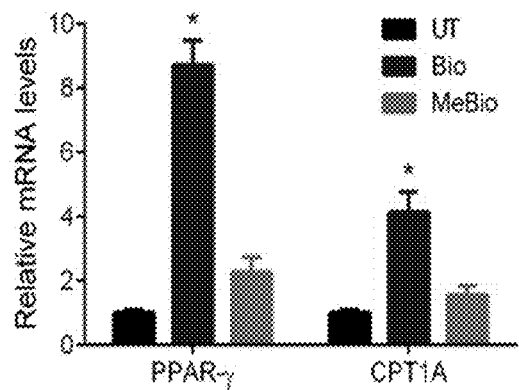
Figure 12F

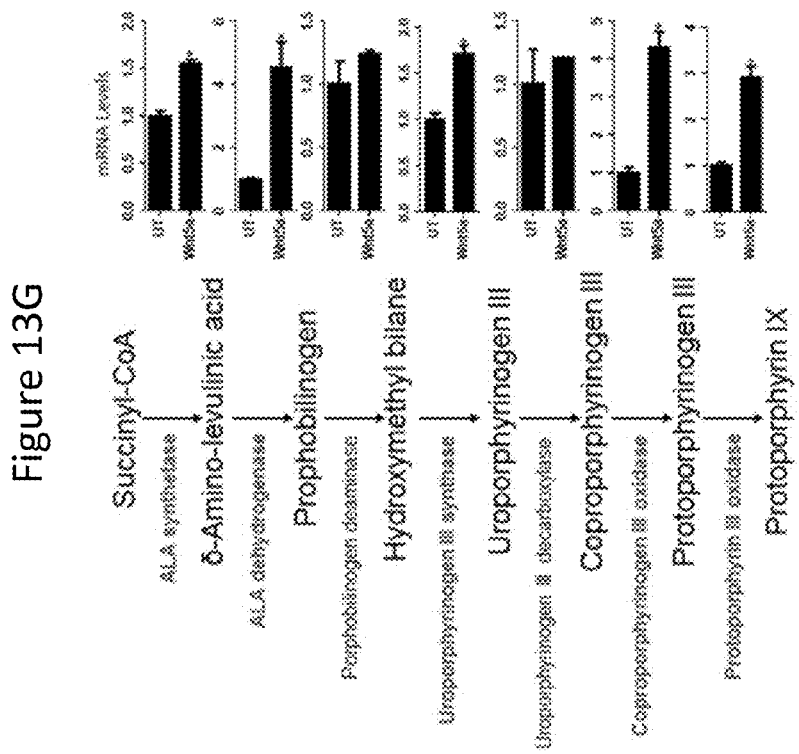
Figure 13G
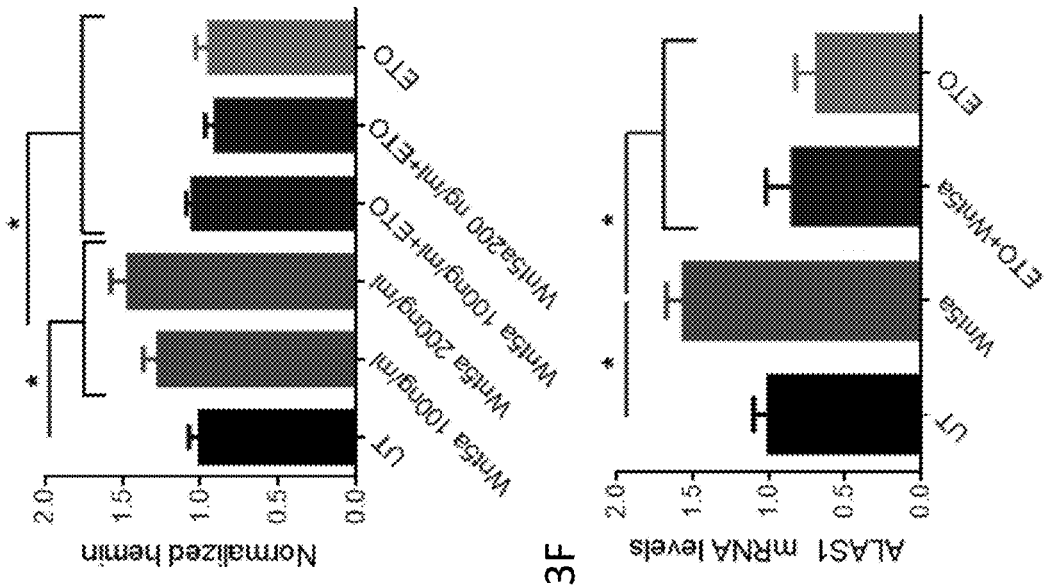
Figure 13E
Figure 13F

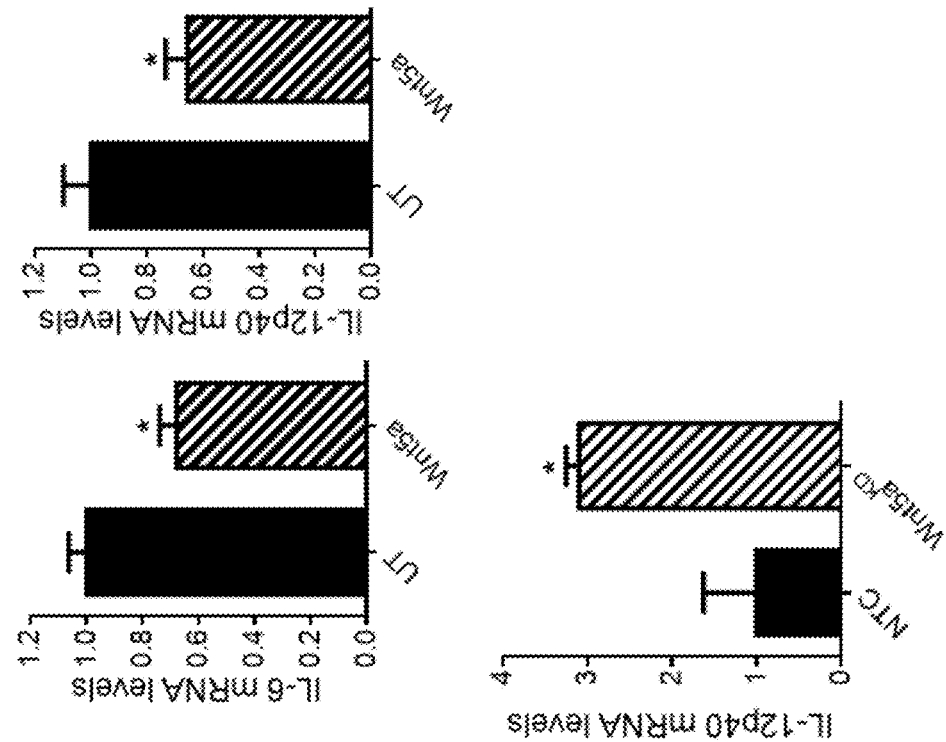
Figure 14E
Figure 14F
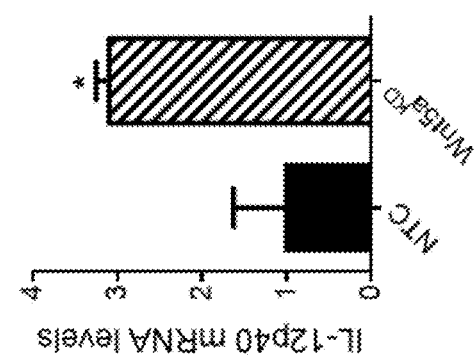
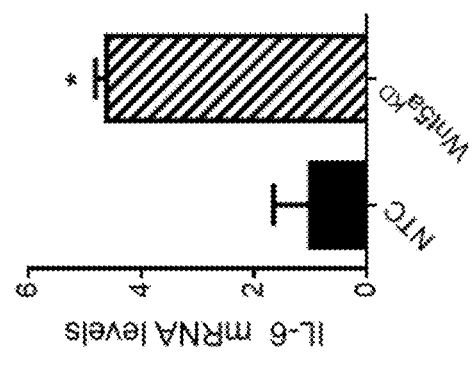
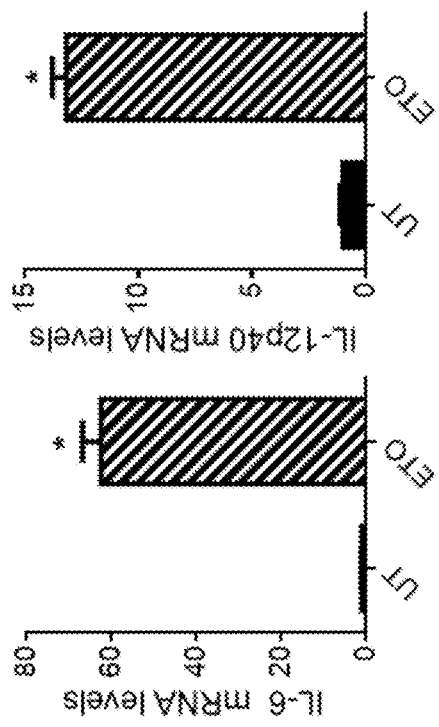
Figure 14G

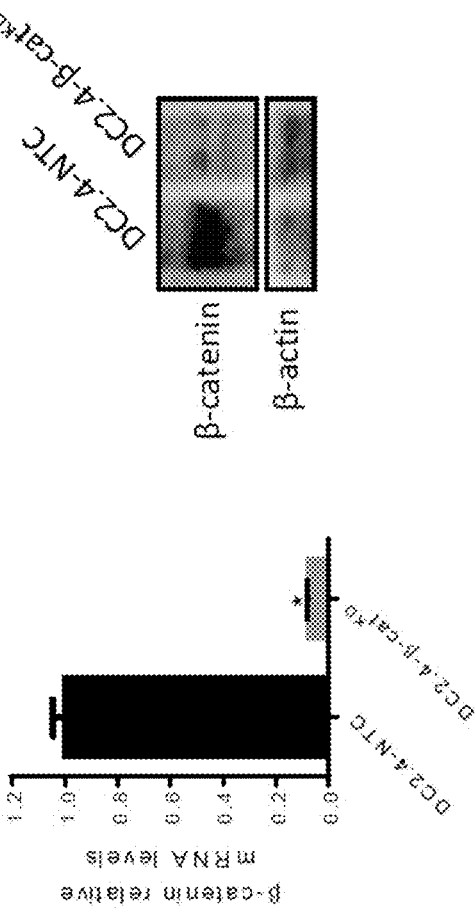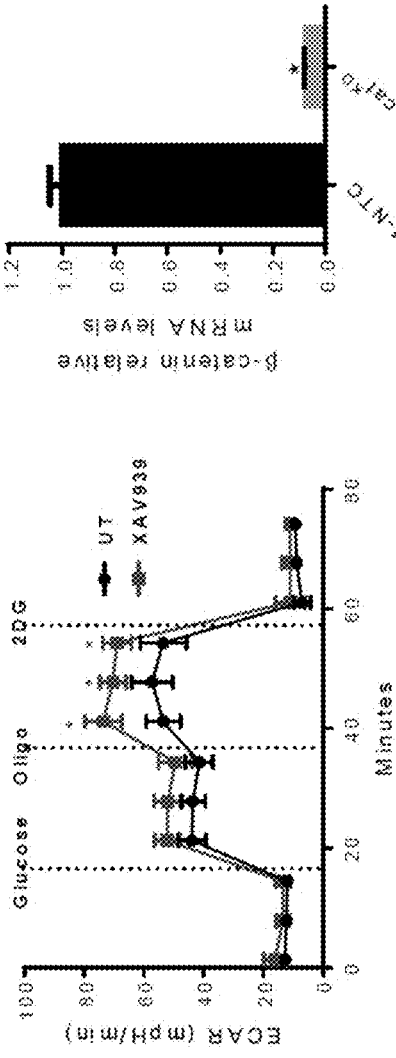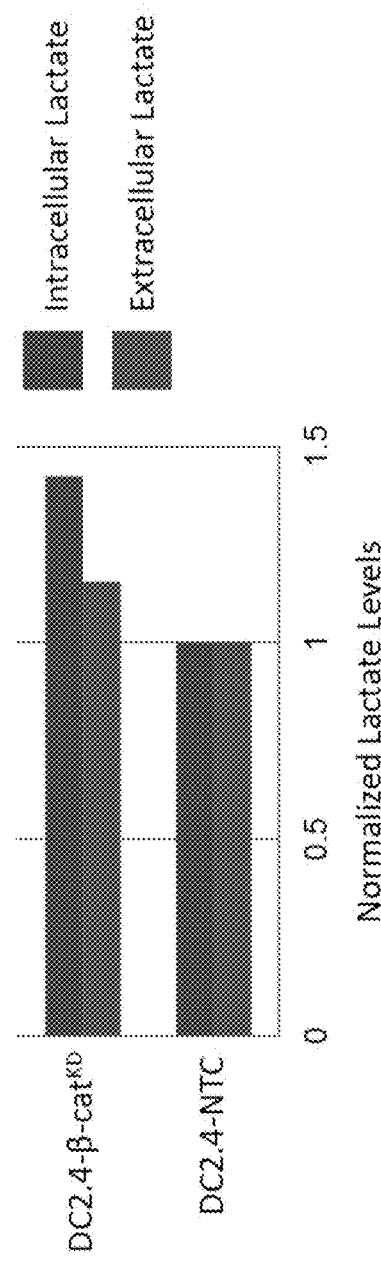
Figure 20A
Figure 20B
Figure 20C
Figure 20D

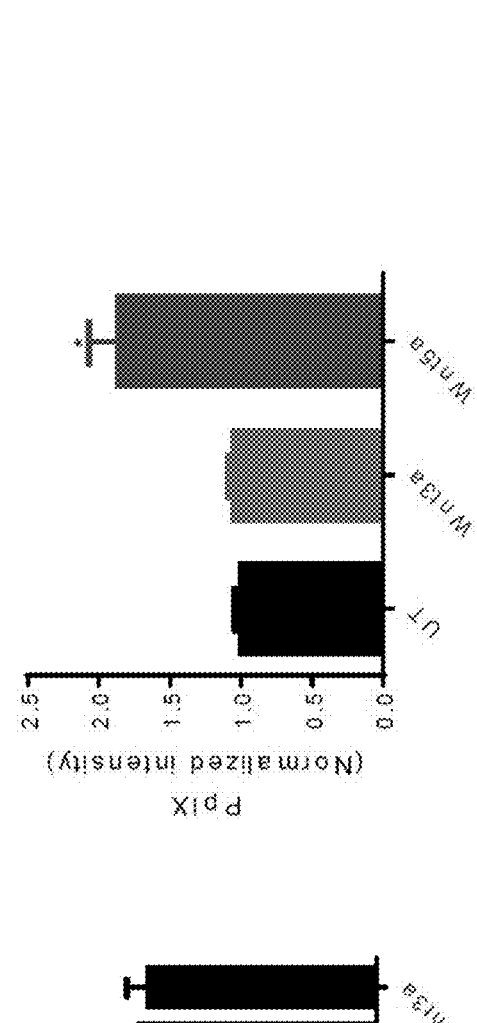
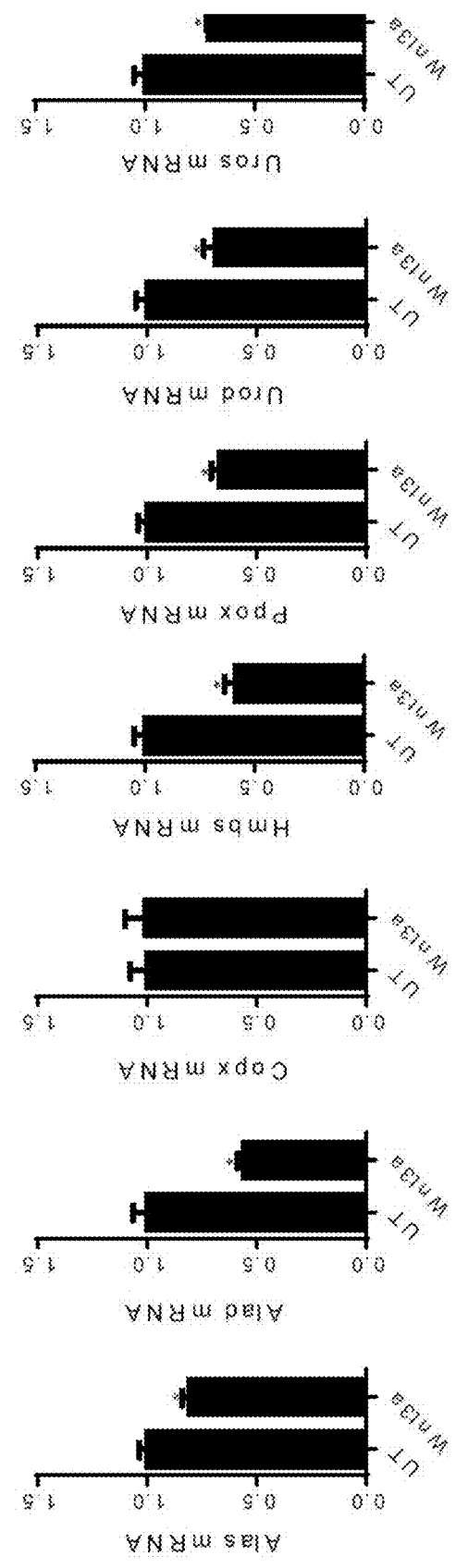
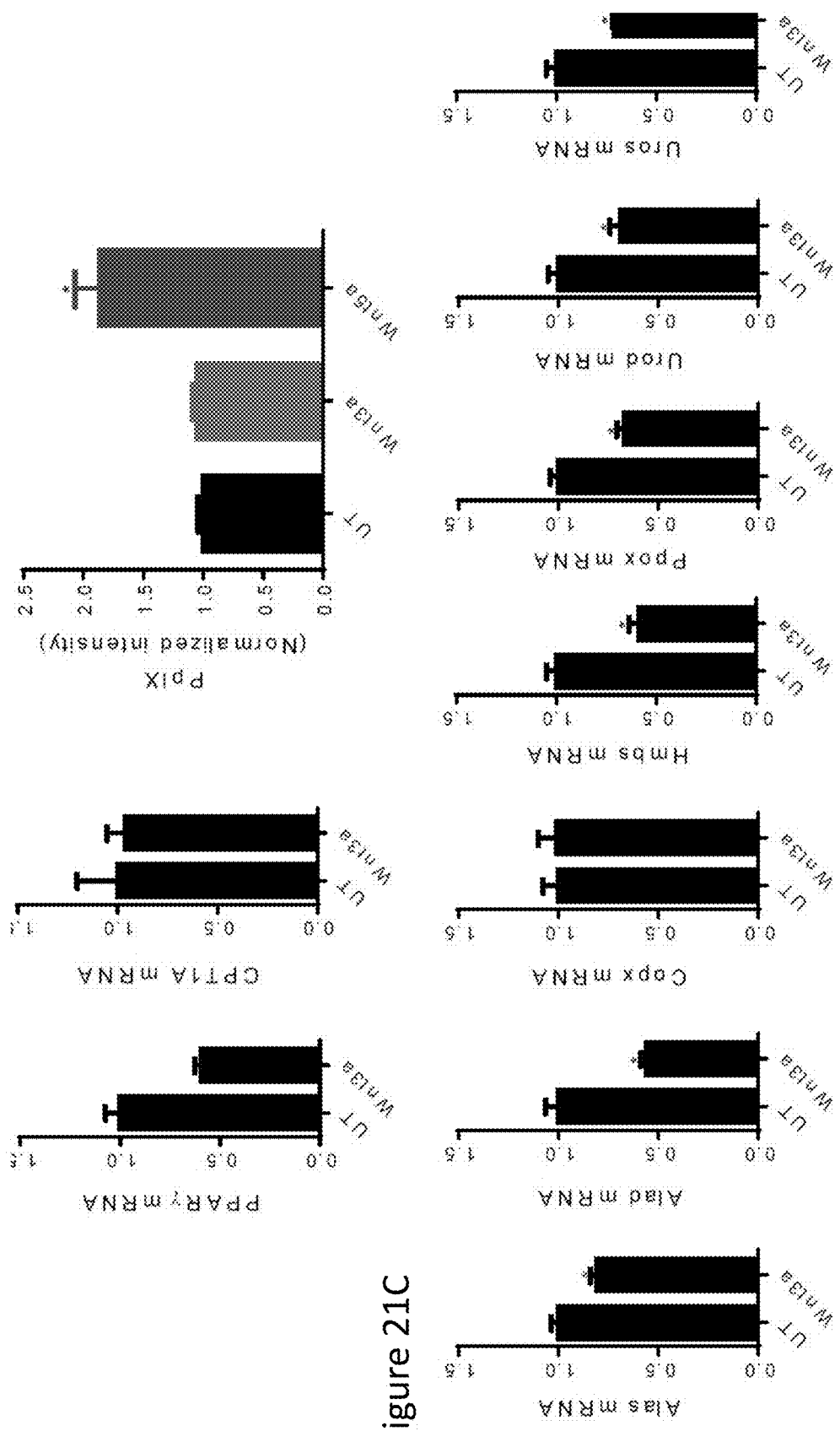
Figure 21A
Figure 21B
Figure 21C

SEQUENCE LISTING

```
<160> NUMBER OF SEQ ID NOS: 30

<210> SEQ ID NO 1
<211> LENGTH: 58
<212> TYPE: DNA
<213> ORGANISM: Artificial Sequence
<220> FEATURE:
<223> OTHER INFORMATION: synthetic

<400> SEQUENCE: 1
ccgggctatg gtgtttccta cattactcga gtaatgtagg aaacaccata gcttttttg     58

<210> SEQ ID NO 2
<211> LENGTH: 8
<212> TYPE: PRT
<213> ORGANISM: Artificial Sequence
<220> FEATURE:
<223> OTHER INFORMATION: synthetic

<400> SEQUENCE: 2

Ser Ile Ile Asn Phe Glu Lys Leu
1               5

<210> SEQ ID NO 3
<211> LENGTH: 20
<212> TYPE: DNA
<213> ORGANISM: Artificial Sequence
<220> FEATURE:
<223> OTHER INFORMATION: synthetic

<400> SEQUENCE: 3
ggctgtattc ccctccatcg                                                20

<210> SEQ ID NO 4
<211> LENGTH: 22
<212> TYPE: DNA
<213> ORGANISM: Artificial Sequence
<220> FEATURE:
<223> OTHER INFORMATION: synthetic

<400> SEQUENCE: 4
ccagttggta acaatgccat gt                                             22

<210> SEQ ID NO 5
<211> LENGTH: 21
<212> TYPE: DNA
<213> ORGANISM: Artificial Sequence
```

<220> FEATURE:
<223> OTHER INFORMATION: synthetic

<400> SEQUENCE: 5
gcccttTggt gactttatgg a                                              21

<210> SEQ ID NO 6
<211> LENGTH: 20
<212> TYPE: DNA
<213> ORGANISM: Artificial Sequence
<220> FEATURE:
<223> OTHER INFORMATION: synthetic

<400> SEQUENCE: 6
gcagcaggtt gtcttggatg                                                20

<210> SEQ ID NO 7
<211> LENGTH: 21
<212> TYPE: DNA
<213> ORGANISM: Artificial Sequence
<220> FEATURE:
<223> OTHER INFORMATION: synthetic

<400> SEQUENCE: 7
ctcagtggga gcgactcttc a                                              21

<210> SEQ ID NO 8
<211> LENGTH: 21
<212> TYPE: DNA
<213> ORGANISM: Artificial Sequence
<220> FEATURE:
<223> OTHER INFORMATION: synthetic

<400> SEQUENCE: 8
ggcctctgtg gtacacgaca a                                              21

<210> SEQ ID NO 9
<211> LENGTH: 20
<212> TYPE: DNA
<213> ORGANISM: Artificial Sequence
<220> FEATURE:
<223> OTHER INFORMATION: synthetic

<400> SEQUENCE: 9
ttcaacacta cacgcatccc                                                20

<210> SEQ ID NO 10
<211> LENGTH: 19
<212> TYPE: DNA
<213> ORGANISM: Artificial Sequence
<220> FEATURE:
<223> OTHER INFORMATION: syntehtic

<400> SEQUENCE: 10
gccctcatag agccagacc                                                 19

<210> SEQ ID NO 11
<211> LENGTH: 21
<212> TYPE: DNA
<213> ORGANISM: Artificial Sequence
<220> FEATURE:
<223> OTHER INFORMATION: synthetic

<400> SEQUENCE: 11
tcttcactga gttccgatgg g                                              21

```
<210> SEQ ID NO 12
<211> LENGTH: 20
<212> TYPE: DNA
<213> ORGANISM: Artificial Sequence
<220> FEATURE:
<223> OTHER INFORMATION: synthetic

<400> SEQUENCE: 12
acgccagaga tgcctttcc                                            20

<210> SEQ ID NO 13
<211> LENGTH: 23
<212> TYPE: DNA
<213> ORGANISM: Artificial Sequence
<220> FEATURE:
<223> OTHER INFORMATION: synthetic

<400> SEQUENCE: 13
tagtccttcc tacccaatt tcc                                        23

<210> SEQ ID NO 14
<211> LENGTH: 21
<212> TYPE: DNA
<213> ORGANISM: Artificial Sequence
<220> FEATURE:
<223> OTHER INFORMATION: synthetic

<400> SEQUENCE: 14
ttggtcctta gccactcctt c                                         21

<210> SEQ ID NO 15
<211> LENGTH: 19
<212> TYPE: DNA
<213> ORGANISM: Artificial Sequence
<220> FEATURE:
<223> OTHER INFORMATION: synthetic

<400> SEQUENCE: 15
gaccagctgg acaacatac                                            19

<210> SEQ ID NO 16
<211> LENGTH: 18
<212> TYPE: DNA
<213> ORGANISM: Artificial Sequence
<220> FEATURE:
<223> OTHER INFORMATION: synthetic

<400> SEQUENCE: 16
ctggagtcca gcagactc                                             18

<210> SEQ ID NO 17
<211> LENGTH: 20
<212> TYPE: DNA
<213> ORGANISM: Artificial Sequence
<220> FEATURE:
<223> OTHER INFORMATION: synthetic

<400> SEQUENCE: 17
gaacacatgc ccacttgctg                                           20

<210> SEQ ID NO 18
<211> LENGTH: 22
<212> TYPE: DNA
<213> ORGANISM: Artificial Sequence
<220> FEATURE:
<223> OTHER INFORMATION: synthetic
```

<400> SEQUENCE: 18
cgtgctcatg gctggtgcaa ag                                    22

<210> SEQ ID NO 19
<211> LENGTH: 20
<212> TYPE: DNA
<213> ORGANISM: Artificial Sequence
<220> FEATURE:
<223> OTHER INFORMATION: synthetic

<400> SEQUENCE: 19
gcaacaacgc catctatgag                                       20

<210> SEQ ID NO 20
<211> LENGTH: 20
<212> TYPE: DNA
<213> ORGANISM: Artificial Sequence
<220> FEATURE:
<223> OTHER INFORMATION: synthetic

<400> SEQUENCE: 20
atctttgctg tcacaagagc                                       20

<210> SEQ ID NO 21
<211> LENGTH: 20
<212> TYPE: DNA
<213> ORGANISM: Artificial Sequence
<220> FEATURE:
<223> OTHER INFORMATION: synthetic

<400> SEQUENCE: 21
ggaggcgaga acatcaagcc                                       20

<210> SEQ ID NO 22
<211> LENGTH: 19
<212> TYPE: DNA
<213> ORGANISM: Artificial Sequence
<220> FEATURE:
<223> OTHER INFORMATION: synthetic

<400> SEQUENCE: 22
cggccttccc tcgtagtga                                        19

<210> SEQ ID NO 23
<211> LENGTH: 19
<212> TYPE: DNA
<213> ORGANISM: Artificial Sequence
<220> FEATURE:
<223> OTHER INFORMATION: synthetic

<400> SEQUENCE: 23
tgctgcccac atacgtgag                                        19

<210> SEQ ID NO 24
<211> LENGTH: 21
<212> TYPE: DNA
<213> ORGANISM: Artificial Sequence
<220> FEATURE:
<223> OTHER INFORMATION: synthetic

<400> SEQUENCE: 24
gcctgtcagt gttacccaca a                                     21

-continued

```
<210> SEQ ID NO 25
<211> LENGTH: 20
<212> TYPE: DNA
<213> ORGANISM: Artificial Sequence
<220> FEATURE:
<223> OTHER INFORMATION: synthetic

<400> SEQUENCE: 25
tcccatccac gcagtttgac                                               20

<210> SEQ ID NO 26
<211> LENGTH: 23
<212> TYPE: DNA
<213> ORGANISM: Artificial Sequence
<220> FEATURE:
<223> OTHER INFORMATION: synthetic

<400> SEQUENCE: 26
tcctcatcgt ttagcagttt tgt                                           23

<210> SEQ ID NO 27
<211> LENGTH: 23
<212> TYPE: DNA
<213> ORGANISM: Artificial Sequence
<220> FEATURE:
<223> OTHER INFORMATION: synthetic

<400> SEQUENCE: 27
gatgccaggc tgtgaaattt act                                           23

<210> SEQ ID NO 28
<211> LENGTH: 20
<212> TYPE: DNA
<213> ORGANISM: Artificial Sequence
<220> FEATURE:
<223> OTHER INFORMATION: synthetic

<400> SEQUENCE: 28
ctgttgcgaa tcccttggat                                               20

<210> SEQ ID NO 29
<211> LENGTH: 24
<212> TYPE: DNA
<213> ORGANISM: Artificial Sequence
<220> FEATURE:
<223> OTHER INFORMATION: synthetic

<400> SEQUENCE: 29
gtctacatgt tccagtatga ctcc                                          24

<210> SEQ ID NO 30
<211> LENGTH: 25
<212> TYPE: DNA
<213> ORGANISM: Artificial Sequence
<220> FEATURE:
<223> OTHER INFORMATION: synthetic

<400> SEQUENCE: 30
agtgagttgt catatttctc gtggt                                         25
```

COMPOSITION OF MATTER AND METHODS FOR ALTERATION OF DENDRITIC CELL METABOLISM TO AUGMENT CANCER VACCINE EFFICACY

CROSS-REFERENCES TO RELATED APPLICATIONS

This application claims priority to U.S. Provisional Application No. 62/299,224 filed on Feb. 24, 2016, which is incorporated by reference in its entirety.

STATEMENT REGARDING FEDERALLY SPONSORED RESEARCH

N/A

SEQUENCE LISTING

The application includes the sequence listing that is concurrently filed in computer readable form. This sequence listing is incorporated by reference herein. The following shRNA sequence is effective for silencing the expression of mouse CPT1a: CCGGGCTATGGTGTTTCCTACAT-TACTCGAGTAATGTAGGAAACACCATAGCTTTTTG (SEQ ID NO:1). Other sequences not listed are those in standard plasmids necessary for the generation of the lentiviral vector needed to deliver the above shRNA sequence to DCs.

BACKGROUND OF THE INVENTION

1. Field of the Invention

This invention relates to compositions of matter and methods for augmenting cancer vaccine efficacy.

2. Description of the Related Art

Significant advances have been made with the recent development of anti-CLTA-4 and anti-PD-1 monoclonal antibody (mAb) checkpoint inhibitors. However, many patients continue to fail these immunotherapy agents. It is generally recognized that immunotherapy failure involves the development of various tumor-mediated immune resistance mechanisms and more recent studies have described a subset of functionally tolerized dendritic cells (DCs) that contribute to the progression of several pre-clinical tumor models.

While significant strides have recently been made in cancer immunotherapy, the majority of our advanced cancer patients remain refractory to this treatment approach. An emerging literature is describing active immune evasion mechanisms by which malignancies manipulate their microenvironment in order to avoid detection and destruction by the adaptive immune response (Gajewski et al., 2006; Mellor and Munn, 2008). The dendritic cell (DC) is now recognized as a key player in the generation of anti-tumor immunity. By processing and presenting antigen, the individual DC induces the activation and modulates the functionality of a larger population of naïve T cells (Banchereau and Steinman, 1998). Given its central role in the priming of T cells to a developing malignancy, it is reasonable to conclude that cancers may evolve efficient and particularly potent mechanisms of immune evasion by targeting DC function. Studies have recently described DCs within the tumor microenvironment as contributing to tumor pathogenesis, suggesting that these antigen presenting cell populations undergo a tolerization program allowing them to generate an immune privileged microenvironment (Hanks et al., 2013; Scarlett et al., 2012). However, the mechanisms by which cancers induce this DC tolerization program have been largely unknown. An improved understanding of immune evasion including the process of DC tolerization promises to provide critical insight into novel mechanisms of immunotherapy resistance and the identity of previously unappreciated immunotherapeutic targets.

Accordingly, a need exists for compositions of matter and methods that overcome the failure of these immunotherapy agents. Further, a need exists for compositions of matter and methods that inhibit the development of the various tumor-mediated immune resistance mechanisms, and more specifically, the subset of functionally tolerized DCs.

SUMMARY OF THE INVENTION

This disclosure provides compositions of matter and methods, as described in the specification and claims herein.

These and other features, aspects, and advantages of the present invention will become better understood upon consideration of the following detailed description, drawings and appended claims.

In one embodiment, the disclosure provides a method of treating cancer in a patient, the method comprising: a) initiating a dendritic cell-based cancer vaccine treatment in the patient; and b) inhibiting fatty acid oxidation in dendritic cells of the dendritic cell-based cancer vaccine treatment. In some aspects, the dendritic cells are ex vivo vaccine-activated dendritic cells and step a) includes administering a therapeutically effective amount of the ex vivo vaccine-activated dendritic cells to the patient. In further aspects, the step b) may include genetically altering the ex vivo vaccine-activated dendritic cells to substantially silence expression of a fatty acid oxidation promoter. In other aspects, the dendritic cells are in vivo vaccine-activated dendritic cells and step a) includes administering a therapeutically effective amount of a vector configured to convert native dendritic cells into the in vivo vaccine-activated dendritic cells.

In another aspect, the disclosure provides a method of restoring dendritic cell function to a patient having a cancer that suppresses dendritic cell function, the method comprising inhibiting fatty acid oxidation in dendritic cells of the patient.

In another aspect, the disclosure provides a kit comprising: a vector configured to convert a dendritic cell into a vaccine-activated dendritic cell in vivo; and an inhibitor of a promoter of fatty acid oxidation in the dendritic cell.

In a further aspect, the disclosure provides a kit comprising a first vector configured to convert a dendritic cell into a vaccine-activated dendritic cell in vivo; and a transfection or transduction agent configured to transfect or transduce the dendritic cell or the vaccine-activated dendritic cell with genetic material that reduces expression of a promoter of fatty acid oxidation.

In another aspect, a composition of matter is provided. The composition of matter comprises a vaccine-activated dendritic cell that has been genetically programmed to substantially silence expression of at least one promoter of fatty acid oxidation.

In yet a further aspect, a composition of matter comprising: a therapeutically effective amount of an inhibitor of fatty acid oxidation in a dendritic cell; and a pharmaceutically acceptable carrier is provided. In some aspects, the inhibitor of fatty acid oxidation is an inhibitor of expression of part of the paracrine Wnt-β-catenin signaling pathway. In further aspects, the inhibitor of fatty acid oxidation is a CPT1a, CPT1b, or CPT1c inhibitor.

BRIEF DESCRIPTION OF THE DRAWINGS

The patent or application file contains at least one drawing executed in color. Copies of this patent or patent application publication with color drawing(s) will be provided by the Office upon request and payment of the necessary fee.

FIG. 1A depicts a schematic of previously characterized DC signaling pathway.

FIG. 1B is a graph demonstrating genetically silencing Wnt5a expression by the $BRAF^{V600E}PTEN^{-/-}$ melanoma cell line sensitizes this tumor model to anti-CTLA-4 antibody therapy. NTC, non-targeted control. Melanoma-derived Wnt5a Promotes DC Tolerization and Resistance to anti-CTLA-4 antibody Immunotherapy.

FIG. 1C depicts human melanoma Wnt5a expression correlates with response to anti-CTLA-4 antibody therapy. PD, progressive disease. CR, complete response.

FIG. 2A is a graph showing Wnt5a suppresses LPS-induced DC glycolysis. ECAR, extra-cellular acidification rate.

FIG. 2B is a bar graph showing Wnt5a promotes DC OXPHOS. OCR, oxygen consumption rate. UT, untreated.

FIG. 2C demonstrates tumor-infiltrating DCs (TIDCs) isolated from $BRAF^{V600E}PTEN^{-/-}$ melanoma genetically silenced for Wnt5a (red, bottom mouse and squares in graph on right) exhibit reduced levels of OXPHOS.

FIG. 6A is a graph depicting CPT1a is the dominant CPT1 isoform expressed in DCs.

FIG. 6B is a graph depicting Qrt-PCR analysis of CPT1a in the DC2.4 cell line following transduction with a CPT1a-targeted shRNA-expressing lentiviral vector.

FIG. 6C is a Western blot analysis of CPT1a in the DC2.4 cell line following transduction with a CPT1a-targeted shRNA-expressing lentiviral vector.

FIG. 6D is a graph demonstrating genetically silencing CPT1a reverses Wnt5a-induced DC-mediated Treg differentiation in vivo. $CPT1a^{KD}$ DCs were delivered to FoxP3-dsRed reporter mice by intra-dermal footpad injection and ipsilateral inguinal and popliteal LNs were resected for Treg quantitation by flow cytometry.

FIG. 6E is a graph demonstrating genetically silencing CPT1a in DCs potently induces $K^bOVA_{257-264}$-specific $CD8^+$ T cell proliferation. Cell Violet-stained OT-1 $CD8^+$ T cells were co-cultured with NTC-DCs vs $CPT1a^{KD}$ DCs and a dilutional flow cytometry assay was performed.

FIG. 10C shows flow cytometry results of BMDCs treated with 2-DG or Oligo then co-incubated with naïve $CD4^+$ T cells. $CD4^+$ $FoxP3^+$ Tregs measured by flow cytometry. n=3. right, Representative flow cytometry dot plot of $CD4^+$ $FoxP3^+$ Treg analysis.

FIG. 10D is a schematic of experimental approach for 10E. TIDCs were purified and injected into the foot pads of Foxp3-mRFP mice; inguinal lymph nodes were isolated and analyzed for Tregs by flow cytometry.

FIG. 10E is a bar graph showing draining lymph node Treg analysis following delivery of TIDCs isolated from $BRAF^{V600E}PTEN^{-/-}$-NTC and $BRAF^{V600E}PTEN^{-/-}$-$Wnt5a^{KD}$ melanomas. n=4/group.

FIG. 10F is a schematic illustrating the dynamic spectrum of DC-induced T cell responses based on metabolic alteration. All data is mean+/−S.D. *P<0.05.

FIG. 11A shows Wnt5a promotes Treg differentiation by driving DC fatty acid oxidation. DC uptake of fluorescent dodecanoic acid fatty acid substrate, TF2-C12, measured by flow cytometry after treatment with Wnt5a or vehicle control (UT). n=3.

FIG. 11B shows DC intracellular lipid content following Wnt5a treatment vs UT. BODIPY, fluorescent lipid probe. n=3. right, Microscopic immunofluorescence analysis of BODIPY-stained DC2.4-β-cat$^{KD}$ and DC2.4-NTC cell lines (40×). n=3. green, BODIPY.

FIG. 11C shows BMDCs pre-treated with Wnt5a vs Wnt5a+ETO prior to OCR analysis.

FIG. 11D shows metabolic parameter calculations based on 11C. n=6.

FIG. 11E shows in vitro Treg assay measuring DC-induced CD4$^+$ FoxP3$^+$ Tregs under the indicated conditions. n=3.

FIG. 11F shows in vivo Treg assay measuring DC-induced CD4$^+$ FoxP3$^+$ Tregs following treatment with either Wnt5a or Wnt5a+ETO. n=4/group.

FIG. 11G shows BMDCs pulsed with OVA257-264 peptide, treated with ETO or stimulated with LPS, and co-incubated with OT-1 splenocytes. CD8$^+$ T cell proliferation measured by CellTrace Violet dilution. n=3.

FIG. 11H shows DC2.4-NTC or DC2.4-CPT1A$^{KD}$ DC lines were treated with Wnt5a, injected into the left foot pads of Foxp3-mRFP mice. Left inguinal lymph nodes were isolated and subjected to flow cytometry analysis of Tregs. n=3/group.

FIG. 11I shows DC2.4-NTC or DC2.4-CPT1A$^{KD}$ DC lines were loaded with SIINFEKL peptide, treated with Wnt5a or stimulated with LPS, and co-incubated with OT-1 splenocytes. CD8$^+$ T cell proliferation measured by CellTrace Violet dilution flow cytometry. n=3. All data is mean+/−S.D. *P<0.05. See also FIGS. 17,18.

FIG. 12A is a heatmap showing BMDCs treated with Wnt5a for 48 hours and analyzed by PCR array. Heatmap differential gene expression analysis: "F", genes involved in fatty acid metabolism, "L", genes involved in lipid transport, "A", genes involved in adipogenesis. red, high expression. green, low expression. n=3.

FIG. 12B shows BMDCs treated with Wnt5a. PPARγ mRNA levels measured by qRT-PCR. n=3.

FIG. 12C shows BMDCs treated with Wnt5a. CPT1A mRNA levels measured by qRT-PCR. n=3.

FIG. 12D shows PPARγ and CPT1A Western blot analysis following human monocyte-derived DC treatment with Wnt5a. n=3.

FIG. 12E shows CPT1A qrt-PCR analysis of DC2.4-NTC and DC2.4-O-cat' cell lines. n=3.

FIG. 12F shows qrt-PCR analysis of PPARγ and CPT1A expression by BMDCs treated with either the GSK3β inhibitor, Bio, vs its control, MeBio. n=3.

FIG. 13E shows hemin colorimetric assay of DCs treated with increasing concentrations of Wnt5a+/−ETO. n=3.

FIG. 13F shows qrt-PCR analysis of ALAS1 expression by DCs following the indicated treatments. n=3.

FIG. 13G shows qrt-PCR analysis of heme synthetic enzymes in DCs treated with Wnt5a. red, upregulated enzymes. n=3. All data is mean+/−S.D. *1$^3$<0.05. See also FIG. 22.

FIG. 14E shows qrt-PCR analysis of IL-6, IL-12p40 mRNA levels in UT or ETO-treated BMDCs. n=3.

FIG. 14F shows qrt-PCR analysis of IL-6, IL-12p40 mRNA levels in BMDCs following treatment with Wnt5a.

FIG. 14G shows qrt-PCR analysis of IL-6, IL-12p40 cytokine expression by TIDCs purified from BRAF$^{V600E}$PTEN$^{-/-}$-NTC or -Wnt5a$^{KD}$ melanomas. n=3/group. All data is mean+/−S.D. *P<0.05. See also FIG. 18.

FIG. 20A shows ECAR analysis of DCs untreated (UT) or pre-treated with the β-catenin inhibitor, XAV939.

FIG. 20B shows qrt-PCR analysis of β-catenin expression in the DC2.4-NTC control cell line and DC2.4-β-catKD cell line.

FIG. 20C shows Western blot confirmation of β-catenin knockdown in the DC2.4-β-catKD cell line.

FIG. 20D shows intracellular and extracellular lactate levels were measured in both the DC2.4-NTC and DC2.4-β-catKD cell lines. NTC, non-targeted control. KD, knockdown.

FIG. 21A shows qrt-PCR analysis of PPARγ and CPT1A expression by Wnt3a-stimulated DCs. UT, untreated.

FIG. 21B shows PpIX flow cytometry analysis of Wnt3a- and Wnt5a-stimulated DCs. Cells were treated with either Wnt5a or Wnt3a for 48 hours followed by a 4 hour incubation with 1 mM δ-ALA then subjected to flow cytometry analysis of intracellular PpIX.

FIG. 21C shows qrt-PCR analysis of heme synthesis enzymes by Wnt3a-stimulated DCs. All data is mean±SD. n=3. * p<0.05

DETAILED DESCRIPTION OF THE INVENTION

Figure 3A:
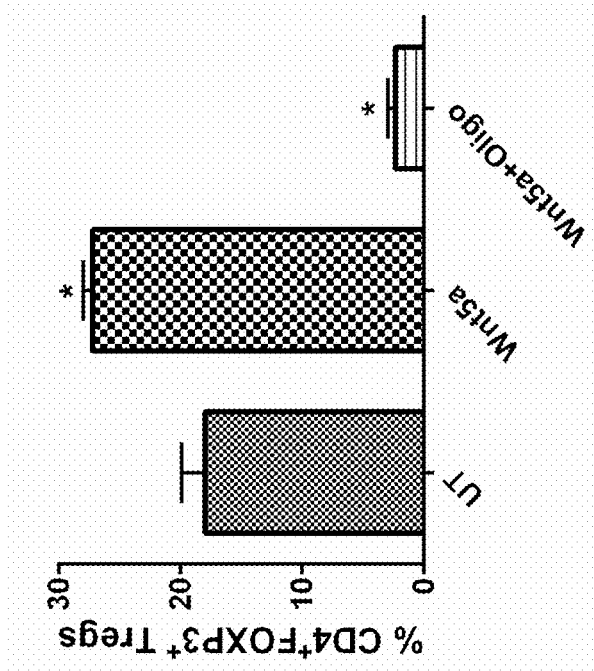
FIG. 3A demonstrates alteration of Metabolic Pathways Directly Impacts DC-mediated Treg Differentiation. Inhibition of glycolysis promotes DC-mediated Treg development.

Before the present invention is described in further detail, it is to be understood that the invention is not limited to the particular embodiments described. It is also to be understood that the terminology used herein is for the purpose of describing particular embodiments only, and is not intended to be limiting. The scope of the present invention will be limited only by the claims. As used herein, the singular forms "a", "an", and "the" include plural embodiments unless the context clearly dictates otherwise.

It should be apparent to those skilled in the art that many additional modifications beside those already described are possible without departing from the inventive concepts. In interpreting this disclosure, all terms should be interpreted in the broadest possible manner consistent with the context. Variations of the term "comprising" should be interpreted as referring to elements, components, or steps in a non-exclusive manner, so the referenced elements, components, or steps may be combined with other elements, components, or steps that are not expressly referenced. Embodiments referenced as "comprising" certain elements are also contemplated as "consisting essentially of" and "consisting of" those elements. In places where ranges of values are given, this disclosure explicitly contemplates other combinations of the lower and upper limits of those ranges that are not explicitly recited. For example, recitation of a value between 1 and 10 or between 2 and 9 also contemplates a value between 1 and 9 or between 2 and 10. Ranges identified as being "between" two values are inclusive of the end-point values. For example, recitation of a value between 1 and 10 includes the values 1 and 10.

Aspects of the present disclosure that are described with respect to methods can be utilized in the context of the compositions of matter or kits discussed in this disclosure. Similarly, aspects of the present disclosure that are described with respect to compositions of matter can be utilized in the context of the methods and kits, and aspects of the present disclosure that are described with respect to kits can be utilized in the context of the methods and compositions of matter.

The methods, compositions, and kits of the present disclosure are based, at least in part, on a surprising discovery by the inventors regarding a fundamental biochemical signaling pathway that drives dendritic cell tolerization. While other studies have previously demonstrated that enhanced levels of glycolysis are necessary for DC-mediated antigen-presentation and T cell activation, the inventors surprisingly discovered that paracrine Wnt-β-catenin signaling within the melanoma microenvironment reprograms DC metabolism by shifting the preferred energy source from glycolysis to fatty acid oxidation, a process required for DC-dependent differentiation of regulatory T cells (Tregs) and one that is likely to be amplified within the glucose-starved tumor microenvironment.

The inventors further identified that the paracrine Wnt-β-catenin signaling pathway involves upregulation of the mitochondrial fatty acid transporter, CPT1a. The results presented herein demonstrate that pharmacologic inhibition of CPT1a potently inhibits DC-mediated Treg development while promoting antigen-specific T cell activation.

The paracrine Wnt-β-catenin signaling pathway induces downstream expression of the indoleamine 2,3-dioxygenase-1 (IDO) immunoregulatory enzyme, which is required for the differentiation of Tregs and the generation of an immunotolerant microenvironment. Illustrating the importance of this pathway in immune checkpoint inhibitor resistance, the inventors have demonstrated pharmacologic blockade of Wnt5a release and genetic silencing of Wnt5a melanoma expression to synergistically enhance the efficacy of the anti-CTLA-4 mAb in a murine melanoma model. Using RNAseq differential gene expression analysis, the inventors also determined that the Wnt-β-catenin signaling pathway is significantly upregulated in autochthonous melanoma tissues progressing through anti-PD-1 mAb therapy, further implicating this pathway in immunotherapy resistance. Additional findings show that the ability of the Wnt-β-catenin to induce DC IDO-mediated Treg generation and promote tumor progression is fundamentally dependent upon shifting DC energy metabolism from glycolysis to fatty acid oxidation.

Definitions and Abbreviations

The terms "subject" and "patient" are used interchangeably and refer to any animal (e.g., a mammal), including, but not limited to, humans, non-human primates, rodents, and the like, which is to be the recipient of a particular treatment. Typically, the terms "subject" and "patient" are used interchangeably herein in reference to a human subject.

The terms "cancer" and "cancerous" refer to or describe the physiological condition in mammals in which a population of cells are characterized by unregulated cell growth. A cancer may be a non-solid tumor type or a solid tumor. Examples of cancer include, but are not limited to, carcinoma, lymphoma, blastoma, sarcoma, and leukemia. More particular examples of such cancers include squamous cell cancer, small-cell lung cancer, non-small cell lung cancer, adenocarcinoma of the lung, squamous carcinoma of the lung, cancer of the peritoneum, hepatocellular cancer, gastrointestinal cancer, pancreatic cancer, glioblastoma, cervical cancer, ovarian cancer, liver cancer, bladder cancer, hepatoma, breast cancer, colon cancer, colorectal cancer, endometrial or uterine carcinoma, salivary gland carcinoma, kidney cancer, liver cancer, prostate cancer, vulval cancer, thyroid cancer, hepatic carcinoma and various types of head and neck cancer.

The term "subject suffering from cancer" refers to a subject that presents one or more symptoms indicative of a cancer (e.g., a noticeable lump or mass) or has been diagnosed as having cancer.

The terms "effective amount" or "therapeutically effective amount" refer to an amount sufficient to effect beneficial or desirable biological and/or clinical results.

The term "dendritic cell-based cancer vaccine" refers to a cancer vaccine that utilizes dendritic cells to promote an immune response to cancer cells in the body of a patient.

The term "vaccine-activated dendritic cell" refers to a dendritic cell that has been activated for use in a dendritic cell-based cancer vaccine.

The term "ex vivo vaccine-activated dendritic cell" refers to a dendritic cell that has been activated outside of the patient and which can be administered to the patient to initiate a dendritic cell-based cancer vaccine.

The term "in vivo vaccine-activated dendritic cell" refers to a dendritic cell that has been activated inside of the patient. An example of an in vivo vaccine-activated dendritic cell is a dendritic cell that has been transfected or transduced by genetic material that initiates expression of a cancer-related antigen.

The abbreviation "DC(s)" refers to dendritic cell(s).

The abbreviation "CPT1a" refers to carnitine palmitoyl transferase 1A (liver).

The abbreviation "CPT1b" refers to carnitine palmitoyl transferase 1B (liver).

The abbreviation "CPT1c" refers to carnitine palmitoyl transferase 1C (liver).

The abbreviation "Treg(s)" refers to regulatory T cell(s).

The term "treat," "treating" or "treatment" of cancer encompasses, but is not limited to, reducing, inhibiting or preventing the growth of cancer cells, reducing, inhibiting or preventing metastasis of the cancer cells or invasiveness of the cancer cells or metastasis or reducing, inhibiting or preventing one or more symptoms of the cancer or metastasis thereof.

Methods

This disclosure provides a method of treating cancer in a patient. This disclosure also provides a method of restoring dendritic cell function to a patient having a cancer that suppresses dendritic cell function. Aspects of the disclosure described with respect to the former method can be applicable to the latter method, and vice versa, unless the context clearly dictates otherwise.

The methods disclosed herein can include diagnosing a patient as having cancer. The methods disclosed herein can include a conventional treatment regimen, which can be altered to include the steps of the methods described herein. The methods disclosed herein can include monitoring the patient to determine efficacy of treatment and further modifying the treatment in response to the monitoring. The methods disclosed herein can include administering a therapeutically effective amount of a checkpoint inhibitor.

The method of treating cancer in a patient can include one or more of the following steps: a) initiating a dendritic cell-based cancer vaccine treatment in the patient; and b) inhibiting fatty acid oxidation in dendritic cells of the dendritic cell-based cancer vaccine treatment.

Dendritic cell-based cancer vaccines can be generated either in an ex vivo or in vivo manner. Ex vivo generation of dendritic cell vaccines involves the isolation and antigen loading of dendritic cells followed by their maturation/activation prior to their delivery to the tumor-bearing host. In vivo or in situ dendritic cell-based vaccines involves the dendritic cell-directed delivery of antigen followed by the delivery of a dendritic cell-targeted activation stimulus. The dendritic cell-based vaccine approaches are currently in development for the management of patients with advanced cancers including those that have undergone previous surgical resection of a cancer but are at high risk of cancer recurrence (adjuvant setting). General methods relating to dendritic cell-based cancer vaccines can be found in the following references, which are hereby incorporated by reference herein: Dannull et al., J Clin Invest. 2013; 126(7): 3135-3145; Tacken et al., Nature Reviews: Immunology October 2007; Vol. 7, pp. 790-802; Feuerstein et al., J Immunol Methods 245 (2000) pp. 15-29; Banchereau et al., Cell, Vol. 106, pp. 271-274 (Aug. 10, 2001); and He et al., J Immunol 2005; 174:3808-3817.

In certain aspects, the dendritic cells can be ex vivo vaccine-activated dendritic cells. In these cases, the initiating a dendritic cell-based cancer vaccine treatment in the patient of step a) can include administering a therapeutically effective amount of the ex vivo vaccine-activated dendritic cells to the patient. Moreover, in these cases, the inhibiting fatty acid oxidation in dendritic cells of the dendritic cell-based cancer vaccine treatment of step b) can include genetically altering the ex vivo vaccine-activated dendritic cells to substantially silence expression of a fatty acid oxidation promoter.

In certain aspects, the dendritic cells can be in vivo vaccine-activated dendritic cells. In these cases, the initiating a dendritic cell-based cancer vaccine treatment in the patient of step a) can include administering a therapeutically effective amount of a vector configured to convert native dendritic cells into the in vivo vaccine-activated dendritic cells. Moreover, in these cases, the inhibiting fatty acid oxidation in dendritic cells of the dendritic cell-based cancer vaccine treatment of step b) can include administering to the patient a therapeutically effective amount of an inhibitor of a promoter of fatty acid oxidation in the in vivo vaccine-activated dendritic cells. In addition, in these cases, the inhibiting fatty acid oxidation in dendritic cells of the dendritic cell-based cancer vaccine treatment of step b) can include administering to the patient a therapeutically effective amount of a transfection or transduction agent configured to transfect or transduce the native dendritic cells or the in vivo vaccine-activated dendritic cells with genetic material that reduces expression of a promoter of fatty acid oxidation.

The method of restoring dendritic cell function to a patient having a cancer that suppresses dendritic cell function can include inhibiting fatty acid oxidation in dendritic cells of the patient. The inhibiting fatty acid oxidation can include administering to the patient a therapeutically effective amount of an inhibitor of a promoter of fatty acid oxidation in the dendritic cells. The inhibiting fatty acid oxidation can include administering to the patient a therapeutically effective amount of a transfection or transduction agent configured to transfect or transduce the dendritic cells with genetic material that reduces expression of a promoter of fatty acid oxidation.

By "restoring dendritic cell function" the term encompasses the ability of the dendritic cells to activate an antigen-specific immune response. In some aspects, the term encompasses the ability of dendritic cells to activate memory and/or naive T cells, including CD8+ T cells, CD4+ helper T cells and/or activate B cells. In other terms, the restoring dendritic cell function signals a shift from the expansion of Tregs to effector T cells.

The term "antigen" as used herein encompasses antigens that are expressed specifically on a tumor cell found in the subject. Suitable tumor antigens are known in the art and may be specific to the specific type of tumor or specific patient being treated. Suitable tumor antigens include, but are not limited to, for example, p100/pmel, NY-ESO1, MAGE, MELAN-A/MART-1, TRP1, TRP2, Tyrosinase, MUC1, CEA, AFP, RAGE-1, HER2/NEU, WT1, PSA, PSMA, and CA-125, among others. This list is not exhaustive and one skilled in the art would readily be able to identify tumor antigens to be used in the present invention. Suitably, the tumor antigens would be pulsed and loaded onto dendritic cells DCs) by methods known in the art.

In certain aspects, the fatty acid oxidation promoter or the promoter of fatty acid oxidation can be part of the paracrine Wnt-β-catenin signaling pathway, the β-catenin-PPARγ signaling pathway, the β-catenin-PPARγ-CPT1a signaling pathway, or a combination thereof. In certain aspects, the fatty acid oxidation promoter can be CPT1a, CPT1b, or CPT1c. The fatty acid oxidation promoter or the promoter of fatty acid oxidation can be any blockade of any or all soluble Wnt ligands.

In certain aspects, an inhibitor of the fatty acid oxidation promoter or an inhibitor of the promoter of fatty acid oxidation can be selected from the group consisting of Etomoxir, TGDA, POCA, Aminocarnitine, Palitoylcarnitine, ST1326, ST2425, ST2452, Ranolazine, Propanolol, and combinations thereof.

In aspects of the methods involving administering a therapeutically effective amount of a checkpoint inhibitor, the checkpoint inhibitor can be selected from the group consisting of anti-PD-1 antibodies (e.g., pembrolizumab, nivolumab), anti-CTLA-4 antibodies (e.g., ipilimumab), combination anti-PD-1 antibody and anti-CTLA-4 antibody, anti-PD-L1 antibodies, and the like.

The term "substantially silence expression" of a fatty acid oxidation promoter encompasses at least a 50%-100% reduction in the expression of a fatty acid oxidation promoter, more suitably at least a 60% reduction in the expression of a fatty acid oxidation promoter, alternatively at least a 65% reduction in the expression of a fatty acid oxidation promoter, alternatively at least 70% reduction in the expression of a fatty acid oxidation promoter, alternatively at least a 75% reduction in the expression of a fatty acid oxidation promoter, alternatively at least a 80% reduction in the expression of a fatty acid oxidation promoter, alternatively at least a 85% reduction in the expression of a fatty acid oxidation promoter, alternatively at least about 90% reduction in the expression of a fatty acid oxidation promoter.

Compositions of Matter

This disclosure provides compositions of matter. The compositions of matter can be suitable for use in the methods described herein.

The composition of matter can include a vaccine-activated dendritic cell that has been genetically programmed to substantially silence expression of at least one promoter of fatty acid oxidation Suitable compositions, kits and methods to genetically substantially silence expression of the at least one promoter are known in the art, and include, but are not limited to transduction by a virus or viral vector (e.g. adenoviruses, retroviruses including lentiviruses) transfection using a plasmid or vector, siRNA, shRNA, and the like. Suitable methods of delivering siRNA and shRNA are known in the art, including transfection and transduction of the siRNA or shRNA. Suitably, vectors can be made that exogenously express the siRNA or shRNA once the vector is entered into the dendritic cell.

Ex vivo dendritic cell-based cancer vaccine treatment protocol can be generally summarized as follows. Peripheral blood mononuclear cells are collected by standard leukopharesis and monocytes are purified using anti-CD14 antibody-coated beads and a magnetic column. Purified monocytes are differentiated into dendritic cells in vitro in the presence of GM-CSF/IL-4. DC purity will be checked by flow cytometry. These DCs are pulsed or transfected with antigen and transduced with a lentiviral vector to genetically silence the CPT1 target. Other approaches to suppress CPT1 expression including siRNA transfection may also be incorporated. The resulting DC-base vaccine is cryopreserved for future administration. Following thawing, the DCs are counted, their viability is determined, and endotoxin levels are measured. Those DC aliquots that meet specifications including a viability>70%, and an endotoxin level<5 EU/kg will be administered to human subjects using 4 separate intra-dermal 200 ul injections ($2.5 \times 10^6$ DCs per injection) for a total dose of $1.0 \times 10^7$ DCs per vaccination. In one aspect, a total of six weekly vaccinations are administered. Various vaccine schedules will be assessed. Suitable vaccine schedules may include at least two to twelve vaccinations, suitably at least six to ten vaccinations.

The composition of matter can include a transduction or transfection agent configured to inhibit CPT1 expression by in situ dendritic cell populations by targeted-nanoparticle delivery of siRNA or by targeted shRNA-expressing lentiviral transduction.

The composition of matter can include a therapeutically effective amount of an inhibitor of fatty acid oxidation in a dendritic cell and a pharmaceutically acceptable carrier. These inhibitors are useful for pharmacological methods of inhibiting the activity of dendritic cell CPT1.

In some aspects, the inhibitor of fatty acid oxidation is an inhibitor of expression of part of the paracrine Wnt-β-catenin signaling pathway. In further aspects, the inhibitor of fatty acid oxidation is a CPT1a, CPT1b, or CPT1c inhibitor The composition can include a pharmaceutically acceptable carrier. The composition can also include any other components known to a person having ordinary skill in the art to be useful in compositions of matter useful for the treatments described herein.

The term "pharmaceutically acceptable carrier" refers any carrier, diluent or excipient that is compatible with the other ingredients of the formulation and not deleterious to the recipient. A pharmaceutically acceptable carrier can be selected on the basis of the selected route of administration and standard pharmaceutical practice. The active agent may be formulated into dosage forms according to standard practices in the field of pharmaceutical preparations. See Alphonso Gennaro, ed., *Remington's Pharmaceutical Sciences,* 18th Ed., (1990) Mack Publishing Co., Easton, Pa.

Suitable dosage forms may comprise, for example, tablets, capsules, solutions, parenteral solutions, injectable solutions, troches, suppositories, or suspensions. For antibodies, suitable dosages forms are normally solutions.

For oral administration, the active ingredient may be combined with one or more solid inactive ingredients for the preparation of tablets, capsules, pills, powders, granules or other suitable oral dosage forms. For example, the active agent may be combined with at least one excipient such as fillers, binders, humectants, disintegrating agents, solution retarders, absorption accelerators, wetting agents absorbents or lubricating agents.

For parenteral administration, the active agent may be mixed with a suitable carrier or diluent such as water, an oil (e.g., a vegetable oil), ethanol, saline solution (e, g., phosphate buffer saline or saline), aqueous dextrose (glucose) and related sugar solutions, glycerol, or a glycol such as propylene glycol or polyethylene glycol, or a carrier that is suitable for maintaining the viability of the dendritic cells. Stabilizing agents, antioxidant agents and preservatives may also be added. Suitable antioxidant agents include sulfite, ascorbic acid, citric acid and its salts, and sodium EDTA. Suitable preservatives include benzalkonium chloride, methyl- or propyl-paraben, and chlorbutanol. The composition for parenteral administration may take the form of an aqueous or nonaqueous solution, dispersion, suspension or emulsion.

The pharmaceutical composition is preferably in unit dosage form. In such form the preparation is divided into unit doses containing appropriate quantities of the active component.

Kits

This disclosure provides kits. The kits can be suitable for use in the methods described herein.

In one aspect, a kit can include a first vector configured to convert a dendritic cell into a vaccine-activated dendritic cell in vivo; and an inhibitor of fatty acid oxidation in the dendritic cell—or—a transfection or transduction agent configured to transfect or transduce the dendritic cell or the vaccine-activated dendritic cell with genetic material that reduced expression of a promoter of fatty acid oxidation.

In some aspects, the promoter of fatty acid oxidation in the dendritic cell is part of the paracrine Wnt-β-catenin signaling pathway. In some aspects, the promoter of fatty acid oxidation in the dendritic cell is CPT1a, CPT1b, or CPT1c.

In some aspects, the vector is a retroviral vector, in particular a lentiviral vector.

In another aspect, a kit comprises a first vector configured to convert a dendritic cell into a vaccine-activated dendritic cell in vivo; and a transfection or transduction agent configured to transfect or transduce the dendritic cell or the vaccine-activated dendritic cell with genetic material that reduces expression of a promoter of fatty acid oxidation.

The present invention has been described in terms of one or more preferred embodiments, and it should be appreciated that many equivalents, alternatives, variations, and modifications, aside from those expressly stated, are possible and within the scope of the invention.

The following non-limiting examples are included for purposes of illustration only, and are not intended to limit the scope of the range of techniques and protocols in which the compositions and methods of the present invention may find utility, as will be appreciated by one of skill in the art and can be readily implemented.

Example 1: Metabolic Re-Programming of Dendritic Cell-Based Cancer Vaccines to Enhance Anti-Tumor Immunity All references mentioned in the Examples and Specification are hereby incorporated by reference in their entirety.

Background.

Studies over the last 40 years have demonstrated the DC as being uniquely equipped to process and present antigen captured from the environment to stimulate naïve T cell activation. In addition to directing the clonal expansion of antigen-specific T cells, the DC is also capable of modulating the subsequent differentiation and phenotype of the activated effector T cell. This specialized ability makes the DC a central orchestrator of the anti-tumor immune response (1). Therefore, it is logical that these specialized antigen-presenting cells have been utilized as vectors for the development of cancer vaccines (2).

Despite their proficiency in reproducibly generating some level of tumor antigen-specific T cell response, their ability to generate clinically meaningful responses in advanced cancer patients remains largely unproven (3). It has now been well established that cancers evolve several mechanisms to evade detection and destruction by the host immune system and that these processes likely contribute to immunotherapy failure (4, 5). To date, little has been investigated regarding the impact of the tumor microenvironment on the function and viability of DC-based cancer vaccines. In particular, the ability of developing cancers to influence DC function in the tumor microenvironment by competing for their nutritional resources remains poorly explored (6). Further, it is unclear how alterations in the levels of these local metabolic substrates may affect DC function. The ability of developing cancers to actively tolerize local DC populations has only recently been recognized and many of the mechanisms involved in this re-programming process remain unknown (7-9). To date, the primary focus of investigation in this area has been on the immunoregulatory enzyme, indoleamine 2, 3-dioxygenase (IDO), which converts the essential amino acid tryptophan into the metabolic byproducts collectively known as the kynurenines. Earlier work in this field has shown IDO-expressing DCs to suppress cell proliferation (10-12). Later studies revealed kynurenine to promote the differentiation and activation of FoxP3+ regulatory T cell (Treg) populations both in vitro and in vivo (13-15). This was a breakthrough finding in light of the previously established role of Tregs in the maintenance of peripheral immune tolerance (16-18). Importantly, reports implicating IDO expression to be associated with poor clinical prognosis in several cancer types began to emerge. In particular, DC-dependent expression of IDO in the sentinel lymph nodes of patients with advanced melanoma was found to correlate with a poor clinical prognosis (19).

More recent work has highlighted the important role of cellular metabolism in the regulation of DC function. Indeed, a high glycolytic flux has been found to underpin the process of DC maturation, the genetic program necessary for effective antigen presentation and effector T cell activation (20, 21). In a reciprocal manner, studies have indicated that tolerogenic DCs display a metabolic signature consistent with enhanced oxidative phosphorylation (OXPHOS) (22).

Significance and Scientific Impact.

Checkpoint inhibitor development has generated promising clinical results, however this approach is inherently limited by its generalized activation of multiple T cell clones and non-specificity. Indeed, anti-CTLA-4 antibody: anti-PD-1 antibody combination therapy generates a high degree of grade 3/4 toxicities (>50%) leading to the discontinuation of this regimen in over 40% of patients (23). A vaccine approach is therefore necessary to direct the adaptive immune response of the host toward exclusive targeting of malignant tissue. This issue of toxicity is even more relevant when considering the treatment of cancer patients in the adjuvant setting. Furthermore, the development of effective prophylactic cancer vaccines requires this approach to have minimal side-effects—clearly not a treatment setting appropriate for currently available checkpoint inhibitor therapies. It follows that our ability to optimize DC-dependent effector T cell activation in immunosuppressive environments will therefore be important for advancing the field of cancer immunotherapy.

It should also be noted that the current strategies for immunotherapy development have remained almost exclusively focused on enhancing T cell activity while DCs which play a critical role in the activation and differentiation of tumor antigen-specific T cell populations have been relatively ignored. Emerging evidence indicates that the process of tumor-mediated DC tolerization is critical for cancer development and progression (24, 25).

Recent work has suggested that this process of DC tolerization may involve metabolic alterations which occur within the tumor microenvironment (6). It should be emphasized that the targeting of DC metabolism for augmenting cancer vaccine efficacy remains unexplored. Our work translates a recently deciphered mechanism describing the fundamental biochemical signals that drive DC tolerization into a more potent DC vaccine capable of circumventing the immunosuppressive environment generated by solid tumors. Given that our data indicates that DC FAO represents a central process involved in tumor-mediated immune tolerance, we are genetically targeting a key component of this biochemical pathway to augment the efficacy of DC-based cancer vaccines. Indeed, our data suggests that the inhibition of DC FAO has a more potent impact on the differentiation of Tregs than does IDO inhibition.

Preliminary Data.

We have determined that developing melanomas induce activation of the β-catenin pathway in local DCs via a Wnt5a-dependent paracrine signaling mechanism within the tumor microenvironment (26). Interestingly, we found this signaling pathway to induce the upregulation of the immunoregulatory enzyme, indoleamine 2, 3-dioxygenase-1 (IDO), and for this process to drive regulatory T cell differentiation and generate local immune tolerance (FIG. 1A). In a separate line of inquiry, we have applied RNAseq differential expression analysis to investigate the changes in gene expression observed in melanomas which have escaped anti-PD-1 antibody therapy in an autochthonous transgenic melanoma model that closely recapitulates human BRAFV600E mutant melanoma (27, 28). This study showed that a significant upregulation of the Wnt-β-catenin signaling pathway occurs in melanomas progressing through this form of immunotherapy suggesting that this pathway may play a role in checkpoint inhibitor resistance (data not shown). Using this same model system as well as human melanoma tissue specimens, we also determined elevated levels of Wnt5a expression to be associated with an inferior response to anti-CTLA-4 antibody immunotherapy (FIG. 1B, C). This data suggests that the Wnt5a-β-catenin pathway in DCs plays an important role in the development of immune tolerance and indicates that this signaling axis is capable of promoting immunotherapy resistance.

Figure 3B:
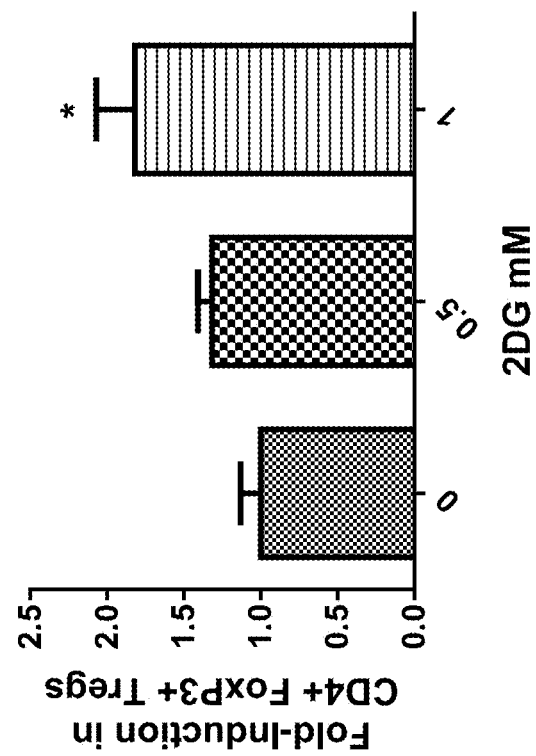
FIG. 3B demonstrates the inhibition of OXPHOS inhibits DC-mediated Treg development.
Figure 4B:
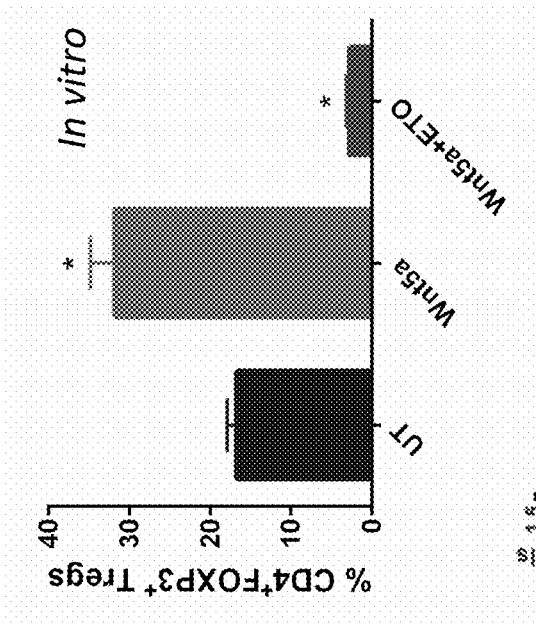
FIG. 4B demonstrates that ETO inhibits Wnt5a-conditioning of DC-mediated Treg development in vitro.
Figure 4A:
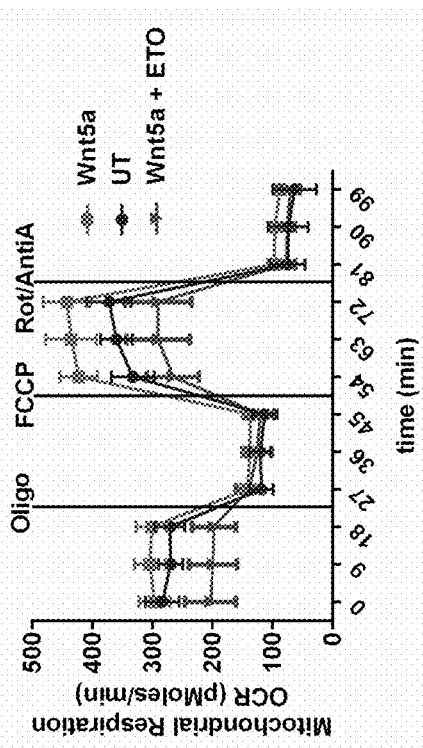
FIG. 4A demonstrates inhibition of FAO Reverses Wnt5a-induced DC OXPHOS and DC-mediated Treg Development. Inhibition of DC FAO abrogates Wnt5a-induced DC OXPHOS. ETO, etomoxir, inhibitor of CPT1a, a mitochondrial fatty acid transporter.
Figure 4D:
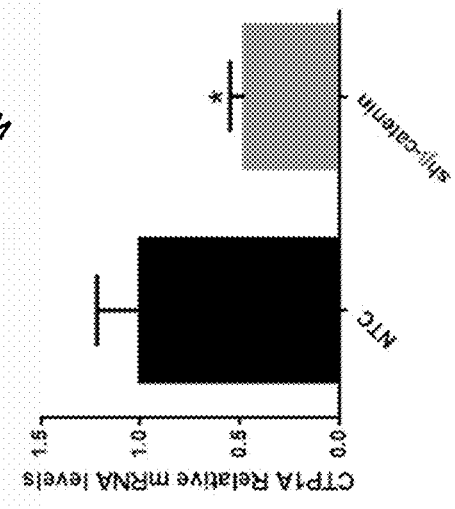
FIG. 4D demonstrates that genetic silencing of β-catenin in the DC2.4 cell line suppresses CPT1a expression based on qrt-PCR.
Figure 4C:
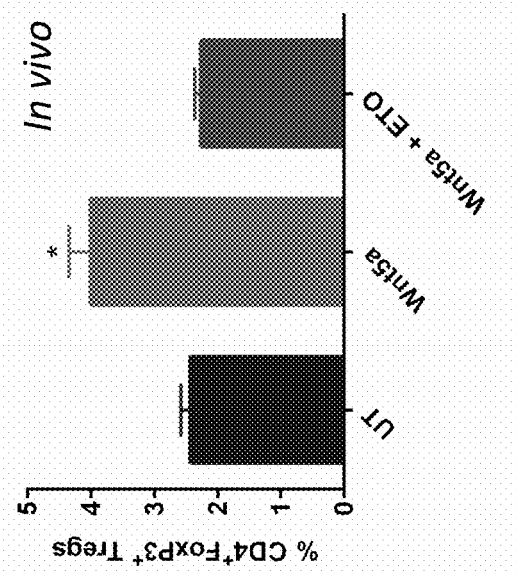
FIG. 4C demonstrates that ETO inhibits Wnt5a-conditioning of DC-mediated Treg development in vivo.
Figure 5B:
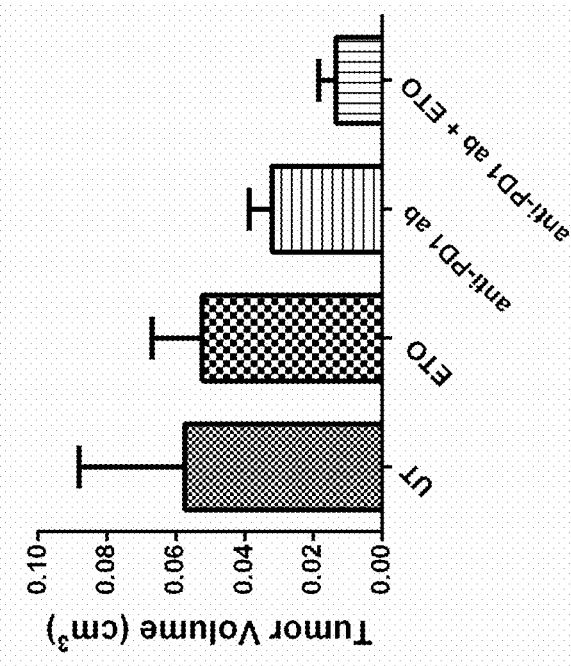
FIG. 5B demonstrates that ETO augments anti-PD-1 antibody suppression of $BRAF^{V600E}PTEN^{-/-}$ melanoma progression.
Figure 5A:
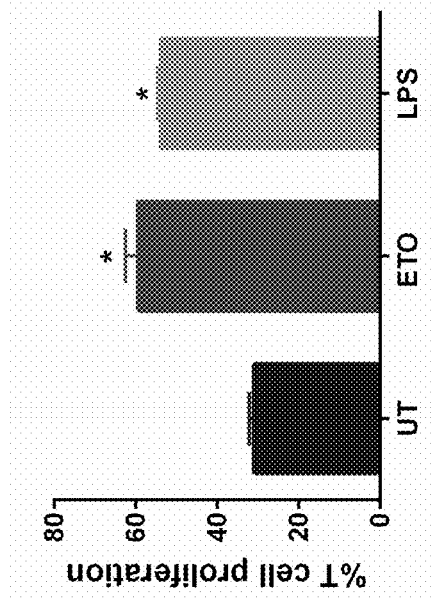
FIG. 5A demonstrates inhibition of FAO Augments DC-mediated T cell Activation and Augments the Ability of anti-PD-1 to Suppress $BRAF^{V600E}PTEN^{-/-}$ Melanoma Growth. ETO enhances the ability of DCs to induce OT-1 T cell proliferation after pulsing with the SIINFEKL peptide. LPS, lipopolysaccharide, positive control.

While conducting these studies, we also found Wnt3a to be capable of upregulating IDO expression, however it was noted that this ligand failed to license DCs to induce Treg expansion (26). Given that Wnt5a had been previously implicated in the regulation of metabolic pathways in other cell types, we hypothesized that the differential effect observed for Wnt5a was dependent upon its ability to modulate DC metabolism and that this alteration in DC metabolic pathways may impact the regulation of IDO enzyme activity (29). To address this hypothesis, we conducted experiments to determine the metabolic impact of Wnt5a on primary myeloid DCs in extracellular flux assays. This work demonstrated the Wnt5a ligand to inhibit LPS-mediated DC glycolysis while strongly promoting DC OXPHOS in vitro (FIG. 2A, B). It was further determined that Wnt5a was necessary for inducing a metabolic shift toward OXPHOS in local DCs within an in situ melanoma model (FIG. 2C). Subsequent experiments showed that the inhibition of DC glycolysis using 2-deoxyglucose (2-DG) resulted in the enhancement of DC-dependent Treg expansion while the inhibition of DC OXPHOS using oligomycin (Oligo) potently suppressed Wnt5a induction of DC-mediated Treg differentiation in vitro (FIG. 3). Additional studies also demonstrated that Wnt5a had no net effect on DC ATP generation, suggesting that the Wnt5a-β-catenin signaling pathway shifted DCs from glucose to utilization of a different carbon source (data not shown). This finding prompted us to investigate the impact of Wnt5a on DC FAO. Indeed, using the FAO inhibitor, etomoxir (ETO), we demonstrated FAO inhibition to ablate Wnt5a-induced DC OXPHOS as well as Wnt5a-stimulated DC-mediated Treg generation both in vitro and in vivo (FIG. 4A-C). Utilizing the myeloid DC2.4 cell line, we determined that genetic silencing of the β-catenin signaling pathway leads to a significant reduction in the expression of the mitochondrial fatty acid transporter, CPT1a (FIG. 4D). This was consistent with further experiments showing Wnt5a stimulation to directly induce CPT1a expression in a PPARγ-dependent manner in primary splenic DCs (data not shown). In order to determine if CPT1a targeting could regulate DC-mediated T cell responses, we evaluated the impact of ETO on DC-mediated effector T cell proliferation and we investigated the ability of ETO to modulate the effect of anti-PD-1 checkpoint antibody therapy on the growth of a transplanted BRAFV600E-PTEN−/− melanoma model in vivo (FIG. 5). These experiments showed ETO to significantly augment in vitro DC-dependent T cell proliferation to levels similar to that of LPS stimulation (FIG. 5A). In addition, administration of ETO significantly enhanced the anti-tumor efficacy of the anti-PD-1 antibody in the BRAFV600E-PTEN−/− transgenic melanoma model (FIG. 5B). Finally, we returned to the DC2.4 myeloid cell line and genetically silenced the expression of CPT1a using a shRNA-expressing lentiviral vector. Compared to non-targeting control DCs (NTC-DCs), these CPT1aKD DCs exhibited a diminished capacity to promote Treg differentiation in vivo and were found to potently induce the proliferation of antigen-specific CD8+ T cells (FIG. 6). These results demonstrate that pharmacologically or genetically targeting CPT1a in DCs is capable of inducing an augmented antigen-specific immune response.

Figure 7B:
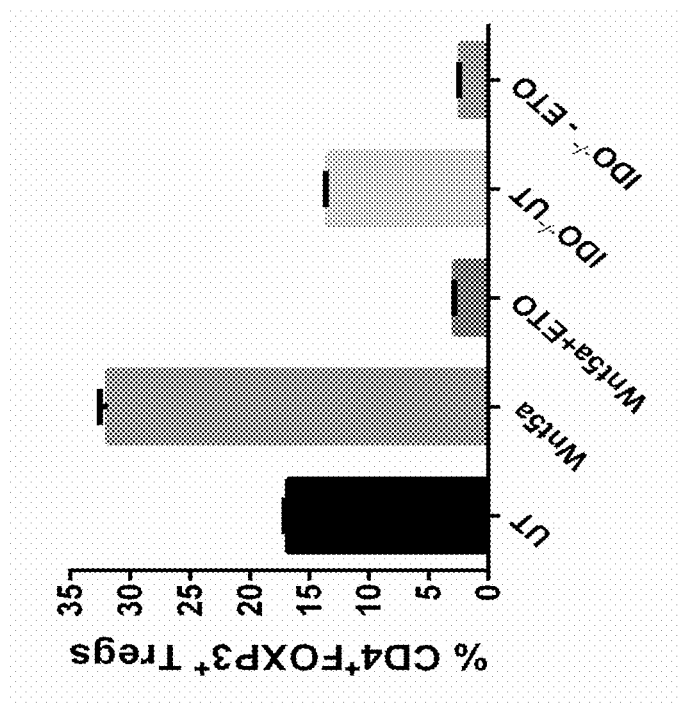
FIG. 7B demonstrates that inhibition of DC FAO suppresses IDO enzymatic activity and potently suppresses DC-mediated Treg differentiation. ETO inhibition of DC-mediated Treg generation extends beyond IDO activity. $IDO^{-/-}$ refers to DCs isolated from IDO1 knock-out mice.
Figure 7A:
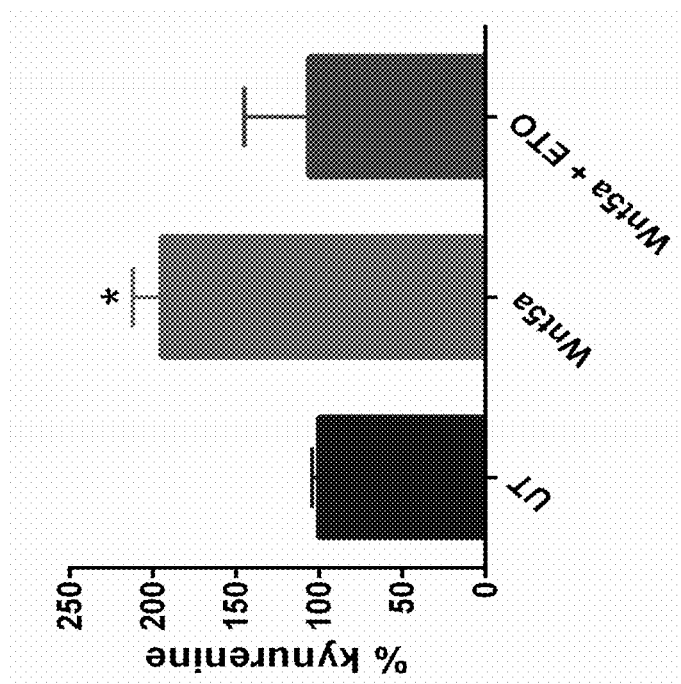
FIG. 7A demonstrates ETO reverses Wnt5a-stimulation of DC IDO enzymatic activity. HPLC assay measuring production of the metabolic product, kynurenine.
Figure 8:
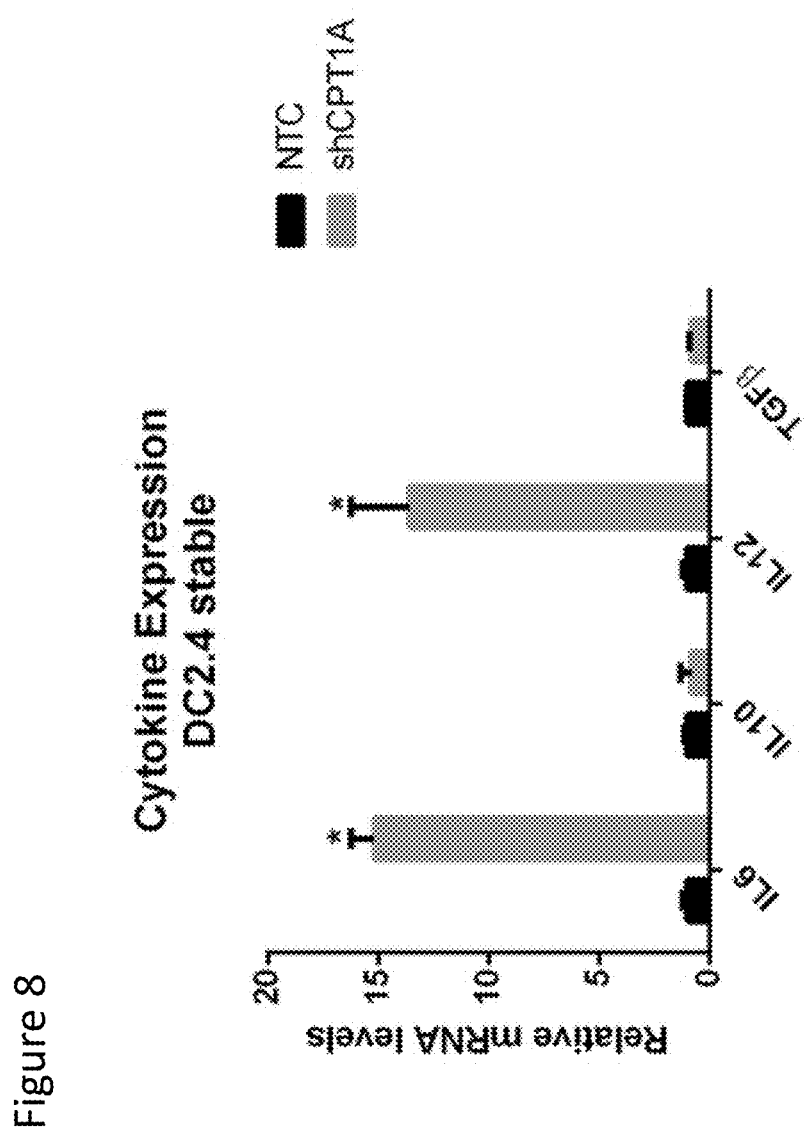
FIG. 8 demonstrates genetically silencing CPT1a in DCs potently induces IL-6 and IL-12 expression. Qrt-PCR analysis of cytokine expression following genetic silencing of CPT1a (shCPT1a) versus non-targeting control DCs (NTC-DCs).

In order to examine the mechanistic relationship between FAO and the promotion of DC-mediated Treg generation, we quantitated levels of the IDO byproduct, kynurenine, as a measure of DC IDO enzymatic activity using HPLC-based analysis. These studies confirmed our original hypothesis, demonstrating that IDO functionality was highly dependent upon the FAO state of the DC (FIG. 7A). Importantly, this work further showed that the pharmacological inhibition of DC FAO exhibited a more profound suppressive effect on in vitro Treg generation than even complete genetic knock-out of DC IDO (FIG. 7B). This data suggest that the ability of FAO to regulate DC-dependent Treg generation extends beyond IDO and likely involves other mediators. Indeed, our more recent data indicates DC FAO potently suppresses both IL-6 and IL-12 while the genetic silencing of CPT1a significantly augments the expression of these pro-inflammatory cytokines (FIG. 8). IL-6, in particular, has been shown to play an important role in promoting the differentiation and stability of Tregs (30). These data are consistent with our observations indicating that DC FAO manipulation can have a dramatic impact on resulting T cell activation levels. Together, our current data implies that the inhibition of DC FAO will have a more profound impact on immune modulation than the IDO inhibitors currently in clinical development.

Example 1: Literature Cited

1. Banchereau J, Steinman R. Dendritic cells and the control of immunity. Nature 1998; 392(6673):245-52.
2. Melief C J M. Cancer immunotherapy by dendritic cells. Immunity. 2008; 29:372-83.
3. Gilboa E. DC-based cancer vaccines. J Clin Invest. 2007; 117(5):1195-203. Epub 2007/05/04. doi: 10.1172/JCI31205. PubMed PMID: 17476349; PubMed Central PMCID: PMC1857263.
4. Ma Y, Shurin G V, Peiyuan Z, Shurin M R. Dendritic cells in the cancer microenvironment. Journal of Cancer. 2013; 4(1):36-44. Epub 2013 Feb. 2007. doi: 10.7150/j ca.5046. PubMed PMID: 23386903; PubMed Central PMCID: PMC3564245.
5. Gabrilovich D. Mechanisms and functional significance of tumor-induced dendritic cell defects. Nature Rev Immunol. 2004; 4:941-52.
6. Biswas S K. Metabolic Reprogramming of Immune Cells in Cancer Progression. Immunity. 2015; 43(3):435-49. Epub 2015/09/18. doi: 10.1016/j.immuni.2015.09.001. PubMed PMID: 26377897.
7. Enk A, Jonuleit H, Saloga J, Knop J. Dendritic cells as mediators of tumor-induced tolerance in metastatic melanoma. Int J Cancer. 1997; 73:309-16.
8. Ghiringhelli F, Puig P E, Roux S, Parcellier A, Schmitt E, Solary E, Kroemer G, Martin F, Chauffert B, Zitvogel L. Tumor cells convert immature myeloid dendritic cells into TGF-beta-secreting cells inducing CD4+CD25+ regulatory T cell proliferation. J Exp Med. 2005; 202(7):919-29. Epub 2005/09/28. doi: 10.1084/jem.20050463. PubMed PMID: 16186184; PubMed Central PMCID: PMC2213166.
9. Scarlett U K, Rutkowski M R, Rauwerdink A M, Fields J, Escovar-Fadul X, Baird J, Cubillos-Ruiz J R, Jacobs A C, Gonzalez J L, Weaver J, Fiering S, Conejo-Garcia J R. Ovarian cancer progression is controlled by phenotypic changes in dendritic cells. J Exp Med. 2012; 209(3):495-506. Epub 2012/02/22. doi: 10.1084/jem.20111413. PubMed PMID: 22351930; PubMed Central PMCID: PMC3302234.
10. Munn D H, Zhou M, Attwood J T, Bondarev I, Conway S J, Marshall B, Brown C, Mellor A L. Prevention of allogeneic fetal rejection by tryptophan catabolism. Science. 1998; 281:1191-3.
11. Munn D H, Sharma M D, Lee J R, Jhaver K G, Johnson T S, Keskin D B, Marshall B, Chandler P, Antonia S J, Burgess R, Slingluff C L, Jr., Mellor A L. Potential regulatory function of human dendritic cells expressing indoleamine 2,3-dioxygenase. Science. 2002; 297(5588): 1867-70. Epub 2002/09/14. doi: 10.1126/science.1073514 297/5588/1867 [pii]. PubMed PMID: 12228717.

12. Mellor A L, Baban B, Chandler P R, Marshall B, Jhaver K, Hansen A, Koni P A, Iwashima M, Munn D H. Cutting edge: induced indoleamine 2,3 dioxygenase expression in dendritic cell subsets suppresses T cell clonal expansion. J Immunol. 2003; 171:1652-5.

13. Fallarino F, Grohmann U, You S, McGrath B C, Cavener D R, Vacca C, Orabona C, Bianchi R, Belladonna M L, Volpi C, Santamaria P, Fioretti M C, Puccetti P. The combined effects of tryptophan starvation and tryptophan catabolites down-regulate T cell receptor {zeta}-chain and induce a regulatory phenotype in naive T cells. J Immunol. 2006; 176:6752-61.

14. Sharma M D, Baban B, Chandler P R, Hou D-Y, Singh N, Yagita H, Azuma M, Blazar B R, Mellor A L, Munn D H. Plasmacytoid dendritic cells from mouse tumor-draining lymph nodes directly activate mature Tregs via indoleamine-2,3-dioxygenase. J Clin Invest. 2007; 117 (9):2570-82.

15. Sharma M D, Huang L, Choi J H, Lee E J, Wilson J M, Lemos H, Pan F, Blazar B R, Pardoll D M, Mellor A L, Shi H, Munn D H. An inherently bifunctional subset of Foxp3+T helper cells is controlled by the transcription factor eos. Immunity. 2013; 38(5):998-1012. Epub 2013 May 2021. doi: 10.1016/j.immuni.2013.01.013. PubMed PMID: 23684987; PubMed Central PMCID: PMC3681093.

16. Katz J B, Muller A J, Prendergast G C. Indoleamine 2,3-dioxygenase in T-cell tolerance and tumoral immune escape. Immunol Rev. 2008; 222:206-21. Epub 2008 Mar. 2028. doi: 10.1111/j.1600-065X.2008.00610.x. PubMed PMID: 18364004.

17. Belkaid Y, Oldenhove G. Tuning microenvironments: induction of regulatory T cells by dendritic cells. Immunity. 2008; 29(3):362-71. Epub 2008 Sep. 2019. doi: 10.1016/j.immuni.2008.08.005. PubMed PMID: 18799144; PubMed Central PMCID: PMC3415213.

18. Darrasse-Jeze G, Podsypanina K. How Numbers, Nature, and Immune Status of Foxp3 Regulatory T-Cells Shape the Early Immunological Events in Tumor Development. Frontiers in immunology. 2013; 4:292. Epub 2013 Oct. 2018. doi: 10.3389/fimmu.2013.00292. PubMed PMID: 24133490; PubMed Central PMCID: PMC3784046.

19. Munn D H, Sharma M D, Hou D, Baban B, Lee J R, Antonia S J, Messina J L, Chandler P, Koni P A, Mellor A L. Expression of indoleamine 2,3-dioxygenase by plasmacytoid dendritic cells in tumor-draining lymph nodes. J Clin Invest. 2004; 114(2):280-90. Epub 2004 Jul. 2016. doi: 10.1172/JCI21583. PubMed PMID: 15254595; PubMed Central PMCID: PMC449750.

20. Krawczyk C M, Holowka T, Sun J, Blagih J, Amiel E, DeBerardinis R J, Cross J R, Jung E, Thompson C B, Jones R G, Pearce E J. Toll-like receptor-induced changes in glycolytic metabolism regulate dendritic cell activation. Blood. 2010; 115(23):4742-9. Epub 2010 Mar. 2031. doi: 10.1182/blood-2009-10-249540. PubMed PMID: 20351312; PubMed Central PMCID: PMC2890190.

21. Everts B, Amiel E, Huang S C, Smith A M, Chang C H, Lam W Y, Redmann V, Freitas T C, Blagih J, van der Windt G J, Artyomov M N, Jones R G, Pearce E L, Pearce E J. TLR-driven early glycolytic reprogramming via the kinases TBK1-IKKvarepsilon supports the anabolic demands of dendritic cell activation. Nat Immunol. 2014; 15(4):323-32. Epub 2014 Feb. 2025. doi: 10.1038/ni.2833. PubMed PMID: 24562310.

22. Malinarich F, Duan K, Hamid R A, Bijin A, Lin W X, Poidinger M, Fairhurst A M, Connolly J E. High mitochondrial respiration and glycolytic capacity represent a metabolic phenotype of human tolerogenic dendritic cells. J Immunol. 2015; 194(11):5174-86. Epub 2015 Apr. 2029. doi: 10.4049/jimmunol.1303316. PubMed PMID: 25917094.

23. Postow M A, Chesney J, Pavlick A C, Robert C, Grossmann K, McDermott D, Linette G P, Meyer N, Giguere J K, Agarwala S S, Shaheen M, Ernstoff M S, Minor D, Salama A K, Taylor M, Ott P A, Rollin L M, Horak C, Gagnier P, Wolchok J D, Hodi F S. Nivolumab and ipilimumab versus ipilimumab in untreated melanoma. N Engl J Med. 2015; 372(21):2006-17. Epub 2015 Apr. 2022. doi: 10.1056/NEJMoa1414428. PubMed PMID: 25891304.

24. Holtzhausen A, Zhao F, Evans K, Hanks B A. Early carcinogenesis involves the establishment of immune privilege via intrinsic and extrinsic regulation of indoleamine 2,3-dioxygenase-1: translational implications in cancer immunotherapy. Frontiers Immunology. 2014; 5:1-9. Epub September 2014.

25. Hanks B A, Holtzhausen A, Jamieson R, Gimpel P, Campbell O, Sun L, Tewari A, George A, Starr M, Nixon A, Augustine C, Beasley G, Tyler D S, Osada T, Morse M A, Ling L, Lyerly H K, Blobe G C. Type III TGF-β Receptor Downregulation Generates an Immunotolerant Tumor Microenvironment. J Clin Invest. 2013; 123(9): 3925-40. PubMed PMID: 23925295; PubMed Central PMCID: PMC3754240.

26. Holtzhausen A, Zhao F, Evans K, Tsutsui M, Orabona C, Tyler D S, Hanks B A. Melanoma-derived Wnt5a Promotes Local Dendritic-Cell Expression of IDO and Immunotolerance: Opportunities for Pharmacologic Enhancement of Immunotherapy. Cancer Immunol Res. 2015; 3(9):1082-95. Epub 2015 Jun. 2005. doi: 10.1158/2326-6066.CIR-14-0167. PubMed PMID: 26041736.

27. Dankort D, Curley D P, Cartlidge R A, Nelson B, Karnezis A N, Damsky W E, Jr., You M J, DePinho R A, McMahon M, Bosenberg M. Braf(V600E) cooperates with Pten loss to induce metastatic melanoma. Nat Genet. 2009; 41(5):544-52. Epub 2009 Mar. 2014. doi: ng.356 [pii] 10.1038/ng.356. PubMed PMID: 19282848; PubMed Central PMCID: PMC2705918.

28. Damsky W E, Curley D P, Santhanakrishnan M, Rosenbaum L E, Platt J T, Gould Rothberg B E, Taketo M M, Dankort D, Rimm D L, McMahon M, Bosenberg M. beta-catenin signaling controls metastasis in Braf-activated Pten-deficient melanomas. Cancer Cell. 2011; 20(6):741-54. Epub 2011 Dec. 2017. doi: 10.1016/j.ccr.2011.10.030. PubMed PMID: 22172720; PubMed Central PMCID: PMC3241928.

29. Sherwood V, Chaurasiya S K, Ekstrom E J, Guilmain W, Liu Q, Koeck T, Brown K, Hansson K, Agnarsdottir M, Bergqvist M, Jirstrom K, Ponten F, James P, Andersson T. WNT5A-mediated beta-catenin-independent signalling is a novel regulator of cancer cell metabolism. Carcinogenesis. 2014; 35(4):784-94. Epub 2013 Dec. 2003. doi: 10.1093/carcin/bgt390. PubMed PMID: 24293407; PubMed Central PMCID: PMC3977146.

30. Sharma M D, Shinde R, McGaha T L, Huang L, Holmgaard R B, Wolchok J D, Mautino M R, Celis E, Sharpe A H, Francisco L M, Powell J D, Yagita H, Mellor A L, Blazar B R, Munn D H. The PTEN pathway in Tregs is a critical driver of the suppressive tumor microenvironment. Science advances. 2015; 1(10):e1500845. doi: 10.1126/sciadv.1500845. PubMed PMID: 26601142; PubMed Central PMCID: PMC4640592.

Example 2: Paracrine Wnt5a-β-Catenin Signaling Triggers a Metabolic Switch the Drives Dendritic Cell Tolerization in the Melanoma Microenvironment Despite recent advances, many cancers remain refractory to available immunotherapeutic strategies. Emerging evidence indicates that the tolerization of local dendritic cells (DCs) within the tumor microenvironment promotes immune evasion. This Example describes a mechanism by which melanomas establish a site of immune privilege via a paracrine Wnt5a-β-catenin-PPAR-γ signaling pathway that drives fatty acid oxidation (FAO) in local DCs by upregulating the expression of the CPT1A mitochondrial fatty acid transporter. This FAO shift increases levels of the protoporphyrin IX prosthetic group of indoleamine 2,3-dioxgenase-1 (IDO) while suppressing IL-6/IL-12 cytokine expression, all culminating in enhanced IDO activity and the robust generation of local regulatory T cells. It is demonstrated that genetic and pharmacologic blockade of this pathway robustly augments anti-melanoma immunity, enhances the activity of anti-PD-1 antibody immunotherapy, and significantly suppresses disease progression in a transgenic BRAF$^{V600E}$ melanoma model. This work implicates a role for tumor-mediated metabolic reprogramming of local DCs in immune evasion and immunotherapy resistance.

As discussed above, the dendritic cell (DC) is now recognized as a key player in the generation of anti-tumor immunity. By processing and presenting antigen, the individual DC induces the activation and modulates the functionality of a larger population of naïve T cells (Banchereau and Steinman, 1998). Studies have recently described DCs within the tumor microenvironment as contributing to tumor pathogenesis, suggesting that these antigen presenting cell populations undergo a tolerization program allowing them to generate an immune privileged microenvironment (Hanks et al., 2013; Scarlett et al., 2012). However, the mechanisms by which cancers induce this DC tolerization program have been largely unknown. An improved understanding of immune evasion including the process of DC tolerization promises to provide critical insight into novel mechanisms of immunotherapy resistance and the identity of previously unappreciated immunotherapeutic targets.

Several lines of evidence have implicated a critical role for the immunoregulatory enzyme, indoleamine 2,3-dioxygenase-1 (IDO), in tumor-mediated immune suppression (Munn et al., 2004). By catalyzing the conversion of the essential amino acid tryptophan into the metabolic byproducts known as the kynurenines, IDO is capable of suppressing the expansion of effector T cells while also promoting the differentiation and activation of the CD4$^+$ FoxP3$^+$ regulatory T cell (Treg) population (Fallarino et al., 2006; Sharma et al., 2007). IDO requires the heme prosthetic group, protoporphyrin IX (PpIX), for full enzymatic activity (Shimizu et al., 1978). This has been supported by studies demonstrating the inhibition of PpIX synthesis to significantly suppress the activity of IDO while the addition of the heme biosynthetic precursor β-aminolevulinic acid results in augmented levels of IDO activity (Thomas et al., 2001). Although IDO is also expressed by some tumors, DC expression of IDO has been demonstrated to be particularly important for generating a site of immune privilege during cancer progression (Munn and Mellor, 2007). Indeed, lymph node DC IDO expression has been correlated with a poor prognosis in melanoma (Munn et al., 2004; Munn et al., 2002). The realization of the critical role of IDO in tumor-mediated immune suppression has led to the design and development of small molecule inhibitors of the IDO enzyme that have now entered into late phase clinical trials as a strategy to augment anti-tumor immunity (Mullard, 2015). Despite the importance of IDO in tumor-mediated immune tolerance, very little is understood regarding the mechanisms that evolving cancers use to regulate its function.

Previous investigators have described the β-catenin signaling pathway as playing a role in the induction of DC tolerization (Jiang et al., 2007; Manicassamy et al., 2010). More recently, we delineated a paracrine signaling pathway by which melanomas generate an immunotolerant microenvironment via a Wnt5a-dependent mechanism (Holtzhausen et al., 2015). By inducing β-catenin activation in nearby DCs, melanoma-derived Wnt5a induces the transcriptional expression of IDO, culminating in the generation of Tregs and the establishment of an immune privileged site that allows for melanoma disease progression. While the canonical Wnt ligand, Wnt3a, was also found to induce the expression of IDO by DCs, we noted that Wnt3a-conditioned DCs failed to induce Treg differentiation (Holtzhausen et al., 2015). These findings raised the intriguing possibility that Wnt5a was capable of regulating IDO via an unknown post-transcriptional mechanism. A recent RNAseq differential gene expression study also associated this pathway with checkpoint inhibitor resistance by demonstrating Wnt5a to be significantly upregulated in melanoma tissues refractory to anti-PD-1 antibody immunotherapy (Hugo et al., 2016).

Prior studies have established that DC maturation, a genetic program that allows for effective DC-dependent effector T cell activation, is accompanied by a glycolytic surge (Krawczyk et al., 2010). Indeed, subsequent studies showed the inhibition of the DC glycolytic pathway to diminish DC-mediated T cell stimulation (Everts et al., 2014). Other studies have demonstrated that the Wnt5a ligand is capable of modulating cellular metabolism in various systems (Sherwood et al., 2014). Based on these findings, we hypothesized that melanoma-derived Wnt5a metabolically reprograms local DC populations to support IDO enzymatic activity and subsequent Treg differentiation and that this represents a mechanism by which cancers can hijack an intrinsic immunologic switch capable of shifting the host immune system toward a tolerogenic state. We further propose that this pathway represents a promising pharmacological target capable of augmenting checkpoint inhibitor immunotherapy.

Results

Melanoma-Derived Wnt5a Reprograms DC Energy Metabolism.

Figure 9B:
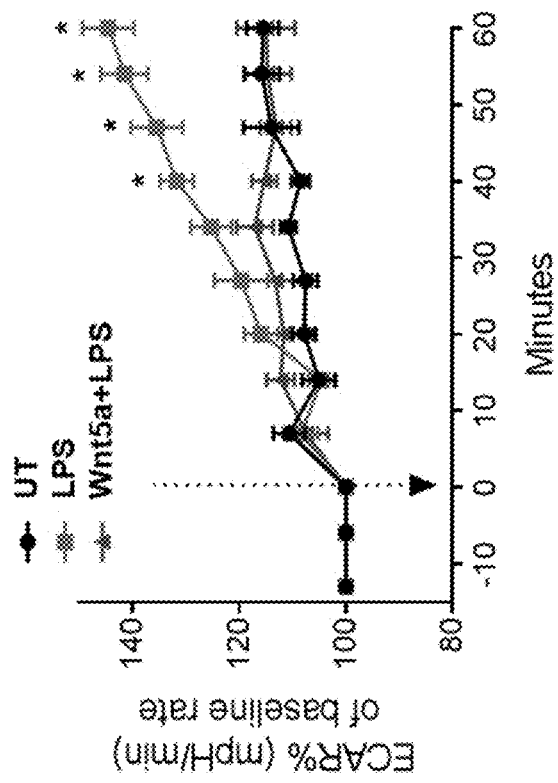
FIG. 9B demonstrates extracellular acidification rate (ECAR, milli-pH units per minute, normalized to 0 minutes) of BMDC untreated (UT) vs. Wnt5a pretreatment. Arrow indicates LPS injection. n=6.
Figure 9A:
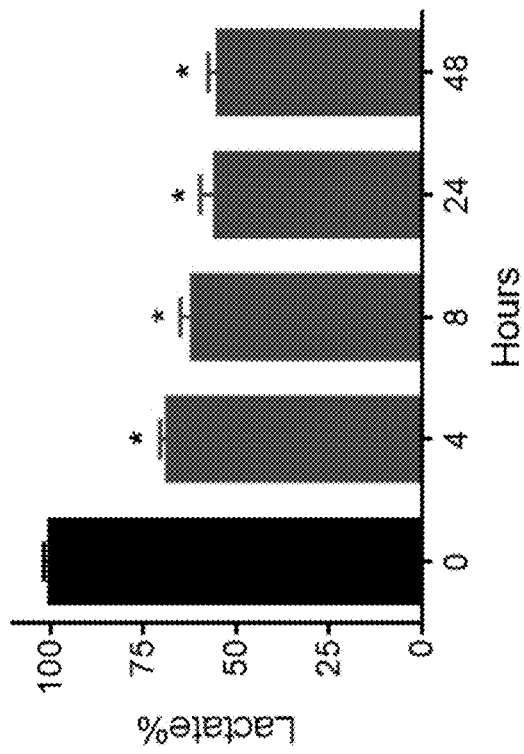
FIG. 9A demonstrates melanoma-derived Wnt5a alters DC energy metabolism. Lactate levels in BMDC culture media from 0-48 hours with Wnt5a treatment. n=6.
Figure 9C:
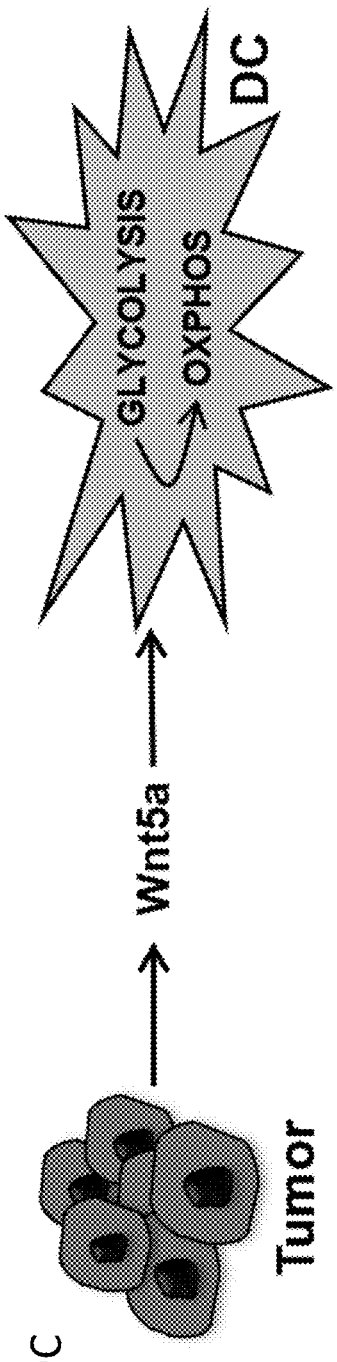
FIG. 9C is a schematic illustrating the impact of Wnt5a paracrine signaling on DCs within the tumor microenvironment.
Figure 9E:
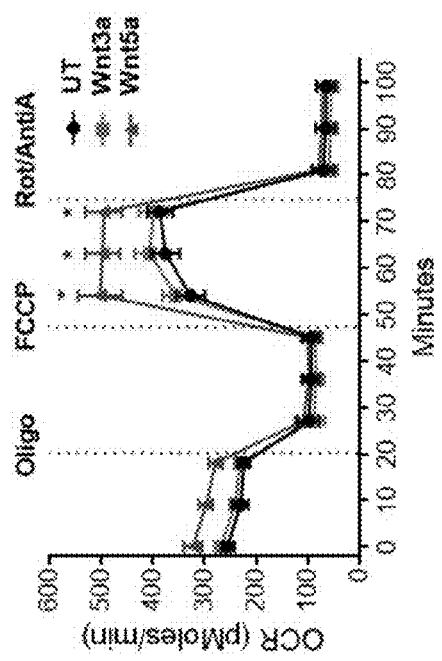
FIG. 9E is a graph showing OCR of BMDCs pre-treated with Wnt5a vs. Wnt3a. n=6. Oligo, oligomycin. FCCP, uncoupling agent. Rot, rotenone.
Figure 9G:
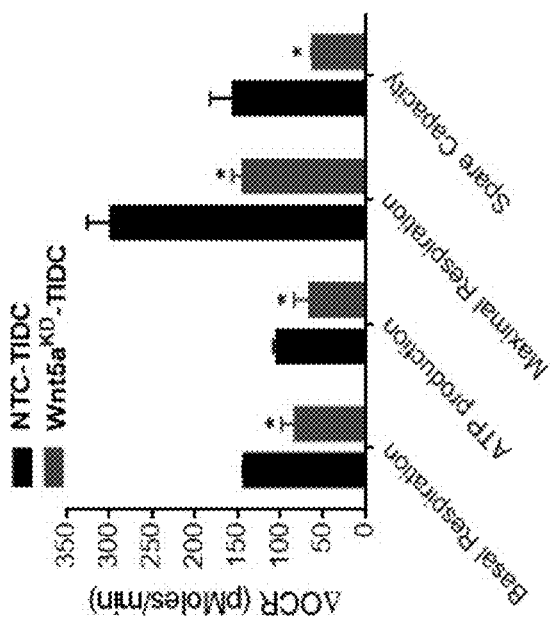
FIG. 9G is a bar graph showing metabolic parameter calculations based on 1F. n=3/group. All data is mean+/− S.D. *P<0.05. See also FIG. 16.
Figure 9D:
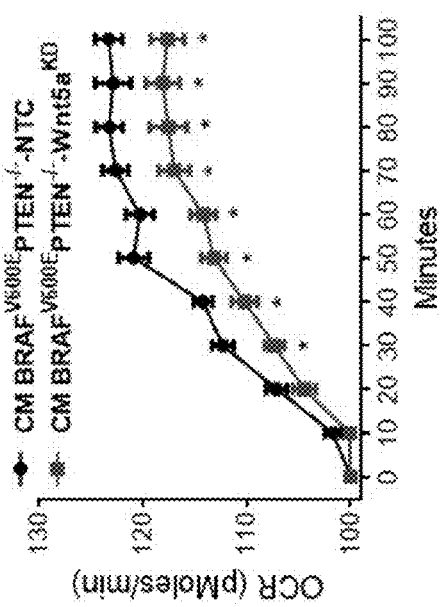
FIG. 9D is a graph showing oxygen consumption rate (OCR, pico-moles per minute) of BMDCs injected with concentrated conditioned media (CM) from $BRAF^{V600E}PTEN^{-/-}$—NTC or -$Wnt5a^{KD}$ cell cultures. n=6.
Figure 9F:
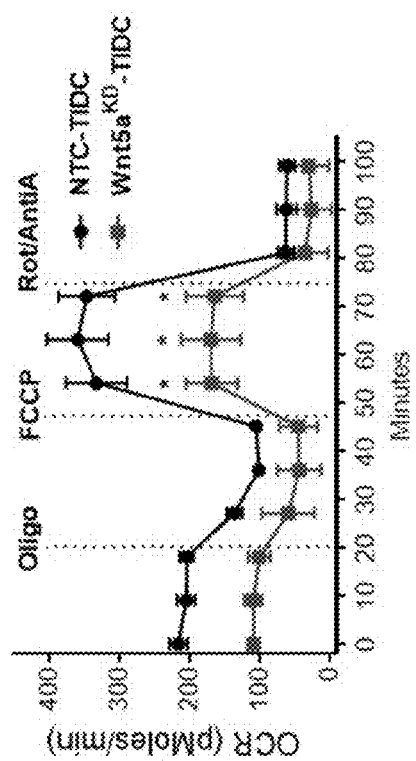
FIG. 9F is a graph showing OCR of TIDCs isolated from $BRAF^{V600E}PTEN^{-/-}$-NTC and -$Wnt5a^{KD}$ mice. n=3/group.
Figure 16A:
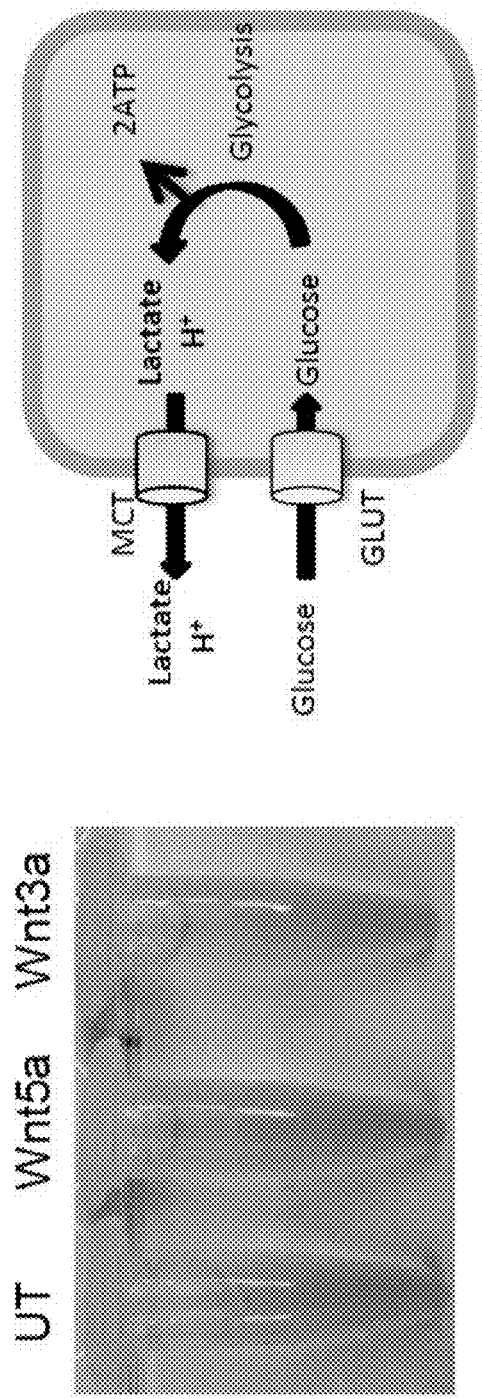
FIG. 16A demonstrates Wnt5a, but not Wnt3a, inhibits DC glycolysis. BMDCs were treated with Wnt5a ligand (200 ng/ml) or Wnt3a ligand (100 ng/ml) for 48 hours in a glucose-rich, phenol red-containing media. Yellow indicates an acidic pH while red indicates a more neutral pH. MCT, lactate transporter protein. GLUT, glucose transporter protein.
Figure 16B:
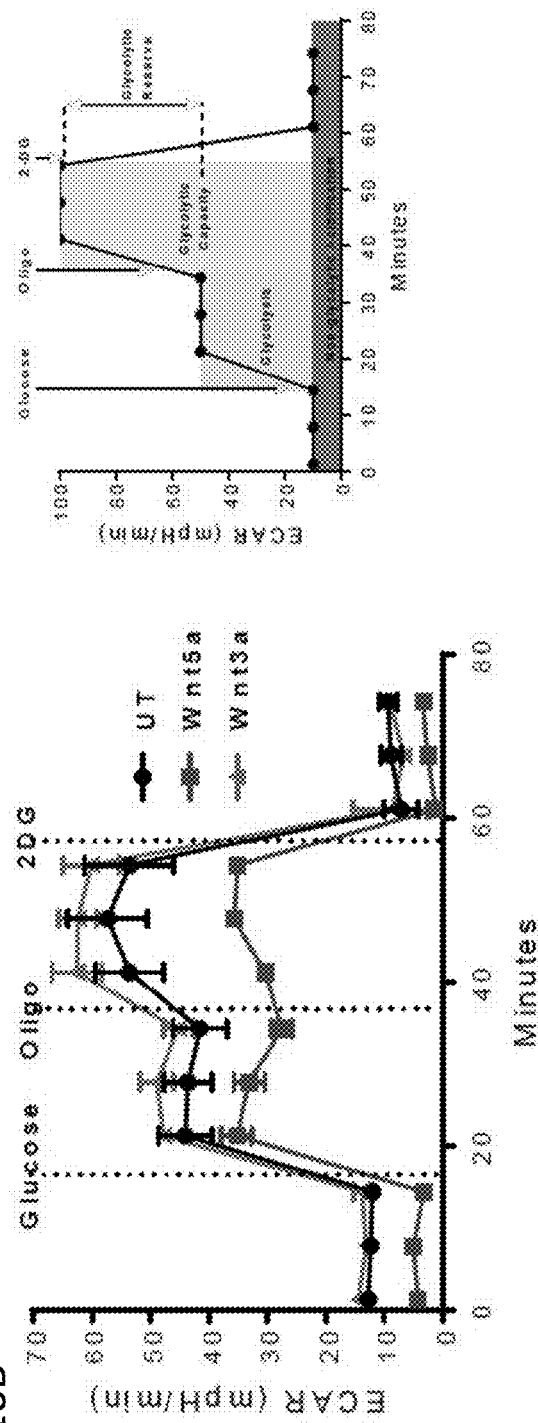
FIG. 16B demonstrates BMDCs treated with either Wnt5a ligand or Wnt3a for 24 hours and subjected to glycolysis analysis. ECAR, extracellular acidification rate. Oligo, oligomycin, an ATP synthase inhibitor. 2DG, 2-deoxyglucose, a hexokinase inhibitor.

Recent studies have demonstrated that Toll-like receptor (TLR)-induced DC maturation involves the induction of glycolysis (Everts et al., 2014; Krawczyk et al., 2010). Our previous work has shown that melanoma-expressed soluble Wnt5a signals via the β-catenin signaling pathway to drive DC tolerization (Holtzhausen et al., 2015). Others have also shown Wnt5a to regulate cellular metabolism (Elghazi et al., 2012; Sherwood et al., 2014). Based on these findings, we sought to investigate whether Wnt5a was capable of suppressing DC glycolysis and whether this may contribute to the process of DC tolerization. Using a biochemical extracellular lactate assay as a surrogate for glycolysis, we found the Wnt5a ligand to suppress lactate production by bone marrow-derived DCs (BMDCs) (FIGS. 9A, 16A). By monitoring the extracellular acidification rate (ECAR) in vitro, we further determined that Wnt5a ligand treatment eliminates the glycolytic reserve of DCs while also significantly suppressing the lipopolysaccharide (LPS)-induced glycolytic surge typically observed during the DC maturation program (FIGS. 9B, 16B). To determine whether melanoma-derived Wnt5a was capable of influencing DC metabolism, we analyzed the oxygen consumption rate (OCR) of purified DCs stimulated with conditioned media harvested either from a control $BRAF^{V600E}$-$PTEN^{-/-}$ melanoma cell line ($BRAF^{V600E}$-$PTEN^{-/-}$-NTC) or a $BRAF^{V600E}$-$PTEN^{-/-}$ melanoma cell line genetically silenced for Wnt5a expression ($BRAF^{V600E}$-$PTEN^{-/-}$-$Wnt5a^{KD}$) (FIG. 9C) (Holtzhausen et al., 2015). This work suggested that melanoma-derived Wnt5a promotes DC oxidative phosphorylation (OXPHOS), an effect that was also confirmed with recombinant Wnt5a stimulation (FIGS. 9D, 9E). However no changes in either DC OXPHOS or glycosis were observed following Wnt3a treatment, providing further support for differential DC pathway activation by these Wnt ligands (FIGS. 9E, 16B). In order to confirm that melanoma-derived Wnt5a was also capable of modulating DC metabolism in vivo, we purified tumor-infiltrating DCs (TIDCs) from both $BRAF^{V600E}$-$PTEN^{-/-}$-NTC and $BRAF^{V600E}$-$PTEN^{-/-}$-$Wnt5a^{KD}$ tumors resected from syngeneic mice and measured their real-time OCR. Consistent with our previous findings, this study demonstrated melanoma-derived Wnt5a to promote DC mitochondrial respiration in the melanoma microenvironment (FIGS. 9F, 9G). Taken together, this data reveals that melanoma tissues shift the metabolism of local DC populations from a glycolytic state toward an OXPHOS state in a Wnt5a-dependent manner.

Wnt5a-Mediated Metabolic Reprogramming Alters DC Function.

Figure 10A:
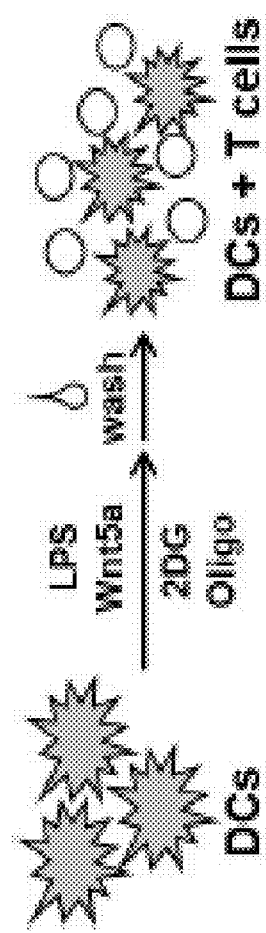
FIG. 10A is a schematic describing the DC conditioning protocol utilized in T cell assays.
Figure 10B:
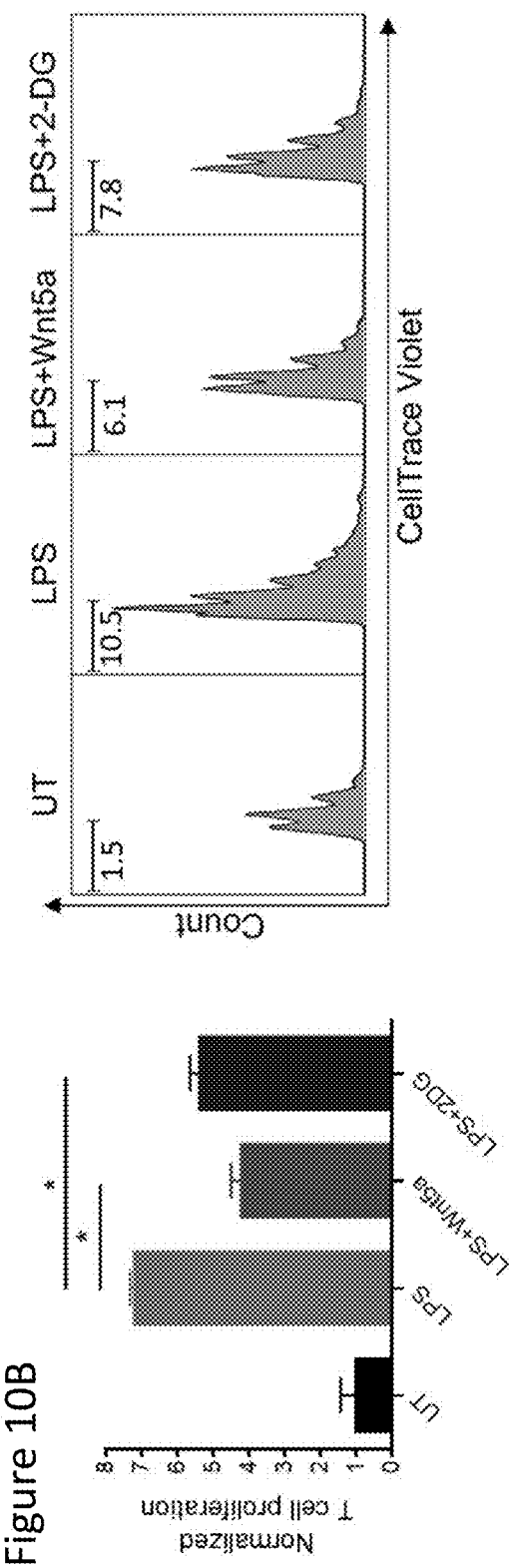
FIG. 10B is a graph showing T cell proliferation assay: BMDCs loaded with OVA257-264 peptide (SIINFEKL, SEQ ID NO:2), treated with Wnt5a or 2-deoxyglucose (2DG), stimulated with LPS, and co-incubated with OT-1 splenocytes. $CD8^+$ T cell proliferation measured by Cell-Trace Violet dilution. n=3. right, Representative flow cytometry CellTrace Violet dilution assay. Gated on $CD8^+$ T cells.

Previous studies have demonstrated that the inhibition of hexokinase, the initial enzyme in the glycolytic pathway, using 2-deoxyglucose (2-DG) suppresses DC-induced T cell proliferation while others have found DCs that exhibit a tolerized phenotype demonstrate enhanced levels of OXPHOS (Everts et al., 2014; Malinarich et al., 2015). Consistent with these findings as well as our data showing that Wnt5a is capable of blocking LPS-induced DC glycolysis, we also determined that Wnt5a suppresses LPS-induced DC-mediated antigen-specific T cell proliferation (FIGS. 10A, 10B). This data indicated that the inhibition of DC glycolysis and the inhibition of DC OXPHOS would have reciprocal effects on the development of Tregs. Indeed, co-culturing 2-DG-treated DCs with naïve $CD4^+$ cells generated enhanced Treg differentiation in vitro while the inhibition of DC OXPHOS with oligomycin (oligo) resulted in almost complete elimination of these Treg populations (FIGS. 10A, 10C). We have previously shown Wnt5a to promote DC-mediated Treg differentiation both in vitro and in vivo (Holtzhausen et al., 2015). Together, these findings imply that Wnt5a drives Treg differentiation in the melanoma microenvironment by promoting DC OXPHOS. This would also be consistent with our previous data showing that Wnt3a neither regulates DC metabolism nor promotes DC-mediated Treg generation (FIGS. 9E, 16B) (Holtzhausen et al., 2015). In order to examine this question more directly, we purified the TIDCs from both $BRAF^{V600E}$-$PTEN^{-/-}$-NTC and $BRAF^{V600E}$-$PTEN^{-/-}$-$Wnt5a^{KD}$ tumors and delivered them by intradermal footpad injection into syngeneic FoxP3-mRFP transgenic reporter mice followed by ipsilateral popliteal and inguinal lymph node isolation and Treg flow cytometry analysis (FIG. 10D). This work confirmed that the $BRAF^{V600E}$-$PTEN^{-/-}$- $Wnt5a^{KD}$ tumor-derived DC population previously shown to exhibit diminished levels of OXPHOS (FIGS. 9F, 9G) also suppresses Treg differentiation in vivo (FIG. 10E). In summary, metabolic re-programming plays a central role in Wnt5a regulation of DC functionality and determines whether a DC drives effector T cell expansion versus Treg differentiation (FIG. 10F).

Wnt5a Induction of DC Fatty Acid Oxidation Promotes Treg Development and Suppresses Effector T Cell Activation.

Earlier studies have shown that cancer-associated DCs exhibit higher cytoplasmic lipid content via increased lipid uptake and that these elevated lipid levels impair DC antigen processing and presentation (Herber et al., 2010). Since our data indicates that melanoma-derived Wnt5a alters DC function, we also investigated the impact of Wnt5a on DC lipid levels. Consistent with these earlier findings, these studies demonstrated the Wnt5a-β-catenin pathway to enhance DC fatty acid uptake and lipid stores (FIGS. 11A, 11B).

Figure 17A:
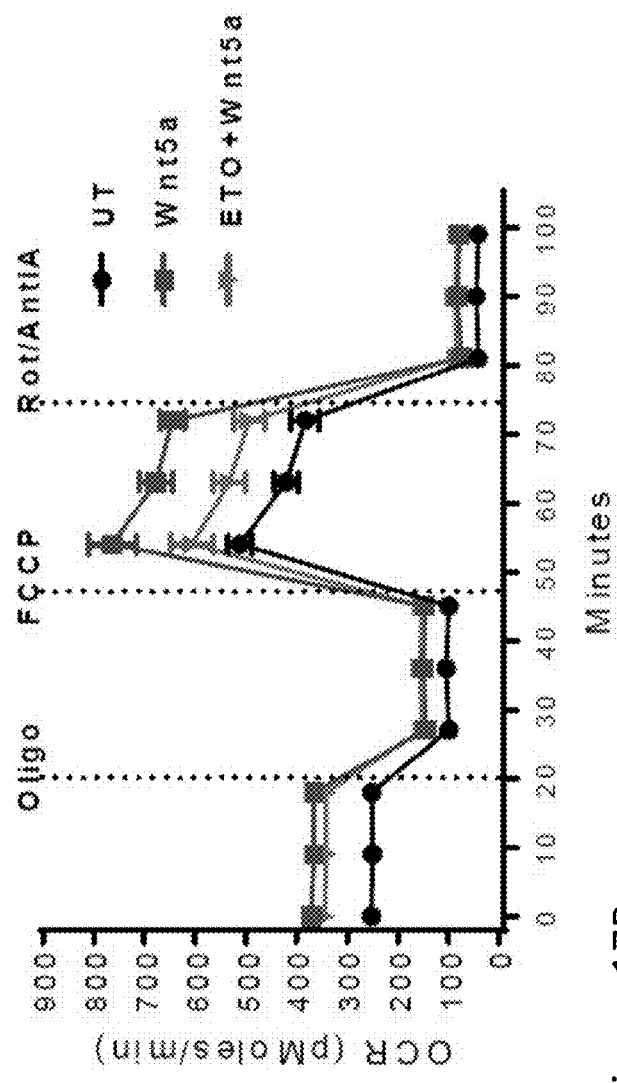
FIG. 17A demonstrates Wnt5a induces OCR in human monocyte-derived DCs and FAO inhibition does not impair DC viability. Human DCs were differentiated from harvested peripheral blood mononuclear cells and pre-treated with Wnt5a 48 hours prior to OCR analysis. Short-term incubation with ETO was performed prior to analysis.
Figure 17B:
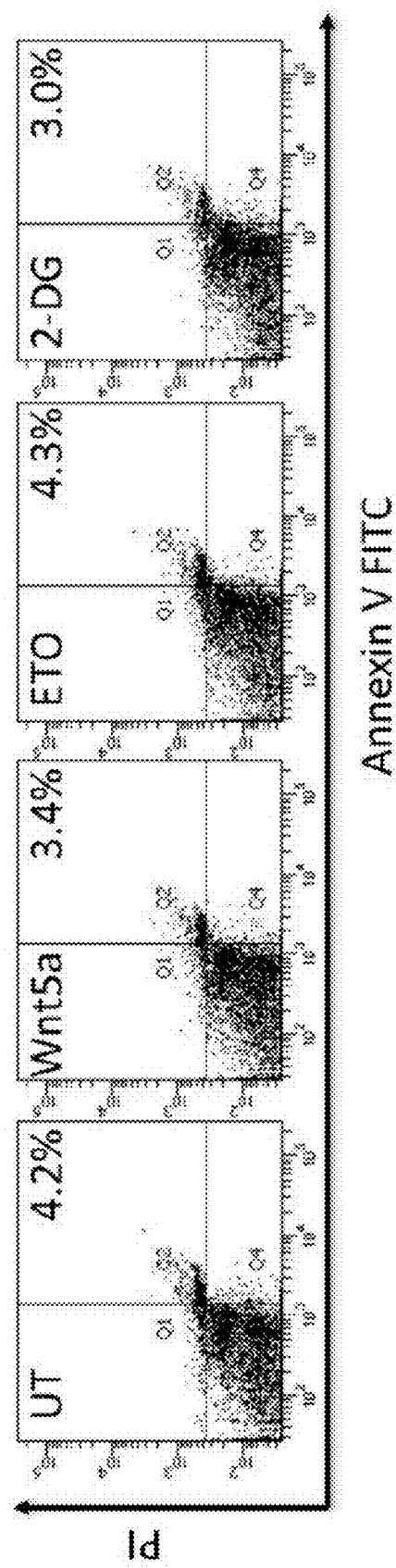
FIG. 17B shows BMDCs were treated with the indicated condition for 48 hours, washed, and stained with Annexin V/PI for flow cytometry analysis. Data is representative of two-independent experiments.
Figure 18A:
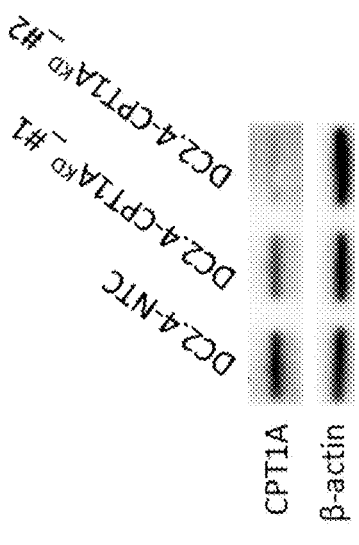
FIG. 18A shows primary DCs predominantly express the CPT1A isoform based on qrt-PCR analysis.
Figure 18B:
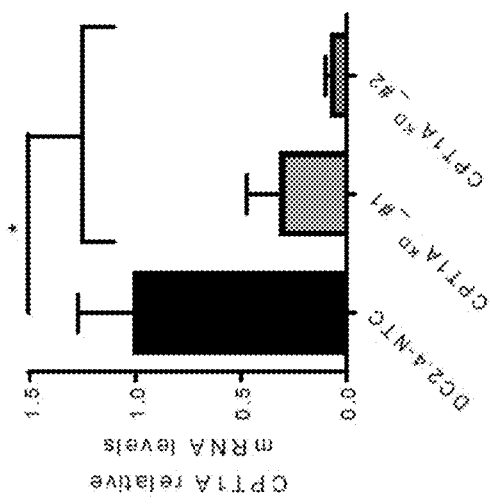
FIG. 18B shows qrt-PCR analysis demonstrating successful silencing of CPT1A in the DC2.4 cell line.
Figure 18C:
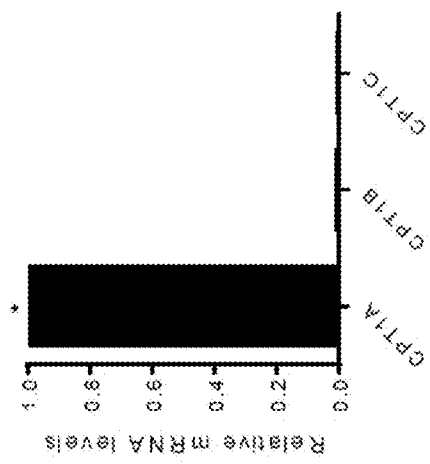
FIG. 18C shows Western blot evaluation of CPT1A expression in the DC2.4-NTC control cell line and the DC2.4-CPT1AKD cell lines is consistent with the qrt-PCR findings showing successful genetic silencing of CPT1A (B). DC2.4-CPT1AKD #2 stable line used for future experiments.
Figure 18D:
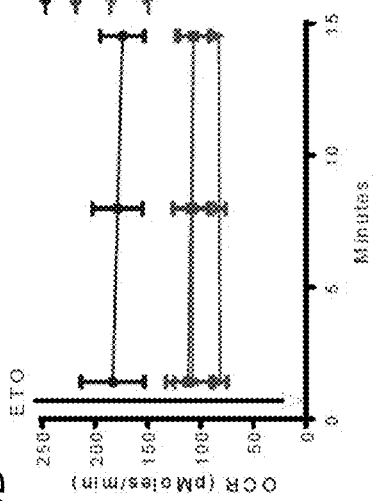
FIG. 18D shows OCR measurement of the indicated groups over a period of 15 minutes.
Figure 18E:
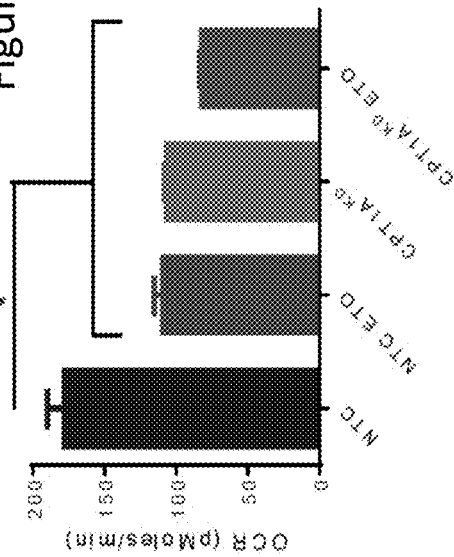
FIG. 18E shows mean of repeated measures from (D). *p<0.05.

Based on these data, we reasoned that Wnt5a may achieve enhanced levels of DC OXPHOS by promoting fatty acid oxidation (FAO). In order to determine if Wnt5a regulated DC FAO, we analyzed the real-time OCR of DCs treated with Wnt5a in the presence and absence of the carnitine palmitoyl transferase-1 (CPT1) mitochondrial fatty acid transporter inhibitor, etomoxir (ETO). These experiments showed ETO to completely ablate Wnt5a induction of both murine and human DC mitochondrial respiration while not impacting DC viability (FIGS. 11C, 11D, 17). Given that our prior data suggested that DC OXPHOS played an important role in DC-mediated Treg generation and additional studies indicated that DC glutaminolysis did not seem to be involved in this process (data not shown), we directly investigated the role of FAO in DC-dependent Treg generation. This work demonstrated ETO treatment of primary DCs to potently suppress the ability of Wnt5a-conditioned DCs to drive Treg differentiation in vitro as well as in vivo following the adoptive transfer of conditioned DCs into FoxP3− mRFP reporter mice (FIGS. 11E, 11F). In line with our previous data indicating that the inhibition of DC OXPHOS promotes antigen-specific T cell proliferation, we also found ETO treatment to potently induce DC-mediated T cell activation to levels similar to those seen in response to LPS-treatment of DCs (FIG. 11G). In order to confirm that the off-target effects of ETO did not contribute to this process, we genetically silenced CPT1A expression by the DC2.4 myeloid DC line and determined the ability of the resulting DC2.4-$CPT1A^{KD}$ cell line to induce Treg differentiation in vivo as well as to promote effector T cell proliferation in vitro relative to the DC2.4-NTC control cell line (FIG. 18). This work showed genetic silencing of CPT1A to eliminate Wnt5a-conditioned DC stimulation of Tregs in vivo while also promoting DC-mediated CD8+ T cell proliferation (FIGS. 11H, 11I). Overall, these data provide a mechanistic explanation for the increased levels of lipid stores previously observed in cancer-associated DCs. In addition, this work implies that Wnt5a shifts DCs from glycolysis towards a state favoring FAO in the melanoma microenvironment and that this metabolic switch effectively inhibits effector T cell activation while driving Treg differentiation.

The Wnt5a-β-Catenin Signaling Pathway Regulates DC Fatty Acid Oxidation Via the PPAR-γ-CPT1a Axis.

Figures 19A, 19B, 19C, 19D, 19E:
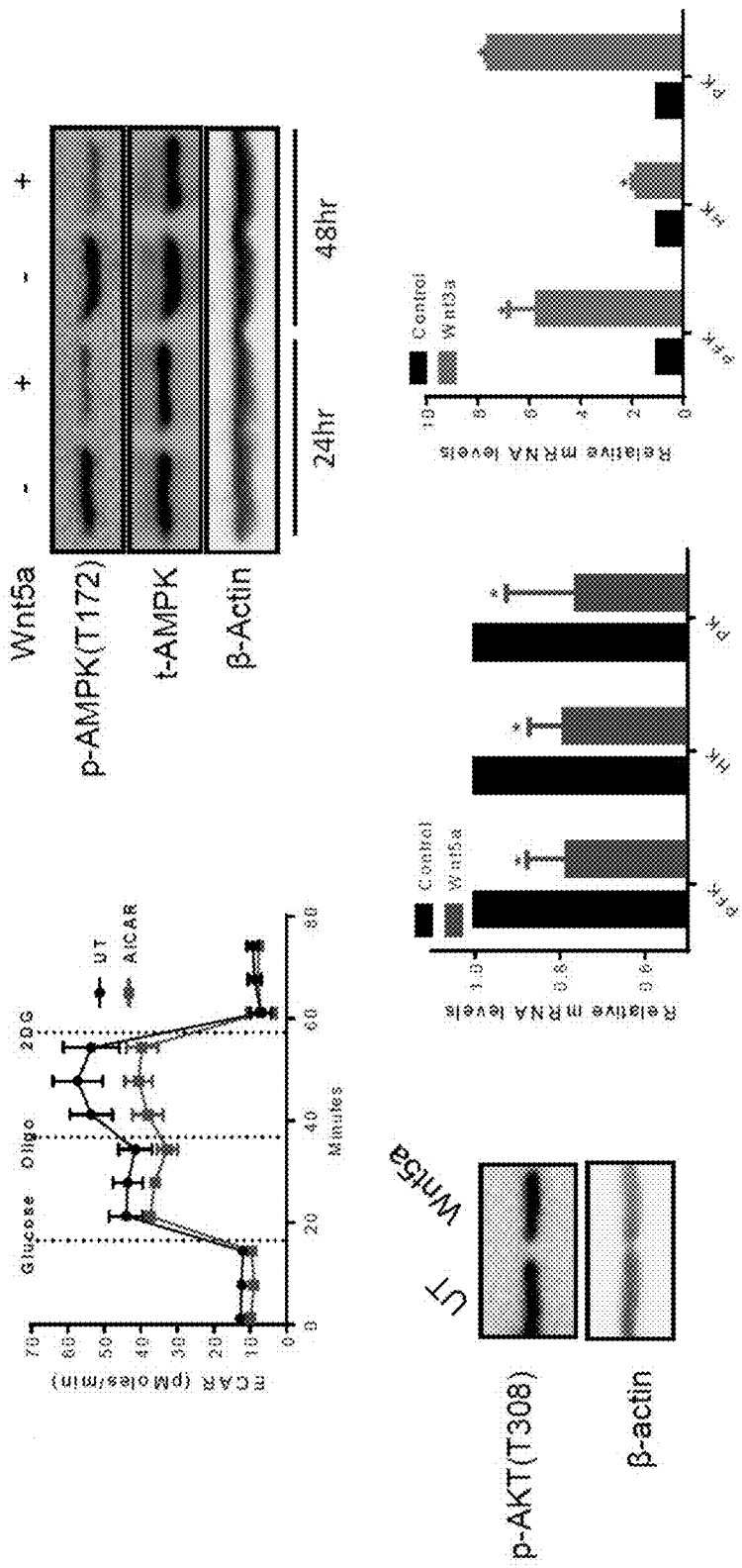
FIG. 19A shows treatment of BMDCs with AICAR for 24 hrs suppresses OXPHOS. UT, untreated. AICAR, AMP analog and AMPK agonist.
FIG. 19B shows immunoblot analysis of p-AMPK(T172) and t-AMPK levels following Wnt5a (200 ng/mL) stimulation of BMDCs after 24 and 48 hrs.
FIG. 19C shows immunoblot analysis of p-AKT(T308) levels following Wnt5a (200 ng/mL) stimulation of BMDCs after 48 hrs. All data representative of 3 independent experiments.
FIG. 19D shows Wnt5a suppresses the expression of key glycolytic enzymes in DCs based on qrt-PCR analysis. PFK, phosphofructokinase (rate-limiting). HK, hexokinase. PK, pyruvate kinase. *P<0.05.
FIG. 19E shows Wnt3a promotes the expression of key glycolytic enzymes in DCs based on qrt-PCR analysis. PFK, phosphofructokinase (rate-limiting). HK, hexokinase. PK, pyruvate kinase. *P<0.05.

Previous investigators have proposed that activation of AMP-activated protein kinase (AMPK) by the AMP analog, AICAR, would antagonize the glycolytic surge required for DC maturation (Dong and Bullock, 2014; Krawczyk et al., 2010). Our findings are consistent with this work (FIG. 19A). As a result, we hypothesized that Wnt5a shifts DC metabolism from glycolysis to FAO by stimulating AMPK activation. However, we found Wnt5a to suppress AMPK activation based on Thr-172 phospho-AMPK Western blot analysis (FIG. 19B). In addition, we detected no significant impact of Wnt5a on DC Akt Thr-308 phosphorylation, a well characterized promoter of DC glycolysis (FIG. 19C) (Krawczyk et al., 2010). Despite this data, we found Wnt5a, but not Wnt3a, to suppress the expression of the key glycolytic enzymes, phosphofructokinase, hexokinase, and pyruvate kinase in primary DCs (FIGS. 19D-19E). These results support our previous observations that Wnt5a suppresses DC glycolysis while promoting DC OXPHOS and indicates that this mechanism is independent of the Akt-AMPK pathway.

Previous studies have demonstrated that the peroxisome proliferator-activated receptor (PPAR) family of transcription factors play an important role in regulating the expression of several key factors involved in FAO (Keller et al., 1993). We have found that treatment of primary DCs with the β-catenin inhibitor, XAV939, and the genetic silencing of β-catenin in the DC2.4 cell line (DC2.4-β-catenin$^{KD}$) to promote DC glycolysis, confirming an important role for β-catenin in the regulation of DC metabolism (FIG. 20). Indeed, β-catenin induction of PPAR-γ expression has been described (Jansson et al., 2005). Consistent with these findings, we found Wnt5a stimulation of primary DCs to induce the expression of several downstream genes of the PPAR-γ transcription factor previously identified to promote FAO, including CPT1A, using a quantitative polymerase chain reaction (qPCR) array (FIG. 12A). We subsequently found that Wnt5a induces the upregulation of PPAR-γ and CPT1A using quantitative real-time PCR and Western blot analysis in both murine and human DCs (FIGS. 12B-12D) (Mascaro et al., 1998; Napal et al., 2005). To confirm that β-catenin regulates CPT1A expression, we found reduced levels of CPT1A in the DC2.4 cell line after genetically silencing β-catenin (DC2.4-β-catenin$^{KD}$) while β-catenin activation of primary DCs via GSK3β inhibition also promotes both PPAR-γ and CPT1A expression (FIGS. 12E-12F, 20B-20C). Consistent with its inability to alter DC metabolism, Wnt3a also failed to induce the expression of both PPAR-γ and CPT1A in DCs (FIG. 21A).

Figure 12H:
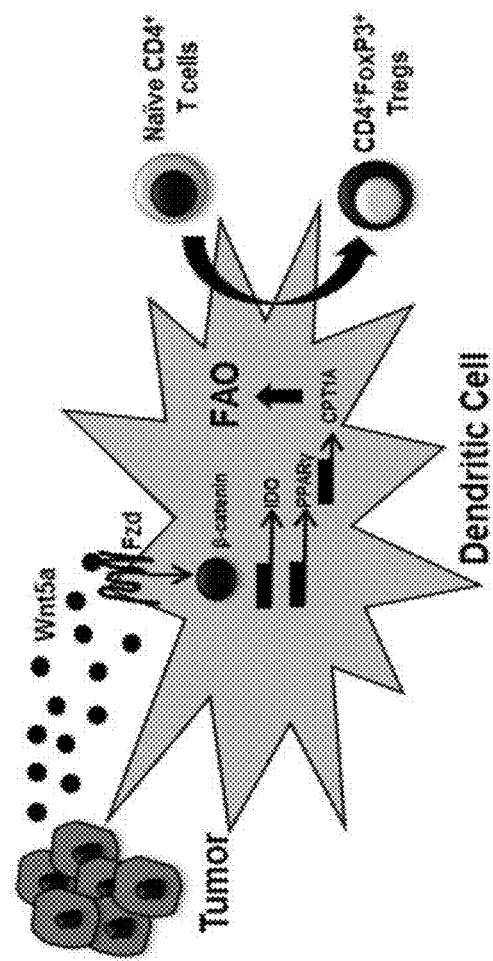
FIG. 12H is a schematic of Melanoma-derived Wnt5a inducing local DC FAO via the β-catenin-PPARγ pathway. All data is mean+/−S.D. *P<0.05. See also FIGS. 19-21.
Figure 12G:
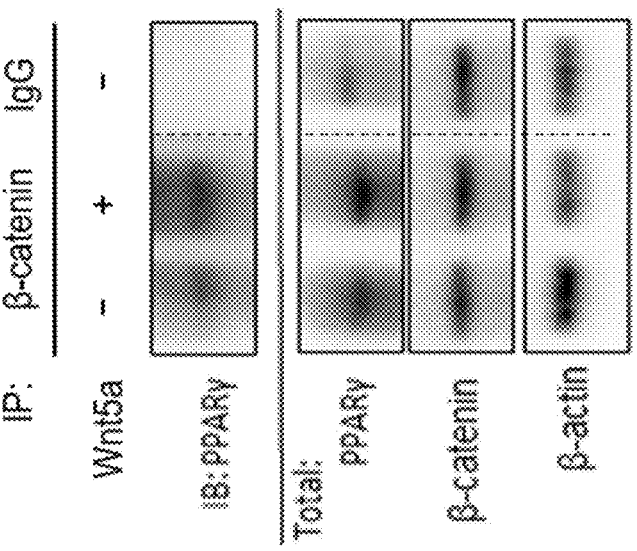
FIG. 12G shows Western blot analysis of PPARγ following β-catenin immunoprecipitation of Wnt5a-treated BMDCs. n=3.

Previous studies have described PPAR-γ to serve as a transcriptional co-activator in complex with β-catenin in the induction of genes that drive FAO (Jansson et al., 2005). We therefore performed endogenous co-immunoprecipitation experiments in primary DCs and also found PPAR-γ to bind to β-catenin upon Wnt5a stimulation (FIG. 12G). All together, these findings support a mechanism by which Wnt5a signaling promotes PPAR-γ-dependent induction of CPT1A to activate FAO in DCs (FIG. 12H).

Wnt5a-Induced Fatty Acid Oxidation Regulates the Enzymatic Activity of DC Indoleamine 2,3-Dioxygenase.

Figure 13B:
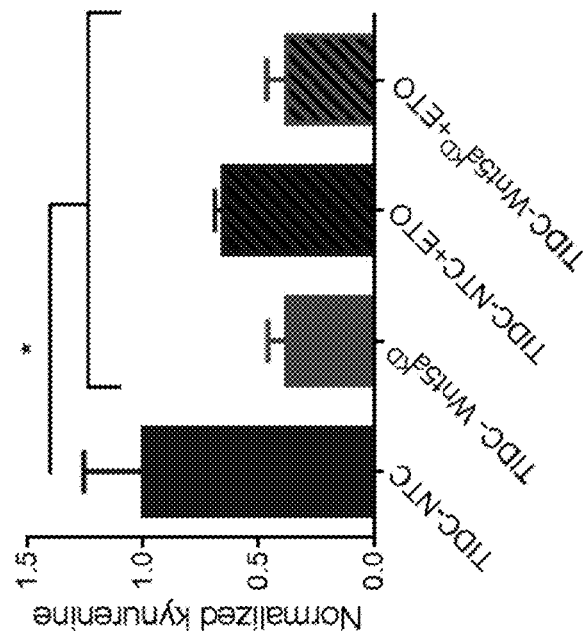
FIG. 13B shows kynurenine HPLC analysis of conditioned media harvested from TIDCs isolated from BRAF$^{V600E}$PTEN$^{-/-}$-NTC and BRAF$^{V600E}$PTEN$^{-/-}$—Wnt5a$^{KD}$ melanomas+/−ETO. n=3/group.
Figure 13A:
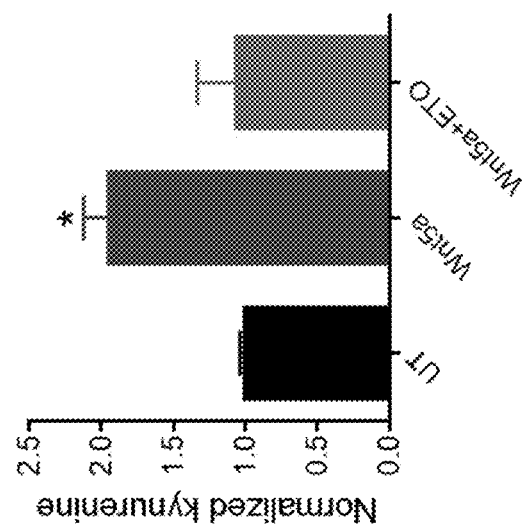
FIG. 13A shows kynurenine HPLC analysis of conditioned media harvested from DCs treated with Wnt5a or Wnt5a+ETO. n=3.

We, and others, have demonstrated the critical role of IDO in driving the development of Tregs and contributing to the establishment of an immunotolerant tumor microenvironment (Hanks et al., 2013; Holtzhausen et al., 2015; Munn et al., 2004). Despite inducing DC IDO expression, we found that Wnt3a stimulation failed to condition DCs to promote Treg differentiation (Holtzhausen et al., 2015). This led us to hypothesize that Wnt5a promotes IDO expression while also influencing the activity of this immunoregulatory enzyme. In light of the potent impact of DC FAO on DC-mediated Treg generation, we also hypothesized that Wnt5a-mediated regulation of FAO was directly modulating IDO enzymatic activity. In order to test this hypothesis, we measured the production of the IDO byproduct kynurenine in purified DC cultures using high performance liquid chromatography (HPLC). These studies confirmed that Wnt5a was capable of promoting DC IDO enzymatic activity and further demonstrated that the inhibition of DC FAO completely eliminated this effect, suggesting that DC FAO regulates the enzymatic activity of IDO (FIG. 13A). In order to demonstrate that this process also occurs within the melanoma microenvironment, we purified TIDCs from both resected BRAF$^{V600E}$-PTEN$^{-/-}$-NTC and BRAF$^{V600E}$-PTEN$^{-/-}$-Wnt5a$^{KD}$ tumors and analyzed their ability to generate kynurenine in culture as a surrogate for the enzymatic activity of IDO. This demonstrated that TIDCs derived from melanomas lacking Wnt5a expression exhibit lower levels of IDO enzyme activity similar to that observed in ETO-treated TIDCs purified from BRAF$^{V600E}$-PTEN$^{-/-}$-NTC control tumors (FIG. 13B). These findings show that the Wnt5a ligand plays a critical role in regulating DC IDO enzyme activity within developing melanomas and that this process is dependent upon the induction of FAO.

Figure 13C:
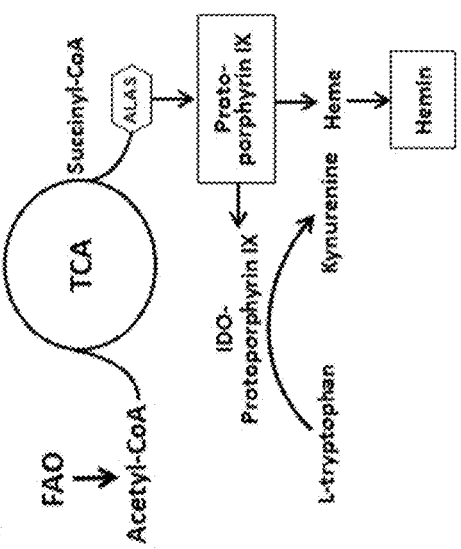
FIG. 13C shows a schematic of the hypothesized relationship between FAO, protoporphyrin IX (PpIX), and IDO enzymatic activity. TCA cycle, tricarboxylic acid cycle. ALAS, aminolevulinic acid synthase. Boxed intermediates measured.
Figure 13D:
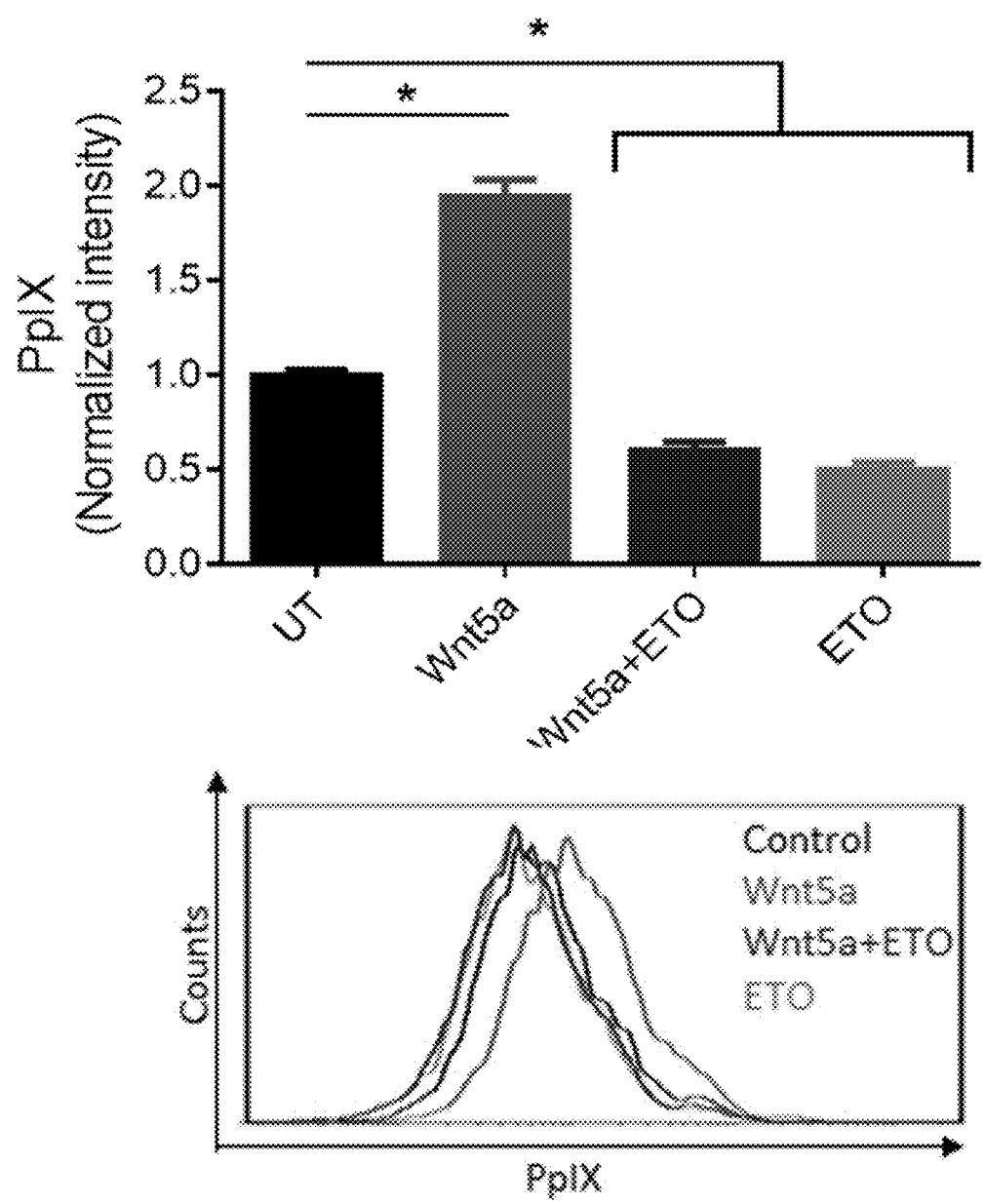
FIG. 13D shows PpIX flow cytometry analysis of DCs treated with Wnt5a, Wnt5a+ETO, or ETO following δ-aminolevulinic acid (ALA) pre-incubation. n=3. bottom, Representative flow histogram of PpIX expression levels.

Since the IDO apoenzyme requires the heme-derived PpIX prosthetic group for full enzymatic activity and the TCA cycle intermediate, succinyl CoA, serves as the primary substrate for heme synthesis, we conjectured that increased PpIX levels may partially explain why DC FAO drives IDO function (FIG. 13C). In order to investigate this potential mechanism, we studied the impact of Wnt5a on DC levels of PpIX and hemin, the heme breakdown product, using a modified flow cytometry technique and a colorimetric assay, respectively (Hryhorenko et al., 1998). This work demonstrated that Wnt5a enhances DC levels of the PpIX prosthetic group in a manner that depends on the induction of FAO (FIGS. 13D-13E). Notably, Wnt3a failed to enhance PpIX synthesis in DCs (FIG. 21B).

Consistent with this data, we have also determined the PGC-1α(PPAR-γ coactivator-1α)-dependent and rate-limiting enzyme of heme biosynthesis, aminolevulinic acid synthase-1 (ALAS1), to be upregulated in Wnt5a-stimulated DCs (FIGS. 13C, 13F) (Handschin et al., 2005). Indeed, further analysis showed Wnt5a, but not Wnt3a, to upregulate the expression of ALAS1 as well as several additional enzymes involved in PpIX synthesis, including ALA dehydrogenase, uroporphyrinogen III synthetase, coprophyrinogen III oxidase, and protoporphyrin III oxidase (FIGS. 13G, 21C).

These data indicate that Wnt5a promotes DC IDO enzymatic activity by enhancing flux through the heme biosynthetic pathway and promoting the synthesis of the PpIX prosthetic group. Overall, this work describes a novel link between cellular metabolism and the regulation of immune tolerance via the modulation of DC IDO activity and further demonstrate that melanomas manipulate this pathway in a Wnt5a-dependent manner.

Wnt5a-β-Catenin Induced Fatty Acid Oxidation is a Key Regulatory Pathway Underlying DC Tolerization.

Figure 14B:
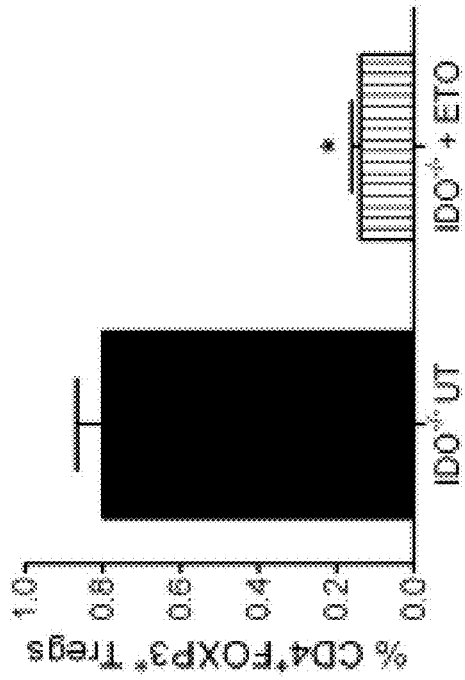
FIG. 14B shows in vitro Treg assay using IDO$^{-/-}$ BMDCs+/−ETO. n=3.
Figure 14D:
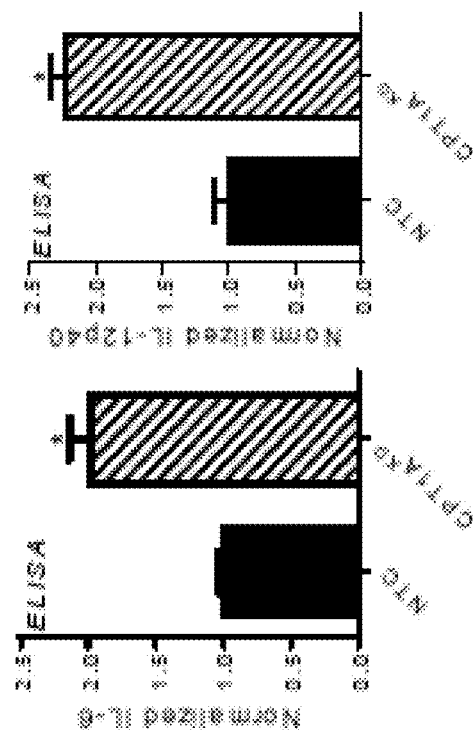
FIG. 14D shows ELISA analysis of IL-6, IL-12p40 levels in the conditioned media of DC2.4-NTC vs. DC2.4-CPT1A$^{KD}$ cell lines.
Figure 14A:
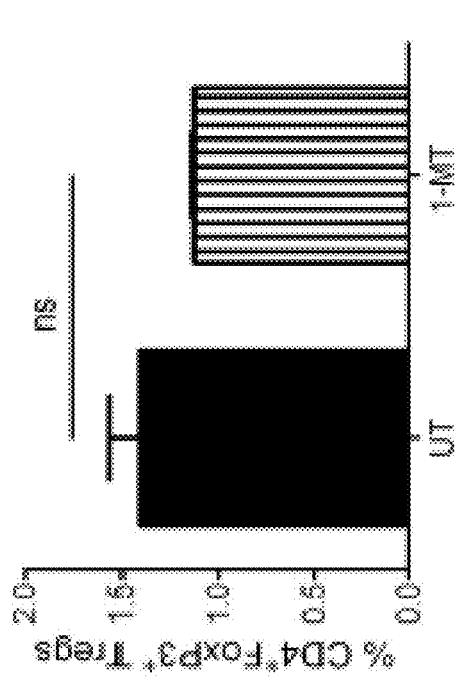
FIG. 14A shows in vitro Treg assay performed using DCs co-cultured with BRAF$^{V600E}$PTEN$^{-/-}$ conditioned media □□1-MT IDO inhibitor. ns, non-significant. n=3.

In previous experiments, we noted that 1-MT-mediated inhibition of IDO only modestly suppressed the ability of BRAF$^{V600E}$-PTEN$^{-/-}$ melanoma-derived conditioned media to promote DC-dependent Treg differentiation (FIG. 14A). We previously demonstrated that genetically silencing BRAF$^{V600E}$-PTEN$^{-/-}$ melanomas for Wnt5a expression significantly suppressed the DC-mediated Treg development in vitro and in vivo (Holtzhausen et al., 2015). Together, these findings suggest that Wnt5a-dependent DC tolerization is likely to also involve alternative mechanisms beyond IDO. We next sought to determine the relative impact of FAO and IDO on DC-mediated Treg development. In order to investigate this question, we performed in vitro Treg differentiation assays utilizing DCs derived from IDO$^{-/-}$ mice in the presence and absence of the CPT1A inhibitor, ETO. This data demonstrated FAO inhibition to dramatically suppress the ability of IDO$^{-/-}$ DCs to drive Treg differentiation, suggesting the presence of alternative IDO-independent pathways induced by FAO that support Treg development (FIG. 14B). This data supports the existence of additional mechanisms of DC-mediated Treg differentiation that are downstream of the Wnt5a-β-catenin-FAO signaling pathway.

Figure 14C:
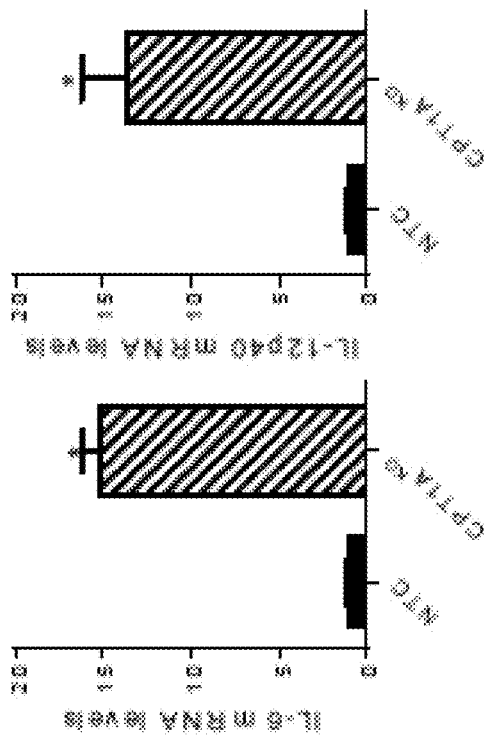
FIG. 14C shows qrt-PCR analysis of IL-6, IL-12 mRNA levels in DC2.4-NTC vs. DC2.4-CPT1A$^{KD}$ cells. n=3.

In order to investigate other potential mechanisms by which DC FAO can impact Treg differentiation, we turned to our previously described DC2.4-CPT1A$^{KD}$ cell line (FIG. 18). Since it is well known that the local cytokine milieu can influence naïve CD4$^+$ T cell differentiation into Tregs, we examined the effect of FAO on the DC cytokine expression profile by comparing the expression of several cytokines between the DC2.4-CPT1A$^{KD}$ cell line and the DC2.4-NTC control cell line based on qrt-PCR and ELISA. These experiments demonstrated that genetically silencing CPT1A to inhibit FAO results in significant elevations in the expression of the pro-inflammatory cytokines, IL-6 and IL-12, while no significant differences in the expression of IL-10 or TGF-β were noted (FIGS. 14C, 14D, data not shown). These alterations in cytokine expression were further recapitulated in primary DC populations exposed to the ETO CPT1A inhibitor (FIG. 14E). Additional studies confirmed that Wnt5a suppresses IL-6 and IL-12 expression in primary DCs, implicating the Wnt5a-β-catenin signaling pathway in the regulation of these pro-inflammatory cytokines (FIG. 14F). In order to demonstrate that melanoma-derived Wnt5a induced a similar DC cytokine expression profile in situ, we purified TIDCs from BRAF$^{V600E}$-PTEN$^{-/-}$-NTC and BRAF$^{V600E}$-PTEN$^{-/-}$-Wnt5a$^{KD}$ tumors as above and quantitated both IL-6 and IL-12p40 expression by qrt-PCR. These studies supported our previous findings in that BRAF$^{V600E}$-PTEN$^{-/-}$ melanomas genetically silenced for Wnt5a were associated with significant elevations in TIDC IL-6 and IL-12p40 expression (FIG. 14G). Together, this work suggests that in addition to stimulating IDO enzymatic activity, DC FAO also suppresses IL-6 and IL-12 expression, creating an environment that favors the generation of Tregs. Based on previous studies demonstrating that IL-6 promotes the proteosomal degradation of IDO, these data suggest that DC FAO may also promote IDO stabilization (Grohmann et al., 2001; Orabona et al., 2008). These dual mechanisms of IDO regulation suggest a central role for the Wnt5a-β-catenin signaling pathway in DC tolerization.

Inhibition of Fatty Acid Oxidation Enhances Anti-PD-1 Antibody Therapy and Suppresses the Progression of an Autochthonous Melanoma Model.

Figure 15A:
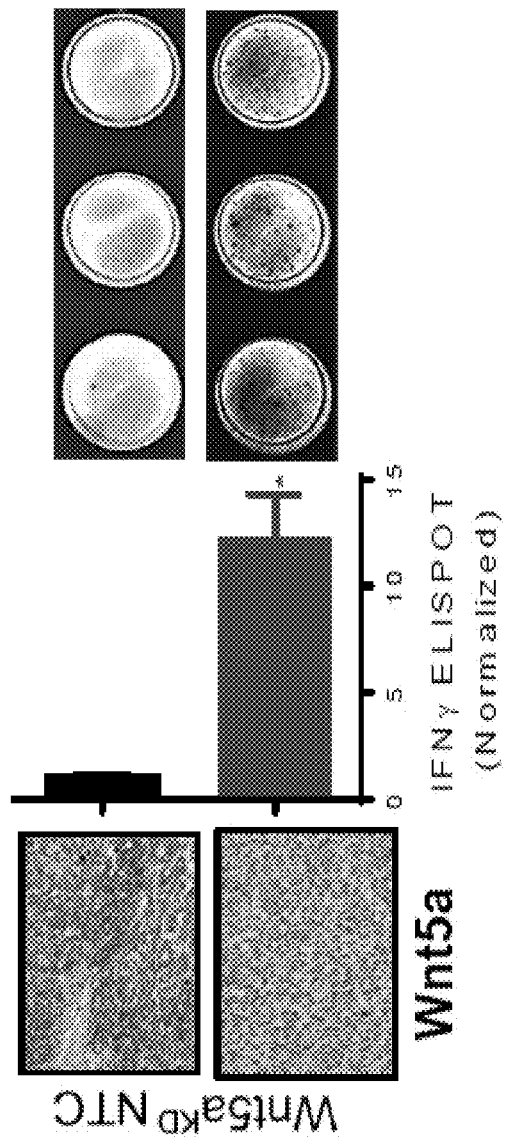
FIG. 15A shows FAO Inhibition Augments the Efficacy of anti-PD-1 Antibody Immunotherapy and Reverses DC Tolerization in a Transgenic Melanoma Model. IFN-γELISPOT analysis of tumor-infiltrating T cells derived from BRAF$^{V600E}$PTEN$^{-/-}$-NTC or -Wnt5a$^{KD}$ melanomas. n=3/group. left Wnt5a IHC of resected BRAF$^{V600E}$PTEN$^{-/-}$-NTC or -Wnt5a$^{KD}$ melanoma tissues (20×). right, representative IFN-γELISPOT plate.
Figure 15B:
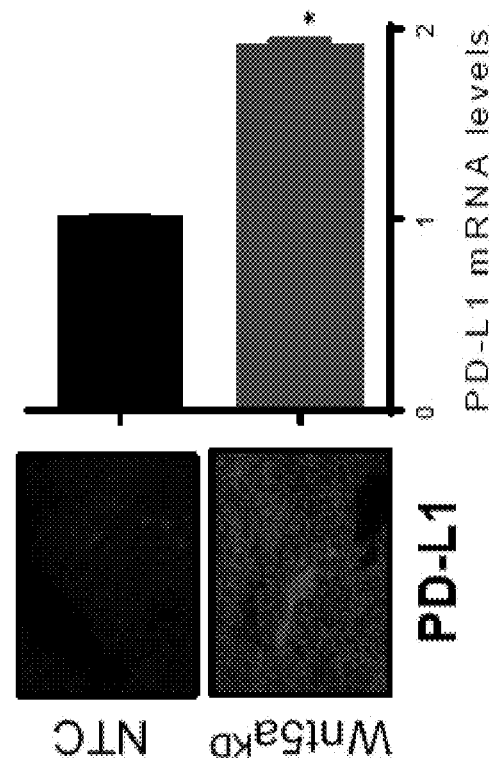
FIG. 15B shows PD-L1 qrt-PCR analysis and IF analysis of BRAF$^{V600E}$PTEN$^{-/-}$-NTC and BRAF$^{V600E}$PTEN$^{-/-}$-Wnt5a$^{KD}$ melanomas (20×). n=3/group.
Figure 15C:
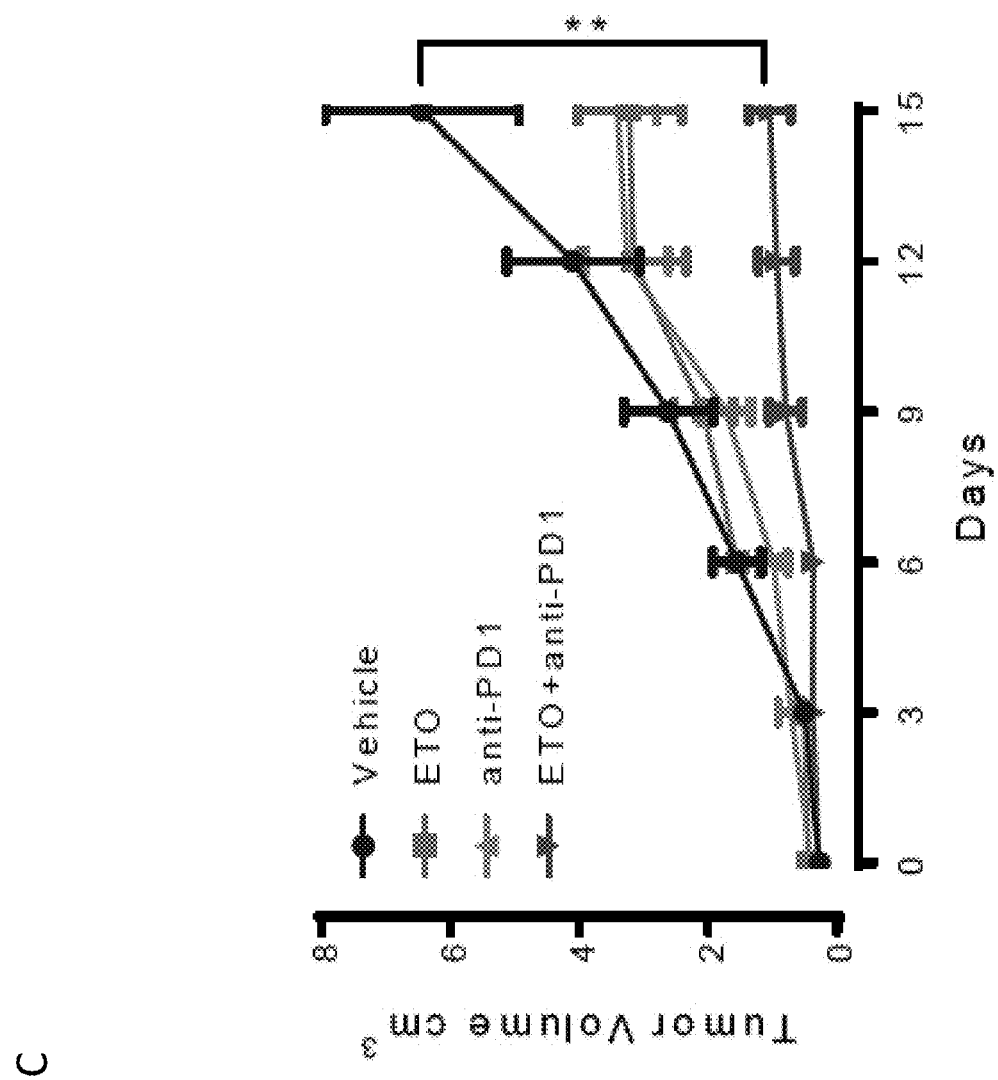
FIG. 15C shows BRAF$^{V600E}$PTEN$^{-/-}$ melanoma growth in C57BL/6 mice undergoing treatment with vehicle and IgG isotype control, ETO and IgG isotype control, anti-PD-1 ab and vehicle control, or anti-PD-1 ab and ETO. n=6/group.
Figure 15E:
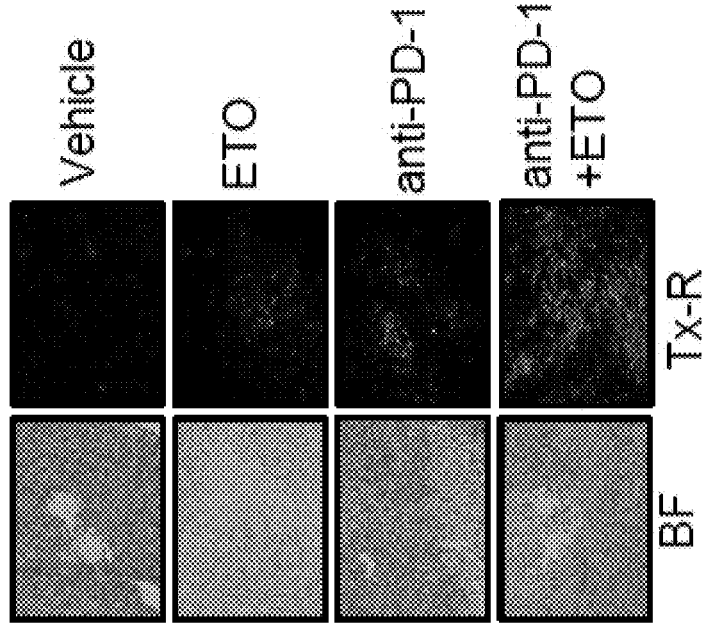
FIG. 15E shows CD8$^+$ TIL IHC/IF analysis of BRAF$^{V600E}$PTEN$^{-/-}$ melanomas resected from mice undergoing the indicated treatment regimen (20×). BF, brightfield. Tx-R, Texas Red. Representative of three tumors/group.
Figure 15D:
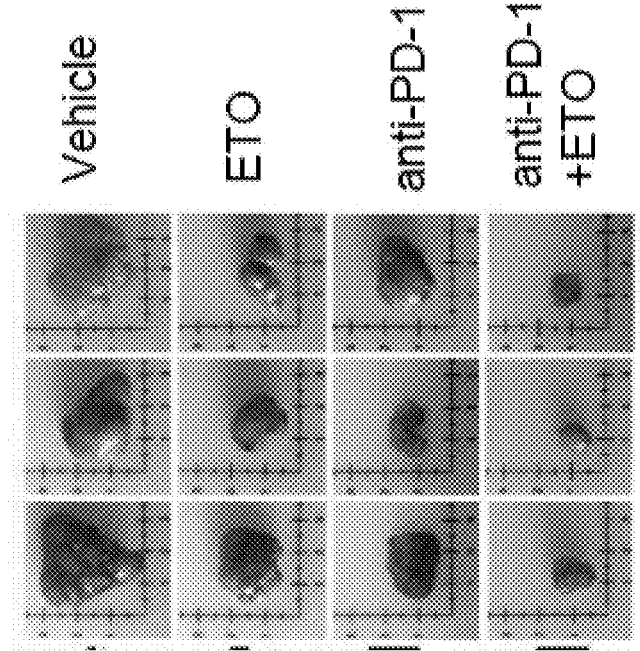
FIG. 15D shows representative tumors of each treatment group from 15C.
Figure 15F:
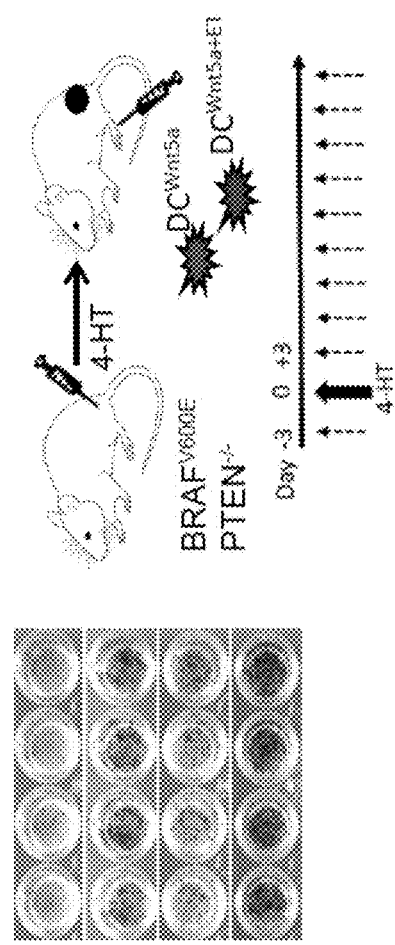
FIG. 15F shows IFNγ ELISPOT analysis of TRP2-specific tumor-infiltrating T cells isolated from each treatment group from 15C. n=4/group. right, IFN-γ ELISPOT plate.
Figure 22B:
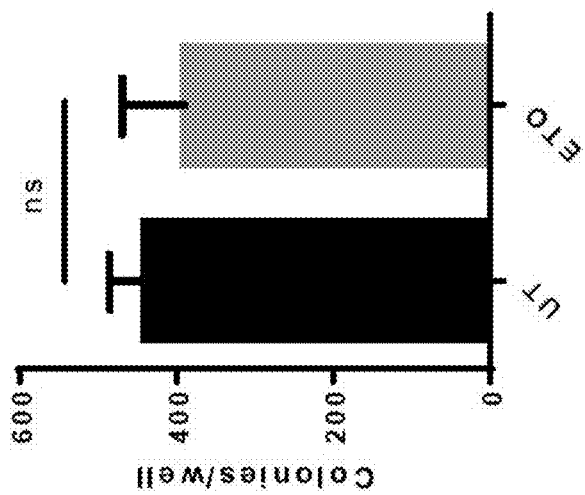
FIG. 22B shows quantitation of colonies from FIG. 22A.
Figure 22A:
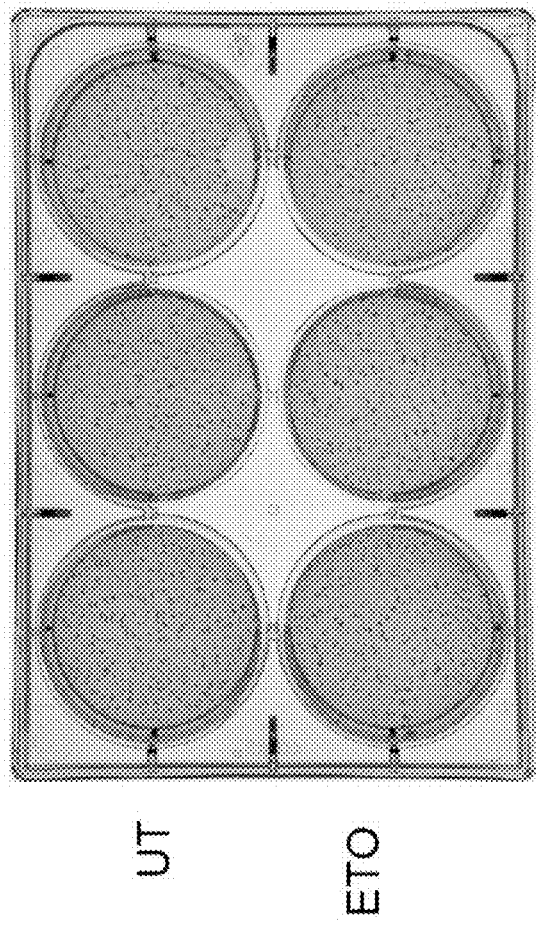
FIG. 22A shows BRAFV600EPTEN−/− cells were allowed to form colonies in soft agar for 15 days in the presence or absence of ETO, then stained with MTT for viable colonies.

The previous results suggest that a paracrine signaling axis mediated by melanoma-expressed Wnt5a induces local DC FAO to promote the generation of an immunotolerant microenvironment. In order to assess the impact of melanoma Wnt5a expression on the development of T cell activity in melanoma, we performed IFN-γ ELISPOT assays on unstimulated tumor-infiltrating lymphocytes (TILs) harvested from BRAF$^{V600E}$-PTEN$^{-/-}$-NTC and BRAF$^{V600E}$-PTEN$^{-/-}$-Wnt5a$^{KD}$ tumors. These experiments showed a significant enhancement in IFN-γ-expressing TILs within BRAF$^{V600E}$-PTEN$^{-/-}$-Wnt5a$^{KD}$ tumors compared with control tumors, further supporting the immunotolerant role of Wnt5a in melanoma (FIG. 15A). These findings were also associated with elevated levels of PD-L1 expression based on qrt-PCR and immunofluorescence analysis of resected BRAF$^{V600E}$-PTEN$^{-/-}$-Wnt5a$^{KD}$ tumor tissues (FIG. 15B). Since previous studies have indicated that an inflamed tumor environment characterized by elevated PD-L1 expression is associated with improved responses to anti-PD-1 antibody checkpoint inhibitor therapy, we hypothesized that pharmacological inhibition of FAO by targeting CPT1A downstream of Wnt5a would augment anti-PD-1 antibody immunotherapy (Spranger et al., 2013). Our previous data has indicated that ETO treatment of BRAF$^{V600E}$-PTEN$^{-/-}$ tumor cells has no impact on the intrinsic proliferative capacity of this tumor model (FIG. 22). Therefore, any impact of ETO on the efficacy of anti-PD-1 antibody therapy would likely involve the stimulation of anti-tumor immunity. In order to test this hypothesis, we implanted BRAF$^{V600E}$-PTEN$^{-/-}$ melanoma cells by subcutaneous injection in syngeneic C57BL/6 mice. Once these primary melanomas reached an average volume of 80-100 mm$^3$, the host mice were treated with either vehicle only, the ETO inhibitor, anti-PD-1 antibody, or both. Primary tumor volumes were monitored and melanoma antigen-specific CD8+ T cell responses were quantified by IFN-γ ELISPOT assays. These data showed that ETO-mediated CPT1A inhibition suppresses the progression of BRAF$^{V600E}$-PTEN$^{-/-}$ melanoma similar to anti-PD-1 antibody monotherapy while combination anti-PD-1 antibody/ETO therapy resulted in a significant reduction in primary melanoma growth (FIGS. 15C, 15D). This inhibition in primary melanoma progression also correlated with enhanced numbers of CD8$^+$ TILs in combination anti-PD-1 antibody/ETO-treated tumors as well as a more pronounced induction of TRP2-specific CD8$^+$ T cells suggesting this synergism to be dependent on the induction of an effective anti-tumor T cell response (FIGS. 15E, 15F). These results support our previous findings indicating that FAO modulates anti-tumor immunity and is consistent with our previous data suggesting that the inhibition of the Wnt5a-β-catenin signaling pathway in DCs represents a novel strategy for augmenting checkpoint inhibitor efficacy (Holtzhausen et al., 2015).

Figure 15G:
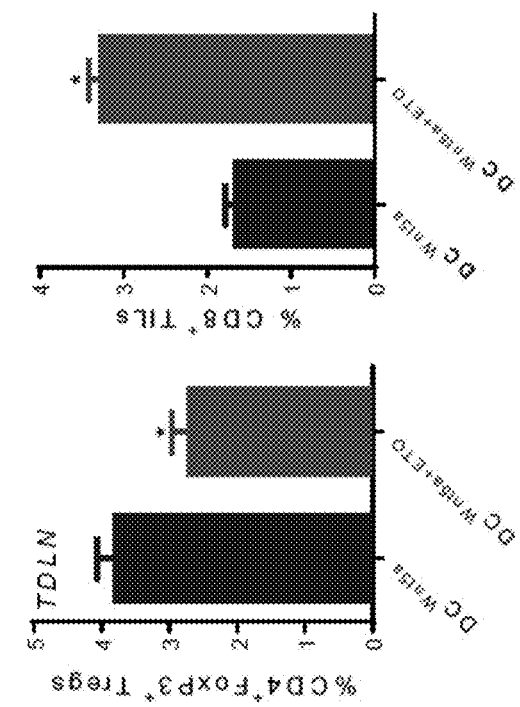
FIG. 15G is a schematic of the investigation of DC-specific FAO on primary melanoma progression in an autochthonous BRAF$^{V600E}$PTEN$^{-/-}$ model. Pre-treated DCs adoptively transferred to the footpad of syngeneic BRAF$^{V600E}$PTEN$^{-/-}$ mice 3 days prior to 4-HT delivery to the base of the tail and every 3 days thereafter for 4 weeks.
Figure 15H:
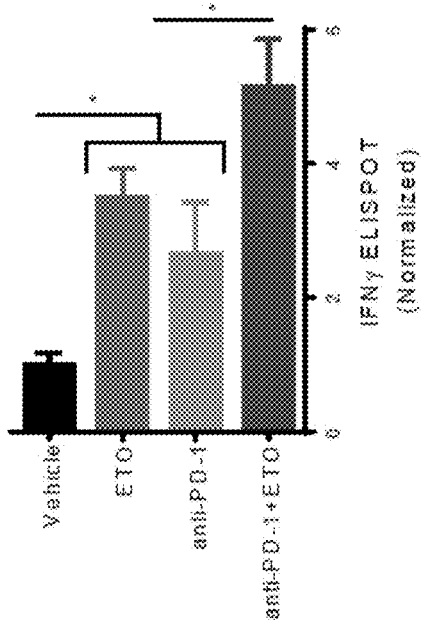
FIG. 15H shows the results of the investigation of FIG. 15G.
Figure 15I:
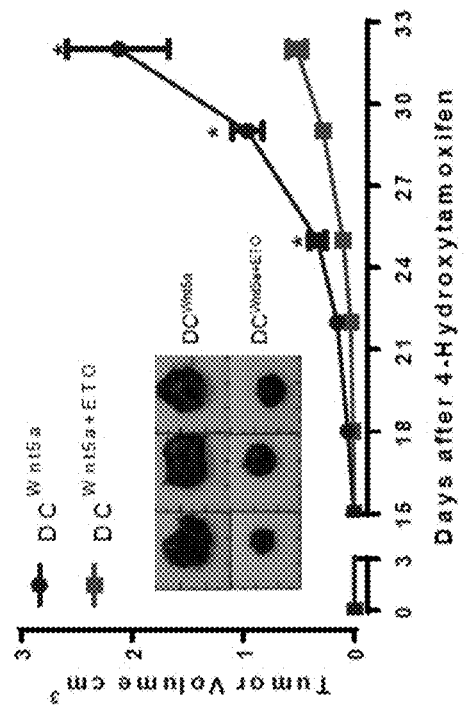
FIG. 15I shows shared inguinal lymph node tissue and primary melanoma tissue was analysed for CD4+ FoxP3+ Treg and CD3+CD8+ T cell populations by fow cytometry, respectively. n=4. All data is mean+/−S.D. See also FIG. 22.

In order to investigate the specific impact of DC FAO modulation on melanoma progression, primary DCs were treated with Wnt5a in the presence and absence of ETO followed by their transfer into the draining lymph node bed of developing autochthonous melanomas in the BRAF$^{V600E}$-PTEN$^{-/-}$ transgenic model (FIG. 15G). Consistent with our previous work, this experiment demonstrated DC-specific FAO inhibition to potently suppress primary melanoma progression (FIG. 1511). Correlative studies showed this effect to also coincide with a suppression of Tregs within draining LN tissues and enhanced numbers of melanoma-infiltrating CD8+ T cells (FIG. 15I). Together, these data suggest the Wnt5a-β-catenin-PPAR-γ-CPT1A signaling axis to be a novel target for enhancing the efficacy of cancer immunotherapy.

Discussion

In light of the critical role of the DC in driving effective anti-tumor immunity, we have focused on elucidating those tumor-derived mechanisms that impair DC function (Gabrilovich, 2004). Indeed, there is now emerging evidence implicating a role for DC tolerization in the establishment of an immune privileged site that facilitates tumor progression (Hanks et al., 2013; Scarlett et al., 2012). This report demonstrates that melanomas induce local immune tolerance by manipulating the metabolism of DCs within the tumor microenvironment via a paracrine Wnt-β-catenin signaling pathway. Opposed to recently described theories that the upregulation of IDO strictly represents a negative feedback mechanism of adaptive anti-tumor immunity (Spranger et al., 2013), we define an immune evasion mechanism that has evolved to manipulate both IDO functionality and the cytokine milieu within the tumor microenvironment.

Previous studies have suggested that DC tolerization is dependent upon the β-catenin signaling pathway however the mechanism(s) by which tumors control this DC tolerization program and how this pathway ultimately drives immune tolerance has remained unclear (Jiang et al., 2007; Manicassamy et al., 2010). A more complete understanding of these mechanisms could provide more selective pharmacological targets for reversing the establishment of an immunotolerant microenvironment. We recently demonstrated that melanoma expression of the Wnt5a ligand triggers β-catenin-dependent induction of DC IDO expression via a paracrine signaling pathway and that this culminates in driving local Treg differentiation (Holtzhausen et al., 2015). Our previous data suggested that the Wnt-β-catenin pathway likely promoted the DC tolerization program via additional uncharacterized mechanisms and others have highlighted the importance of cellular metabolism in the regulation of DC function with findings showing that TLR-induced DC maturation is critically dependent upon glycolysis and that OXPHOS promotes the development of a pro-tolerogenic state (Everts et al., 2014; Krawczyk et al., 2010; Malinarich et al., 2015). Additional studies have described a role for Wnt5a in the regulation of cellular metabolism (Sherwood et al., 2014). Based on these findings, we hypothesized that melanoma expressed Wnt5a metabolically reprograms DCs and that this may function as a central mechanism of tumor-mediated immune tolerance.

The data presented here, indeed, demonstrate that melanoma-derived Wnt5a robustly shifts DCs toward OXPHOS in a manner which is dominant over LPS-induced glycolysis (Everts et al., 2014). Other investigators have suggested that AMPK likely plays an important role in shifting DC metabolism from glycolysis to an OXPHOS-favored state. While we also found AMPK activation to inhibit DC glycolysis, our data suggests that Wnt5a-mediated metabolic re-programming of DCs is independent of AMPK. After determining that Wnt5a-stimulated DCs were not reliant on glutamine as an energy source for undergoing tolerization and noting that Wnt5a-stimulated DCs exhibit both enhanced fatty acid uptake and greater lipid stores, we reasoned that DC FAO was critical for driving this phenotype. Notably, a role for FAO in DC tolerance would also be consistent with the metabolic alterations observed in M2 macrophages, another myeloid-derived cell type that has been associated with tumor progression (Allavena et al., 2008; O'Neill and Pearce, 2016). Indeed, the inhibition of FAO by either a pharmacologic or genetic approach dominantly inhibited DC-mediated Treg generation and potently promoted DC-dependent stimulation of CD8+ T cell proliferation. Additional studies elucidated the underlying mechanism of Wnt5a-induced DC FAO to involve PPAR-γ-mediated expression of CPT1A and for this process to depend on β-catenin. We further demonstrate that β-catenin and PPAR-γ form a co-transcriptional activator complex in primary DCs upon Wnt5a exposure. These findings are consistent with previous studies that have demonstrated a role for PPAR-γ as playing a role in the transcriptional activation of several genes involved in DC FAO (Szatmari et al., 2007). In light of the previously described complex involving PPAR-γ and retinoic acid X receptor-α (RXRα) (Kratzner et al., 2008), this pathway may provide a link between these data and the recently described role of β-catenin-dependent induction of DC vitamin A metabolism in Treg differentiation (Hong et al., 2015; Szatmari et al., 2006).

While the cellular oxidative state has been shown to regulate IDO enzyme activity, to our knowledge a relationship between metabolic regulation and the enzymatic activity of IDO has not been appreciated (Thomas et al., 2001). Here, we show that Wnt5a drives heme biosynthesis and the accumulation of the PpIX prosthetic group of IDO by both driving TCA flux and promoting the upregulation of the expression of several enzymes involved in this pathway including the rate limiting enzyme, aminolevulinic acid synthase (ALAS) (Hunter and Ferreira, 2011). Since PpIX is a limiting factor of IDO activity (Thomas et al., 2001), we propose that this pathway is a previously unrecognized mechanism of IDO regulation. Determining whether other metabolic alterations are also contributing to this phenomenon is an active area of investigation.

Our data also indicates that DC FAO has a broader impact on the DC tolerization process that extends beyond IDO. This line of inquiry led us to discover that this metabolic shift potently suppresses two key pro-inflammatory cytokines, both IL-6 and IL-12, which contribute to a more favorable mileu for driving Treg differentiation. In particular, IL-6 has been shown to antagonize Treg development in several experimental systems while promoting $T_H17$ differentiation. Interestingly, previous studies have found IL-6 to promote the proteosomal degradation of IDO, also mitigating against the development of Tregs (Orabona et al., 2008). The exact mechanism by which the Wnt5a-β-catenin-PPAR-γ signaling pathway drives these alterations in DC cytokine expression are unclear however PPAR-γ-dependent alterations in DC cytokine expression have been described and likely contribute to the downregulation of IL-6 and IL-12 observed in this work (Nencioni et al., 2002). Given that our findings indicate that DC FAO can influence multiple biochemical pathways important for achieving DC tolerization, we speculate that targeting key regulators of DC FAO could generate a potent impact on the tumor immune microenvironment. Indeed, we demonstrate that the inhibition of DC FAO is capable significantly suppressing melanoma progression in a poorly immunogenic transgenic model of melanoma. Together, these data suggest that targeting the Wnt5a-β-catenin-FAO pathway may represent a promising strategy for augmenting checkpoint inhibitor immunotherapy. This would be consistent with the robust affect generated by combining a CPT1A-targeted inhibitor with anti-PD-1 antibody therapy in the BRAFv $I_N$ melanoma model. Further, since the Wnt5a-β-catenin-FAO pathway regulates several components of DC tolerization that extend beyond IDO, we propose that designing strategies to inhibit this pathway upstream of IDO may be more effective at inducing anti-tumor immunity than strictly targeting the activity of this enzyme. We are conducting additional studies to confirm this hypothesis. Melanomas associated with few tumor-infiltrating lymphocytes (TILs) and that exhibit signs of a generally non-inflamed microenvironment are poorly responsive to checkpoint inhibitor therapy (Ji et al., 2012). In line with our mechanistic DC studies, recent gene expression profiling based on microarray and RNAseq datasets have demonstrated that primary melanomas, as well as other solid tumors, are associated with elevated levels of β-catenin and PPAR-γ signaling (Spranger et al., 2015; Sweis et al., 2016). Despite this finding, a minority of these 'TIL-poor' cancers exhibit genomic mutations that drive the β-catenin signaling pathway (Luke et al., 2016), suggesting that Wnt-mediated paracrine signaling pathways contribute significantly to the elevated β-catenin activation state observed in these non-inflamed tumors. In this work, we provide functional data indicating that Wnt5a promotes the establishment of an immune privileged, 'TIL-poor' melanoma microenvironment by driving DC FAO. The importance of Wnt5a in promoting an immune tolerant state is supported by a recent report employing RNAseq differential gene expression analysis demonstrating Wnt5a as one of the most significantly upregulated genes in melanomas refractory to pembrolizumab immunotherapy (Hugo et al., 2016).

Alltogether, these findings indicate that DC tolerization in the tumor microenvironment is capable of contributing to immunotherapy resistance and suggest that Wnt ligand antagonism would be a promising strategy for augmenting anti-PD-1 antibody immunotherapy. Finally, these data further advocate for DC-specific manipulation of the FAO pathway as a novel approach for designing the next generation of DC-based cancer vaccines.

Experimental Procedures

T Cell Proliferation Assay.

Splenocytes of OT-1 mice (H-$2^b$) were isolated and stained with CellTrace Violet (ThermoFisher). Preconditioned DCs were loaded with ovalbumin peptide SIINFEKL, and co-cultured at a DC:splenocyte ratio of 40,000:120,000 cells for 72 hrs. CD8+ T cell proliferation was measured by the dilution of Cell Trace Violet dye by flow cytometry.

Treg Assays.

In vivo Treg assay. DCs (C57, H-$2^b$) were pre-treated for 48 hours and delivered by intradermal injection into the footpad of Foxp3-mRFP mice. Draining inguinal and popliteal lymph nodes were resected 5 days later and analyzed for CD4+ Foxp3+ Tregs. In vitro Treg assay, DCs (Balb/c, H-$2^d$) were pre-treated for either 24 or 48 hrs, and re-plated at a 1:3 DC:T-cell ratio with purified naïve Foxp3-mRFP(H-$2^b$) CD4+ Tcells. These co-cultures were incubated for 6 days and quantitated for CD4+ FoxP3+ Tregs by flow cytometry.

BODIPY and Fatty Acid Uptake Assay.

Dendritic Cells were stained in 0.5 µg/ml BODIPY 493/503 in PBS for 15 min to determine neutral lipid content (Herber et al., 2010). Fatty acid uptake measurement in DCs were performed using a dodecanoic acid fluorescent TF2-C12 fatty acid (Sigma) according to the manufacturer's protocol.

Lactate Measurement.

L-Lactate levels were measured by lactate dehydrogenase conversion of L-lactate+NAD$^+$ to pyruvate+NADH following treatment with hydralazine (Pesce et al., 1975). Lactate standards and samples were read at NADH specific absorbance 340 nm.

Cellular Energy Metabolism Analysis.

DC energy metabolism was measured using the XF$^e$24 extracellular flux analyzer (Seahorse Bioscience), with the glycolysis stress test kit and the mitochondrial stress test kit as previously described (Everts et al., 2014; Zhao and Klimecki, 2015).

IDO Enzymatic Assay and Hemin Assay.

DC IDO enzyme activity was measured by the conversion of L-tryptophan to L-kynurenine in conditioned media by HPLC (Pallotta et al., 2011). Intracellular hemin levels were measured using a colorimetric assay kit (BioVision).

PpIX Analysis.

Dendritic cells were terminally incubated in the presence of 1 mM δ-aminolevulinic acid (ALA) for 4 hrs. Intracellular PpIX was analyzed by flow cytometry as previously described (Hryhorenko et al., 1998).

Mice.

C57BL/6J (C57, H-2b), BALB/cJ (H-2d), B6.Cg-BraftmlMmcm PtentmlHwu Tg(Tyr-cre/ERT2 H-2b)13Bos/BosJ (BRAFV600EPTEN−/−, H-2b), C57BL/6-Tg(TcraTcrb) 1100Mjba (OT-1, H-2b), B6.129-Ido1tm1A1ma (IDOKO, H-2b) mice were purchased from Jackson Labs. C57BL/6-Foxp3tm1F1v/J (Foxp3-mRFP, H-2b) mice were a generous gift from H. K. Lyerly (Duke University Medical Center). Experiments were performed based on a protocol approved by the Institutional Animal Care and Use Committee at Duke University Medical Center.

Cell Culture and Establishment of Stable Cell Lines.

Murine bone marrow-derived DCs (BMDCs) were harvested and differentiated as previously described [1] and purified using CD11c microbeads (Miltenyi Biotec) according to manufacturer's protocol. DC purity was monitored by flow cytometry and consistently found to be >95% CD11c+ F4/80-. BRAFV600EPTEN−/−Wnt5aKD and BRAFV600EPTEN−/−NTC cell lines were generated and cultured as previously described [2]. DC2.4, a murine dendritic cell line was kindly provided by Dr. Kenneth L. Rock (University of Massachusetts Medical School), and cultured as previously described [3]. DC2.4β-cateninKD, DC2.4-CPT1AKD, and DC2.4-NTC stable cell lines were generated using a β-catenin-targeted, CPT1A-targeted, or control shRNA-expressing lentivirus followed by puromycin selection. DCs were treated with Wnt3a (100 ng/mL), Wnt5a (200 ng/mL), LPS (1 µg/mL), 1-MT, 2DG (1 mM), or ETO (100 □M) vs vehicle control either for 24 or 48 hrs prior to their use in both in vitro and in vivo experiments.

Antibodies, Immunoprecipitation, and Immunoblot Analysis.

Primary antibodies including CPT1A (Cell signaling), PPAR-γ (Santa Cruz Biotechnology), β-catenin, β-actin (Millipore), p-AMPK(T172)/AMPK (Cell signaling), p-AKT(T308)/Akt (Cell Signaling) were used at 1:1000. Secondary antibodies including goat anti-rabbit IgG-HRP (Millipore) and goat anti-mouse IgG-HRP (Millipore) were used at 1:5000. Cells were lysed in Laemmli sample buffer after treatment and subjected to SDS-polyacrylamide gel electrophoresis and immunoblot analysis. For immunoprecipitation, cells were lysed in radio immunoprecipitation assay (RIPA) buffer [10 mM sodium phosphate (pH 8.0), 150 mM NaCl, 1% Triton X-100, 1% sodium deoxycholate, and 0.1% SDS in the presence of 1 mM DTT, 1 mM phenylmethylsulfonylfluoride, and a protease inhibitor cocktail (Sigma)], precleared with protein A beads, and then incubated with 1 µg of antibody against β-catenin or isotype control IgG with protein A-agarose beads on a rotator overnight at 4° C. After 3 washes with RIPA buffer, immunoprecipitated complexes were eluted in sample buffer by boiling and subjected to immunoblot analysis. Immunoblots were visualized by chemiluminescence substrate (ThermoFisher) and imaged by a ChemiDoc XRSplus system (Bio-Rad).

Flow Cytometry.

Cells were stained with fluorochrome conjugated antibodies or commercially available dyes according to the standard protocols and analyzed using a FACSCanto II or LSRII (Becton Dickinson).

RNA Isolation, RT-qPCR, qPCR Array.

Total RNA was isolated by RNeasy Plus Mini Kit(Qiagen). RNA(500 ng) was used in cDNA Synthesis (iScript, BioRad). Quantification of mRNA for genes involved in PPARγ signaling was performed using Mouse PrimePCR PPAR Array according to the manufacturer's protocol (BioRad). Real-time PCR was performed using an ABI7500 Real-Time PCR system (Life Technologies). Data analysis utilized the PrimePCR Analysis Software (BioRad). Conventional qPCR was performed using validated primers (Table 1) and SsoAdvanced Universal SYBR Green Super mix (BioRad) or Taqman probes (Applied Biosystems) for heme synthesis enzymes.

TABLE 1

Primer Sequences Used for SYBR Green Real-Time PCR. Forward primer indicated as "for", and reverse primer indicated as "rev". All murine species specific.

| Gene Name | Primer Sequence (5'-3') |
|---|---|
| mACTB-for | GGCTGTATTCCCCTCCATCG (SEQ ID NO: 3) |
| mACTB-rev | CCAGTTGGTAACAATGCCATGT (SEQ ID NO: 4) |
| mPPARγ-for | GCCCTTTGGTGACTTTATGGA (SEQ ID NO: 5) |
| mPPARγ-rev | GCAGCAGGTTGTCTTGGATG (SEQ ID NO: 6) |
| mCPT1A-for | CTCAGTGGGAGCGACTCTTCA (SEQ ID NO: 7) |
| mCPT1A-rev | GGCCTCTGTGGTACACGACAA (SEQ ID NO: 8) |
| mCPT1B-for | TTCAACACTACACGCATCCC (SEQ ID NO: 9) |
| mCPT1B-rev | GCCCTCATAGAGCCAGACC (SEQ ID NO: 10) |
| mCPT1C-for | TCTTCACTGAGTTCCGATGGG (SEQ ID NO: 11) |
| mCPT1C-rev | ACGCCAGAGATGCCTTTTCC (SEQ ID NO: 12) |
| mIL6-for | TAGTCCTTCCTACCCCAATTTCC (SEQ ID NO: 13) |
| mIL6-rev | TTGGTCCTTAGCCACTCCTTC (SEQ ID NO: 14) |
| mIL10-for | GACCAGCTGGACAACATAC (SEQ ID NO: 15 |
| mIL10-rev | CTGGAGTCCAGCAGACTC (SEQ ID NO: 16) |
| mIL12B-for | GAACACATGCCCACTTGCTG (SEQ ID NO: 17) |
| mIL12B-rev | CGTGCTCATGGCTGGTGCAAAG (SEQ ID NO: 18) |
| mTGFβ-for | GCAACAACGCCATCTATGAG (SEQ ID NO: 19) |
| mTGFβ-rev | ATCTTTGCTGTCACAAGAGC (SEQ ID NO: 20) |
| mPFK-for | GGAGGCGAGAACATCAAGCC (SEQ ID NO: 21) |

TABLE 1-continued

Primer Sequences Used for SYBR Green Real-Time PCR. Forward primer indicated as "for", and reverse primer indicated as "rev". All murine species specific.

| Gene Name | Primer Sequence (5'-3') |
|---|---|
| mPFK-rev | CGGCCTTCCCTCGTAGTGA (SEQ ID NO: 22) |
| mHK3-for | TGCTGCCCACATACGTGAG (SEQ ID NO: 23) |
| mHK3-rev | GCCTGTCAGTGTTACCCACAA (SEQ ID NO: 24) |
| mCTNNB-for | TCCCATCCACGCAGTTTGAC (SEQ ID NO: 25) |
| mCTNNB-rev | TCCTCATCGTTTAGCAGTTTGT (SEQ ID NO: 26) |
| mALAS1-for | GATGCCAGGCTGTGAAATTTACT (SEQ ID NO: 27) |
| mALAS1-rev | CTGTTGCGAATCCCTTGGAT (SEQ ID NO: 28) |
| mGAPDH-for | GTC TAC ATG TTC CAG TAT GAC TCC (SEQ ID NO: 29) |
| mGAPDH-rev | AGT GAG TTG TCA TAT TTC TCG TGG T (SEQ ID NO: 30) |

Murine Cell Isolation.

Spleens were digested with spleen dissociation buffer (Stemcell Technologies). Tumors were resected and mechanically disaggregated by gentleMACS (Miltenyi) and digested with collagenase IV, hyaluronidase, and deoxyribonuclease (Sigma) at 37° C. for 1 hour. A 40-micron filter was used to obtain a single cell suspension for downstream applications. DCs were purified using CD11c microbeads and naïve CD4 T cells were obtained using a naïve T cell isolation kit (Stemcell Technologies). All cell populations were verified for purity by flow cytometry based on a CD45+CD11c+F4/80− and a CD3+CD4+CD62L+ profile, respectively.

Human Monocyte-derived Dendritic Cells were generated as previously described [4].

ELISPOT.

Mouse IFNγ ELISPOTPLUS (MABTECH) was performed according to manufacture guidelines. Imaging was conducted using a ChemiDoc System (BioRad) and quantified using ImageJ software.

ELISA.

Murine IL-6 (eBioscience) and IL-12p40 (Becton Dickinson) ELISAs were performed according to manufacture's protocol.

Immunohistochemistry/Immunofluorescence.

Paraffin-embedded tissues were processed and stained following standard protocols and imaged with a Zeiss CLSM 700 confocal microscope. CD8 (BioLegend) and PD-L1 (Abcam) primary antibodies were utilized where indicated. Warp Red chromogen detection system (BioCare) was used for antigen visualization.

Syngeneic Transplant Tumor Studies.

BRAFV600EPTEN−/− cells line were established as previously described [2]. 5×105 cells were implanted by subcutaneous injection into syngeneic C57 mice. Tumor growth was monitored by caliper measurement. Etomoxir (Sigma, ETO) was administered daily by oral gavage (25 mg/kg/day)

[5]. Anti-PD-1 rat mAb or rat IgG2a isotype control (BioX-Cell) was delivered every 3 days by intraperitoneal injection (250 µg/dose).

Autochthonous Tumor Studies.

B6.Cg-Braftm1Mmcm Ptentm1Hwu Tg(Tyr-cre/ERT2 H-2b)13Bos/BosJ (BRAFV600EPTEN−/−, H-2b), transgenic mice were subdermally injected with 4-HT (Sigma, 38.75 µg/mice) to induce primary melanoma development. Three days prior to 4-HT injection, 1×106 cells DCs pretreated with Wnt5a+/−ETO were washed and delivered by intra-dermal injection into the hind leg foot pads every 3-4 days until the conclusion of the experiment. Melanoma growth was monitored by orthagonal caliper measurements every 3-4 days between day 15 to day 32.

Soft Agar Colony Formation Assay.

Complete growth media—0.7% agar was overlaid with complete growth media—3.5% agar containing 10,000 cells and additional complete growth media. After 2 weeks, colonies were stained with MTT(Sigma) to identify viable colonies and imaged by a ChemiDoc XRSplus system as previously described [6]. Images were analyzed with NIH ImageJ to enumerate colony number.

Statistical Analysis.

Unpaired t-test were used to compare mean differences between control and treatment groups. Univariate ANOVA followed by Tukey's post hoc test were performed to analyze data containing three or more groups. For time lapse extracellular flux analysis repeated measures ANOVA analysis was performed. GraphPad was used for all statistical analyses.

References for Example 2

Allavena, P., Sica, A., Garlanda, C., and Mantovani, A. (2008). The Yin-Yang of tumor-associated macrophages in neoplastic progression and immune surveillance. Immunol Rev 222, 155-161.

Banchereau, J., and Steinman, R. (1998). Dendritic cells and the control of immunity. Nature 392, 245-252.

Dong, H., and Bullock, T. N. (2014). Metabolic influences that regulate dendritic cell function in tumors. Frontiers in immunology 5, 24.

Elghazi, L., Gould, A. P., Weiss, A. J., Barker, D. J., Callaghan, J., Opland, D., Myers, M., Cras-Meneur, C., and Bernal-Mizrachi, E. (2012). Importance of beta-Catenin in glucose and energy homeostasis. Scientific reports 2, 693.

Everts, B., Amiel, E., Huang, S. C., Smith, A. M., Chang, C. H., Lam, W. Y., Redmann, V., Freitas, T. C., Blagih, J., van der Windt, G. J., et al. (2014). TLR-driven early glycolytic reprogramming via the kinases TBK1-IKKvarepsilon supports the anabolic demands of dendritic cell activation. Nat Immunol 15, 323-332.

Fallarino, F., Grohmann, U., You, S., McGrath, B. C., Cavener, D. R., Vacca, C., Orabona, C., Bianchi, R., Belladonna, M. L., Volpi, C., et al. (2006). The combined effects of tryptophan starvation and tryptophan catabolites down-regulate T cell receptor {zeta}-chain and induce a regulatory phenotype in naive T cells. J Immuno) 176, 6752-6761.

Gabrilovich, D. (2004). Mechanisms and functional significance of tumor-induced dendritic cell defects. Nature Rev Immunol 4, 941-952.

Gajewski, T., Meng, Y., Blank, C., Brown, I., Kacha, A., Kline, J., and Harlin, H. (2006). Immune resistance orchestrated by the tumor microenvironment. Immunol Rev 213, 131-145.

Grohmann, U., Fallarino, F., Bianchi, R., *Belladonna*, M. L., Vacca, C., Orabona, C., Uyttenhove, C., Fioretti, M. C., and Puccetti, P. (2001). IL-6 inhibits the tolerogenic function of CD8 alpha+dendritic cells expressing indoleamine 2,3-dioxygenase. J Immunol 167, 708-714.

Handschin, C., Lin, J., Rhee, J., Peyer, A. K., Chin, S., Wu, P. H., Meyer, U. A., and Spiegelman, B. M. (2005). Nutritional regulation of hepatic heme biosynthesis and *porphyria* through PGC-)alpha. Cell 122, 505-515.

Hanks, B. A., Holtzhausen, A., Jamieson, R., Gimpel, P., Campbell, O., Sun, L., Tewari, A., George, A., Starr, M., Nixon, A., et al. (2013). Type III TGF-β Receptor Down-regulation Generates an Immunotolerant Tumor Microenvironment. J Clin Invest 123, 3925-3940.

Herber, D. L., Cao, W., Nefedova, Y., Novitskiy, S. V., Nagaraj, S., Tyurin, V. A., Corzo, A., Cho, H. I., Celis, E., Lennox, B., et al. (2010). Lipid accumulation and dendritic cell dysfunction in cancer. Nat Med 16, 880-886.

Holtzhausen, A., Zhao, F., Evans, K., Tsutsui, M., Orabona, C., Tyler, D. S., and Hanks, B. A. (2015). Melanoma-derived Wnt5a Promotes Local Dendritic-Cell Expression of IDO and Immunotolerance: Opportunities for Pharmacologic Enhancement of Immunotherapy. Cancer Immunol Res 3, 1082-1095. Hong, Y., Manoharan, I., Suryawanshi, A., Majumdar, T., Angus-Hill, M. L., Koni, P. A., Manicassamy, B., Mellor, A. L., Munn, D. H., and Manicassamy, S. (2015). beta-Catenin Promotes Regulatory T-cell Responses in Tumors by Inducing Vitamin A Metabolism in Dendritic Cells. Cancer Res 75, 656-665.

Hryhorenko, E. A., Rittenhouse-Diakun, K., Harvey, N. S., Morgan, J., Stewart, C. C., and Oseroff, A. R. (1998). Characterization of endogenous protoporphyrin IX induced by delta-aminolevulinic acid in resting and activated peripheral blood lymphocytes by four-color flow cytometry. Photochem Photobiol 67, 565-572.

Hugo, W., Zaretsky, J. M., Sun, L., Song, C., Moreno, B. H., Hu-Lieskovan, S., Berent-Maoz, B., Pang, J., Chmielowski, B., Cherry, G., et al. (2016). Genomic and Transcriptomic Features of Response to Anti-PD-1 Therapy in Metastatic Melanoma. Cell 165, 35-44.

Hunter, G. A., and Ferreira, G. C. (2011). Molecular enzymology of 5-aminolevulinate synthase, the gatekeeper of heme biosynthesis. Biochimica et biophysica acta 1814, 1467-1473.

Jansson, E. A., Are, A., Greicius, G., Kuo, I. C., Kelly, D., Arulampalam, V., and Pettersson, S. (2005). The Wnt/beta-catenin signaling pathway targets PPARgamma activity in colon cancer cells. Proceedings of the National Academy of Sciences of the United States of America 102, 1460-1465.

Ji, R. R., Chasalow, S. D., Wang, L., Hamid, O., Schmidt, H., Cogswell, J., Alaparthy, S., Berman, D., Jure-Kunkel, M., Siemers, N. O, et al. (2012). An immune-active tumor microenvironment favors clinical response to ipilimumab. Cancer Immunol Immunother 61, 1019-1031.

Jiang, A., Bloom, O., Ono, S., Cui, W., Unternaehrer, J., Jiang, S., Whitney, J. A., Connolly, J., Banchereau, J., and Mellman, I. (2007). Disruption of E-cadherin-mediated adhesion induces a functionally distinct pathway of dendritic cell maturation. Immunity 27, 610-624.

Keller, H., Mahfoudi, A., Dreyer, C., Hihi, A. K., Medin, J., Ozato, K., and Wahli, W. (1993). Peroxisome proliferator-activated receptors and lipid metabolism. Annals of the New York Academy of Sciences 684, 157-173.

Kratzner, R., Frohlich, F., Lepler, K., Schroder, M., Roher, K., Dickel, C., Tzvetkov, M. V., Quentin, T., Oetjen, E., and Knepel, W. (2008). A peroxisome proliferator-activated receptor gamma-retinoid X receptor heterodimer physically interacts with the transcriptional activator PAX6 to inhibit glucagon gene transcription. Mol Pharmacol 73, 509-517.

Krawczyk, C. M., Holowka, T., Sun, J., Blagih, J., Amiel, E., DeBerardinis, R. J., Cross, J. R., Jung, E., Thompson, C. B., Jones, R. G., and Pearce, E. J. (2010). Toll-like receptor-induced changes in glycolytic metabolism regulate dendritic cell activation. Blood 115, 4742-4749.

Luke, J. J., Bao, R., Spranger, S., Sweis, R. F., Lingen, M. W., Lengyel, E., Zha, Y., and Gajewski, T. F. (2016). Wnt/Beta-catenin pathway activation correlates with immune exclusion across most human cancers. Journal of Clinical Oncology 34.

Malinarich, F., Duan, K., Hamid, R. A., Bijin, A., Lin, W. X., Poidinger, M., Fairhurst, A. M., and Connolly, J. E. (2015). High mitochondrial respiration and glycolytic capacity represent a metabolic phenotype of human tolerogenic dendritic cells. J Immunol 194, 5174-5186.

Manicassamy, S., Reizis, B., Ravindran, R., Nakaya, H., Salazar-Gonzalez, R. M., Wang, Y. C., and Pulendran, B. (2010). Activation of beta-catenin in dendritic cells regulates immunity versus tolerance in the intestine. Science 329, 849-853.

Mascaro, C., Acosta, E., Ortiz, J. A., Marrero, P. F., Hegardt, F. G., and Haro, D. (1998). Control of human muscle-type carnitine palmitoyltransferase I gene transcription by peroxisome proliferator-activated receptor. J Biol Chem 273, 8560-8563.

Mellor, A. L., and Munn, D. H. (2008). Creating immune privilege: active local suppression that benefits friends, but protects foes. Nat Rev Immunol 8, 74-80.

Mullard, A. (2015). Immunotherapy interest drives IDO deals. Nature reviews. Drug discovery 14, 373-373.

Munn, D. H., and Mellor, A. L. (2007). Indoleamine 2,3-dioxygenase and tumor-induced tolerance. J Clin Invest 117, 1147-1154.

Munn, D. H., Sharma, M. D., Hou, D., Baban, B., Lee, J. R., Antonia, S. J., Messina, J. L., Chandler, P., Koni, P. A., and Mellor, A. L. (2004). Expression of indoleamine 2,3-dioxygenase by plasmacytoid dendritic cells in tumor-draining lymph nodes. J Clin Invest 114, 280-290.

Munn, D. H., Sharma, M. D., Lee, J. R., Jhaver, K. G., Johnson, T. S., Keskin, D. B., Marshall, B., Chandler, P., Antonia, S. J., Burgess, R., et al. (2002). Potential regulatory function of human dendritic cells expressing indoleamine 2,3-dioxygenase. Science 297, 1867-1870.

Napal, L., Marrero, P. F., and Haro, D. (2005). An intronic peroxisome proliferator-activated receptor-binding sequence mediates fatty acid induction of the human carnitine palmitoyltransferase 1A. J Mol Biol 354, 751-759.

Nencioni, A., Grunebach, F., Zobywlaski, A., Denzlinger, C., Brugger, W., and Brossart, P. (2002). Dendritic cell immunogenicity is regulated by peroxisome proliferator-activated receptor gamma. J I mmunol 169, 1228-1235.

O'Neill, L. A., and Pearce, E. J. (2016). Immunometabolism governs dendritic cell and macrophage function. J Exp Med 213, 15-23.

Orabona, C., Pallotta, M. T., Volpi, C., Fallarino, F., Vacca, C., Bianchi, R., Belladonna, M. L., Fioretti, M. C., Grohmann, U., and Puccetti, P. (2008). SOCS3 drives proteasomal degradation of indoleamine 2,3-dioxygenase (IDO) and antagonizes IDO-dependent tolerogenesis. Proceedings of the National Academy of Sciences of the United States of America 105, 20828-20833.

Pallotta, M. T., Orabona, C., Volpi, C., Vacca, C., Belladonna, M. L., Bianchi, R., Servillo, G., Brunacci, C., Calvitti, M., Bicciato, S., et al. (2011). Indoleamine 2,3-dioxygenase is a signaling protein in long-term tolerance by dendritic cells. Nat Immunol 12, 870-878.

Pesce, M. A., Bodourian, S. H., and Nicholson, J. F. (1975). Rapid kinetic measurement of lactate in plasma with a centrifugal analyzer. Clinical chemistry 21, 1932-1934.

Scarlett, U.K., Rutkowski, M. R., Rauwerdink, A. M., Fields, J., Escovar-Fadul, X., Baird, J., Cubillos-Ruiz, J. R., Jacobs, A. C., Gonzalez, J. L., Weaver, J., et al. (2012). Ovarian cancer progression is controlled by phenotypic changes in dendritic cells. J Exp Med 209, 495-506.

Sharma, M. D., Baban, B., Chandler, P. R., Hou, D.-Y., Singh, N., Yagita, H., Azuma, M., Blazar, B. R., Mellor, A. L., and Munn, D. H. (2007). Plasmacytoid dendritic cells from mouse tumor-draining lymph nodes directly activate mature Tregs via indoleamine-2,3-dioxygenase. J Clin Invest 117, 2570-2582.

Sherwood, V., Chaurasiya, S. K., Ekstrom, E. J., Guilmain, W., Liu, Q., Koeck, T., Brown, K., Hansson, K., Agnarsdottir, M., Bergqvist, M., et al. (2014). WNT5A-mediated beta-catenin-independent signalling is a novel regulator of cancer cell metabolism. Carcinogenesis 35, 784-794.

Shimizu, T., Nomiyama, S., Hirata, F., and Hayaishi, 0. (1978). lndoleamine 2,3-dioxygenase. Purification and some properties. J Biol Chem 253, 4700-4706.

Spranger, S., Bao, R., and Gajewski, T. F. (2015). Melanoma-intrinsic beta-catenin signalling prevents anti-tumour immunity. Nature.

Spranger, S., Spaapen, R. M., Zha, Y., Williams, J., Meng, Y., Ha, T. T., and Gajewski, T. F. (2013). Up-regulation of PD-L1, IDO, and T(regs) in the melanoma tumor microenvironment is driven by CD8(+) T cells. Science translational medicine 5, 200ra116.

Sweis, R. F., Spranger, S., Bao, R., Paner, G. P., Stadler, W. M., Steinberg, G., and Gajewski, T. F. (2016). Molecular Drivers of the Non-T-cell-Inflamed Tumor Microenvironment in Urothelial Bladder Cancer. Cancer Immunol Res.

Szatmari, I., Pap, A., Ruhl, R., Ma, J. X., Illarionov, P. A., Besra, G. S., Rajnavolgyi, E., Derso, B., and Nagy, L. (2006). PPARgamma controls CD1d expression by turning on retinoic acid synthesis in developing human dendritic cells. J Exp Med 203, 2351-2362.

Szatmari, I., Torocsik, D., Agostini, M., Nagy, T., Gurnell, M., Barta, E., Chatterjee, K., and Nagy, L. (2007). PPARgamma regulates the function of human dendritic cells primarily by altering lipid metabolism. Blood 110, 3271-3280.

Thomas, S. R., Salahifar, H., Mashima, R., Hunt, N. H., Richardson, D. R., and Stocker, R. (2001). Antioxidants inhibit indoleamine 2,3-dioxygenase in IFN-gamma-activated human macrophages: posttranslational regulation by pyrrolidine dithiocarbamate. J Immunol 166, 6332-6340.

Zhao, F., and Klimecki, W. T. (2015). Culture conditions profoundly impact phenotype in BEAS-2B, a human pulmonary epithelial model. Journal of applied toxicology: JAT 35, 945-951.

Inaba, K., Inaba, M., Romani, N., Aya, H., Deguchi, M., lkehara, S., Muramatsu, S., and Steinman, R. M. (1992). Generation of large numbers of dendritic cells from mouse bone marrow cultures supplemented with granulocyte/macrophage colony-stimulating factor. The Journal of experimental medicine 176, 1693-1702.

Holtzhausen, A., Zhao, F., Evans, K., Tsutsui, M., Orabona, C., Tyler, D. S., and Hanks, B. A. (2015). Melanoma-derived Wnt5a Promotes Local Dendritic-Cell Expression of IDO and Immunotolerance: Opportunities for Pharmacologic Enhancement of Immunotherapy. Cancer Immunol Res 3, 1082-1095.

Shen, Z., Reznikoff, G., Dranoff, G., and Rock, K. L. (1997). Cloned dendritic cells can present exogenous antigens on both MHC class I and class II molecules. J Immunol 158, 2723-2730.

Nair, S., Archer, G. E., and Tedder, T. F. (2012). Isolation and generation of human dendritic cells. In Current Protocols in Immunology. (John Wiley & Sons), pp. 32.31-32.23.

Collier, G. R., Traianedes, K., Macaulay, S. L., and O'Dea, K. (1993). Effect of fatty acid oxidation inhibition on glucose metabolism in diabetic rats. Hormone and metabolic research=Hormon- and Stoffwechselforschung= Hormones et metabolisme 25, 9-12.

Zhao, F., Maim, S. W., Hinchman, A. N., Li, H., Beeks, C. G., and Klimecki, W. T. (2014). Arsenite-induced pseudo-hypoxia results in loss of anchorage-dependent growth in BEAS-2B pulmonary epithelial cells. PloS one 9, e114549.

Figure 23B:
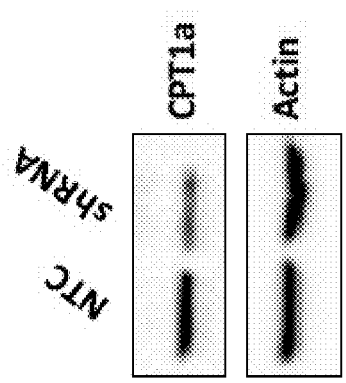
FIG. 23B shows Western blot analysis of CPT1a in purified BMDCs following transduction with a NTC lentiviral vector vs a CPT1a-targeted shRNA-expressing lentiviral vector. BMDC purity>90% based on CD11c+IAb+flow cytometry. NTC, non-targeted control. *p<0.05.
Figure 23A:
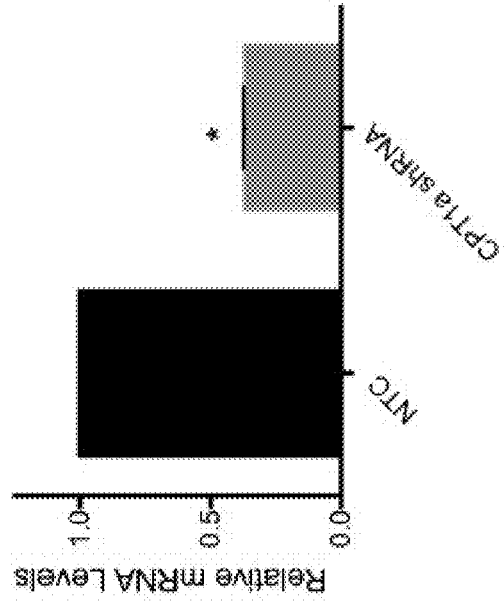
FIG. 23A depicts qrt-PCR analysis of CPT1a in purified BMDCs following transduction with a NTC lentiviral vector vs a CPT1a-targeted shRNA-expressing lentiviral vector.
Figure 24A:
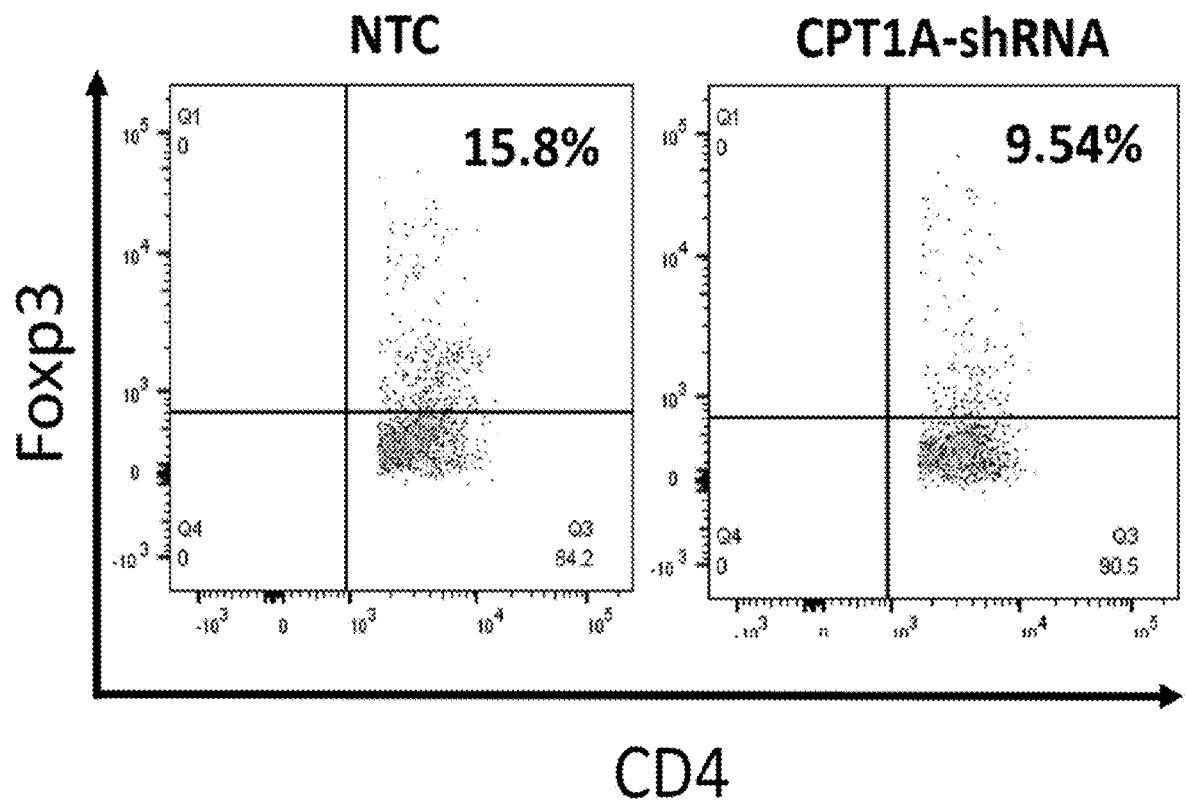
FIG. 24A depicts CPT1aKD DC Induced T Cell responses in an in vitro Treg Differentiation Assay. Purified naïve CD4+ T cells co-cultured with NTC vs CPT1aKD DCs.
Figure 24A:
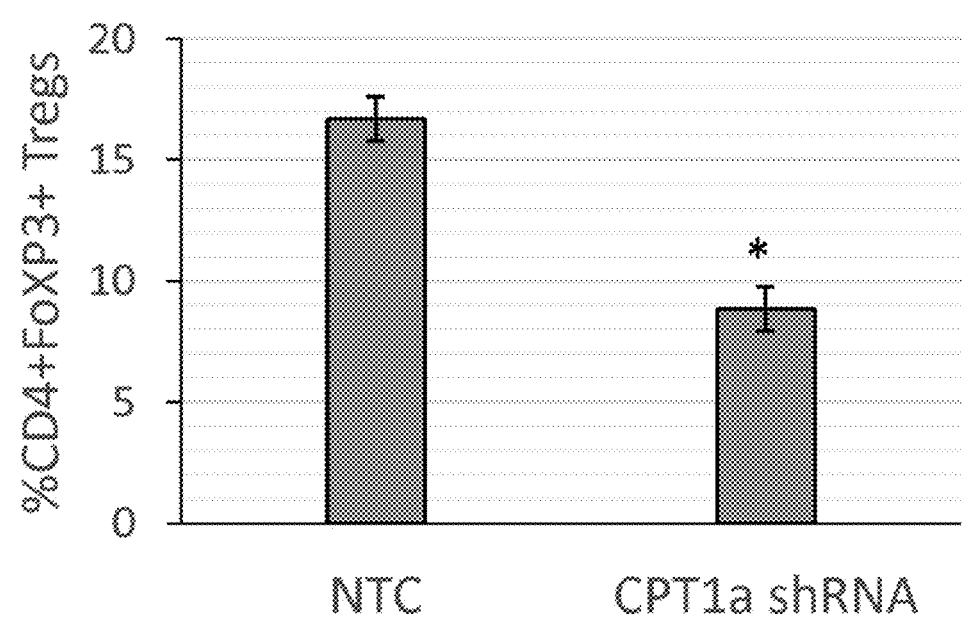
Figure 24B:
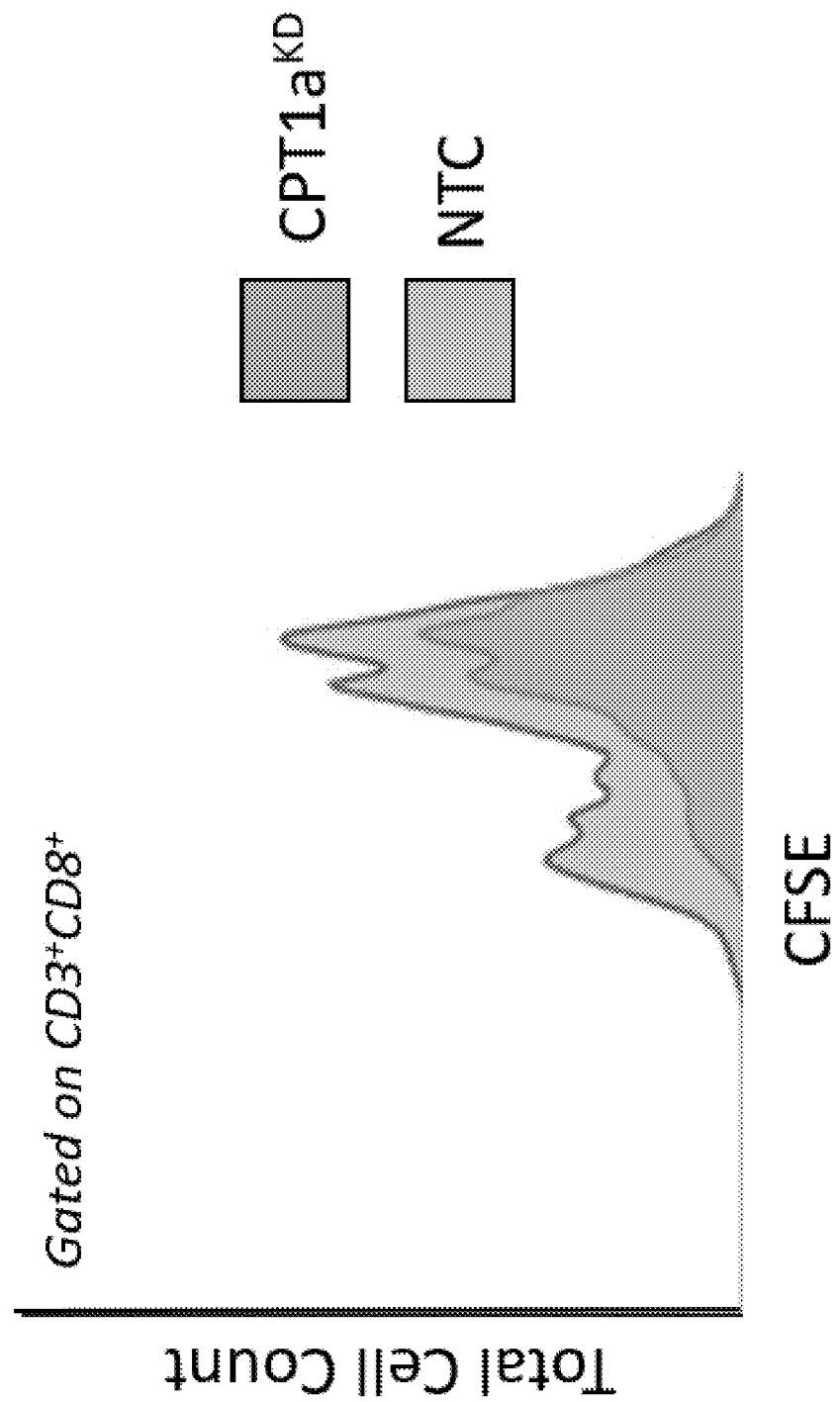
FIG. 24B depicts in vitro CD8+ T Cell Proliferation Assay. CFSE-labeled OT-1 T cells co-cultured with SIIN-FELK (SEQ ID NO:2) peptide-pulsed NTC vs CPT1aKD DCs. Flow cytometry analysis of CFSE dilution gated on CD3+CD8+ cell population. KD, knockdown. *p<0.05.

Example 3: Lentiviral Vector Delivery of CPT1a-Specific shRNA to Dendritic Cells Able to Silence CPT1a and Generate Suppressed Levels of Tregs In order to generate a genetically altered DC-based vaccine capable of inducing a more potent T cell-mediated immune response, we engineered a recombinant CPT1a-specific shRNA-expressing lentiviral vector. We have found this CPT1a-targeted lentiviral vector to effectively silence CPT1a expression in purified, primary bone marrow-derived DCs based on both qrt-PCR and Western blot analysis (FIG. 23). Further work has shown CPT1aKD-DCs to generate suppressed levels of Tregs and enhanced activation of effector CD8+ T cell activation in vitro (FIG. 24).

What is claimed is:

1. A method of treating cancer in a patient treated or being treated with a cancer vaccine, the method comprising: inhibiting fatty acid oxidation in dendritic cells of the patient.

2. The method of claim 1, wherein the dendritic cells are ex vivo vaccine-activated dendritic cells and the method further comprises administering a therapeutically effective amount of the ex vivo vaccine-activated dendritic cells to the patient.

3. The method of claim 2, wherein the method comprises genetically altering the ex vivo vaccine-activated dendritic cells to substantially silence expression of a fatty acid oxidation promoter.

4. The method of claim 3, wherein the fatty acid oxidation promoter is part of the paracrine Wnt-β-catenin signaling pathway.

5. The method of claim 3, wherein the fatty acid oxidation promoter is CPT1a, CPT1b, or CPT1c.

6. The method of claim 1, wherein the dendritic cells are in vivo vaccine-activated dendritic cells and the method comprises administering a therapeutically effective amount of a vector configured to convert native dendritic cells into the in vivo vaccine-activated dendritic cells to the patient.

7. The method of claim 6, wherein the method comprises administering to the patient a therapeutically effective amount of an inhibitor of a promoter of fatty acid oxidation to inhibit fatty acid oxidation in the in vivo vaccine-activated dendritic cells of the patient.

8. The method of claim 7, wherein the promoter of fatty acid oxidation in the in vivo vaccine-activated dendritic cells is part of the paracrine Wnt-β-catenin signaling pathway.

9. The method of claim 7, wherein the promoter of fatty acid oxidation in the in vivo vaccine-activated dendritic cells is CPT1a, CPT1b, or CPT1c.

10. The method of claim 6, wherein the method comprising administering to the patient a therapeutically effective amount of a transfection or transduction agent configured to transfect or transduce the native dendritic cells or the in vivo vaccine-activated dendritic cells with genetic material that reduces expression of a promoter of fatty acid oxidation.

11. The method of claim 10, wherein the promoter of fatty acid oxidation is part of the paracrine Wnt-β-catenin signaling pathway.

12. The method of claim 10, wherein the promoter of fatty acid oxidation is CPT1a, CPT1b, or CPT1c.

13. The method of claim 1, the method further comprising administering a therapeutically effective amount of a checkpoint inhibitor.

* * * * *

UNITED STATES PATENT AND TRADEMARK OFFICE
CERTIFICATE OF CORRECTION

PATENT NO. : 10,617,749 B1
APPLICATION NO. : 15/441816
DATED : April 14, 2020
INVENTOR(S) : Brent Hanks et al.

It is certified that error appears in the above-identified patent and that said Letters Patent is hereby corrected as shown below:

In the Specification

Column 5, Line 53, "DC2.4-O-cat'" should be --DC2.4-$\beta$-cat$^{KD}$--.

Column 5, Line 55, "GSK30" should be --GSK3$\beta$--.

Column 6, Line 18, "*1³" should be --*P--.

Column 6, Line 22, "□□" should be --±--.

Column 15, Lines 42-43, "suppress cell" should be --suppress T cell--.

Column 21, Line 63, "$\beta$-aminolevulinic" should be --$\delta$-aminolevulinic--.

Column 23, Line 52, "CD4$^+$ cells" should be --CD4$^+$ T cells--.

Column 28, Line 54, "(FIG. 1511)" should be --(FIG. 15H)--.

Column 30, Line 54, "BRAFvI$_N$" should be --BRAF$^{V600E}$-PTEN$^{-/-}$--.

Column 32, Line 12, "1100Mjba" should be --1100Mjb/J--.

Column 32, Line 12, "B6.129-Ido1tm1Alma" should be --B6.129-Ido1tm1Alm/J--.

Column 32, Line 36, "□" should be --$\mu$--.

Column 32, Line 57, "4° C" should be --4oC--.

Column 35, Line 59, "J Immuno)" should be --J Immunol--.

Signed and Sealed this
Sixteenth Day of June, 2020

Andrei Iancu
*Director of the United States Patent and Trademark Office*

Column 37, Line 57, "J I mmunol" should be --J Immunol--.

Column 38, Line 41, "Derso" should be --Dezso--.

Column 39, Line 14, "Hormon- and Stoffwechselforschung" should be --Harmon- und Stoffwechselforschung--.

Column 39, Line 16, "Maim" should be --Malm--.